(12) United States Patent
Franzini

(10) Patent No.: US 11,560,384 B2
(45) Date of Patent: Jan. 24, 2023

(54) BENZONORBORNADIENE DERIVATIVES AND REACTIONS THEREOF

(71) Applicant: University of Utah Research Foundation, Salt Lake City, UT (US)

(72) Inventor: Raphael Franzini, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 15/929,012

(22) Filed: May 4, 2018

(65) Prior Publication Data

US 2019/0300539 A1     Oct. 3, 2019

Related U.S. Application Data

(60) Provisional application No. 62/502,427, filed on May 5, 2017, provisional application No. 62/501,656, filed on May 4, 2017.

(51) Int. Cl.
| | | |
|---|---|---|
| C07D 487/08 | (2006.01) | |
| C07D 493/08 | (2006.01) | |
| A61K 47/54 | (2017.01) | |

(52) U.S. Cl.
CPC .......... *C07D 487/08* (2013.01); *A61K 47/545* (2017.08); *A61K 47/555* (2017.08); *C07D 493/08* (2013.01)

(58) Field of Classification Search
CPC .. C07D 487/08; C07D 493/08; A61K 47/545; A61K 47/555
See application file for complete search history.

(56) References Cited

U.S. PATENT DOCUMENTS

| | | |
|---|---|---|
| 6,878,718 B2 | 4/2005 | Brand et al. |
| 7,122,556 B2 | 10/2006 | Brand et al. |
| 7,501,437 B2 | 3/2009 | Brand et al. |
| 7,531,549 B2 | 5/2009 | Brand et al. |
| 7,781,615 B2 | 8/2010 | Tobler et al. |
| 7,807,140 B2 | 10/2010 | Kiessling et al. |
| 8,236,949 B2 | 8/2012 | Fox et al. |
| 8,278,311 B2 | 10/2012 | Liu et al. |
| 8,536,205 B2 | 9/2013 | Branda et al. |
| 8,546,410 B2 | 10/2013 | Liu et al. |
| 8,900,549 B2 | 12/2014 | Hilderbrand et al. |
| 8,940,501 B2 | 1/2015 | Ploegh et al. |
| 9,085,514 B2 | 7/2015 | Lemke et al. |
| 9,212,381 B2 | 12/2015 | Salic et al. |
| 9,289,516 B2 | 3/2016 | Weissleder et al. |
| 9,303,068 B2 | 4/2016 | Bertozzi et al. |
| 9,382,473 B2 | 7/2016 | Chiu et al. |
| 2008/0063602 A1 | 3/2008 | Kiessling et al. |
| 2011/0268654 A1 | 11/2011 | Hilderbrand et al. |
| 2012/0282632 A1 | 11/2012 | Chiu et al. |
| 2013/0122535 A1 | 5/2013 | Salic et al. |
| 2013/0189287 A1 | 7/2013 | Bregeon et al. |
| 2013/0302246 A1 | 11/2013 | Hilderbrand et al. |
| 2014/0335018 A1 | 11/2014 | Wong et al. |
| 2015/0125884 A1 | 5/2015 | Budin et al. |
| 2015/0165064 A1 | 6/2015 | Bregeon et al. |
| 2015/0241440 A1 | 8/2015 | Fasan et al. |
| 2015/0246893 A1 | 9/2015 | Devaraj et al. |
| 2015/0343100 A1 | 12/2015 | Perez-Medina et al. |
| 2015/0344514 A1 | 12/2015 | Robillard et al. |
| 2016/0000864 A1 | 1/2016 | Wong et al. |
| 2016/0121002 A1 | 5/2016 | Meimetis et al. |
| 2016/0168205 A1 | 6/2016 | Salic et al. |

FOREIGN PATENT DOCUMENTS

| | | |
|---|---|---|
| AU | 2012/356894 | 7/2014 |
| AU | 2014/265659 | 11/2015 |
| CA | 2858806 A1 | 6/2013 |
| CA | 2911414 A1 | 11/2014 |
| CA | 2914189 A1 | 12/2014 |
| CN | 102791827 A | 11/2012 |
| CN | 104356110 A | 2/2015 |
| EA | 200500574 A1 | 10/2005 |
| EA | 014275 | 10/2008 |
| EP | 2015784 A2 | 1/2009 |
| EP | 2499213 A2 | 9/2012 |
| EP | 2522369 A1 | 11/2012 |
| EP | 2793947 | 10/2014 |

(Continued)

OTHER PUBLICATIONS

Xu et al., Chemical Communications, 2017, 53, 6271-6274.*
Zhang et al., Org. Lett. 2017, 19,5, 1072-1075.*
Webster et al., Organic Letters (2009), vol. 11, No. 20, pp. 4688-4691.*

*Primary Examiner* — Alicia L Otton
(74) *Attorney, Agent, or Firm* — Todd Alder

(57) ABSTRACT

A bioorthogonal molecule can include a molecule having a structure according the above wherein $R^1$-$R^8$ are independently selected from H, a substituted or unsubstituted $C_1$-$C_4$ alkyl or alkylene group, COOH, $COOR^9$, $COR^9$, $CONR^9R^{10}$, CN, $CF_3$, and $SO_2R^9$, and where $R^9$ and $R^{10}$ are independently selected from H and a substituted or unsubstituted $C_1$-$C_4$ alkyl or alkylene group, with the proviso that one of $R^3$-$R^8$ comprises a leaving group, and wherein X is O, S, N, SO, $SO_2$, $SR^+$, Se, $PO_2^-$, or $NRR'^+$, and where R and R' are independently selected from H or a substituted or unsubstituted $C_1$-$C_4$ alkyl or alkylene group.

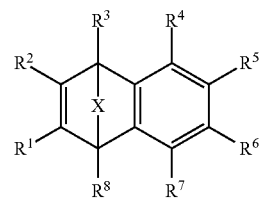

21 Claims, 51 Drawing Sheets

(56) References Cited

FOREIGN PATENT DOCUMENTS

| | | |
|---|---|---|
| EP | 2892929 A1 | 7/2015 |
| EP | 2922574 A1 | 9/2015 |
| EP | 3001813 A1 | 4/2016 |
| EP | 3010548 A1 | 4/2016 |
| GB | 1591533 A | 6/1981 |
| HR | P 20050441 A1 | 9/2006 |
| JP | 2003/512446 A | 4/2003 |
| JP | 5597102 | 6/2011 |
| JP | 5597103 | 6/2011 |
| WO | WO 2004/035589 A1 | 4/2004 |
| WO | WO 2007/068417 A2 | 6/2007 |
| WO | WO 2007/131084 A2 | 11/2007 |
| WO | WO 2010/051530 A2 | 5/2010 |
| WO | WO 2010/119382 A1 | 10/2010 |
| WO | WO 2011/057295 A2 | 5/2011 |
| WO | WO 2011/098386 A1 | 8/2011 |
| WO | WO 2012/049624 A1 | 4/2012 |
| WO | WO 2012/153254 A1 | 11/2012 |
| WO | WO 2012/156919 A1 | 11/2012 |
| WO | WO 2012/156920 A1 | 11/2012 |
| WO | WO 2013/092983 A2 | 6/2013 |
| WO | WO 2013/108044 A2 | 7/2013 |
| WO | WO 2013/171485 A1 | 11/2013 |
| WO | WO 2013/187954 A1 | 12/2013 |
| WO | WO 2014/039715 A1 | 3/2014 |
| WO | WO 2014/065860 A1 | 5/2014 |
| WO | WO 2014/081299 A1 | 5/2014 |
| WO | WO 2014/081300 A1 | 5/2014 |
| WO | WO 2014/081303 A1 | 5/2014 |
| WO | WO 2014/182704 A2 | 11/2014 |
| WO | WO 2014/186301 A1 | 11/2014 |
| WO | WO 2014/202775 A1 | 12/2014 |
| WO | WO 2014/205126 A1 | 12/2014 |
| WO | WO 2015/054658 A1 | 4/2015 |
| WO | WO 2015/074141 A1 | 5/2015 |
| WO | WO 2015/107064 A1 | 7/2015 |
| WO | WO 2015/117235 A1 | 8/2015 |
| WO | WO 2015/139025 A1 | 9/2015 |
| WO | WO 2015/154082 A1 | 10/2015 |
| WO | WO 2015/183876 A1 | 12/2015 |
| WO | WO 2015/197655 A1 | 12/2015 |
| WO | WO 2016/018896 A1 | 2/2016 |
| WO | WO 2016/066749 A1 | 5/2016 |
| WO | WO 2018004338 A1 | 1/2018 |
| WO | WO 2014/138186 A1 | 9/2018 |

\* cited by examiner

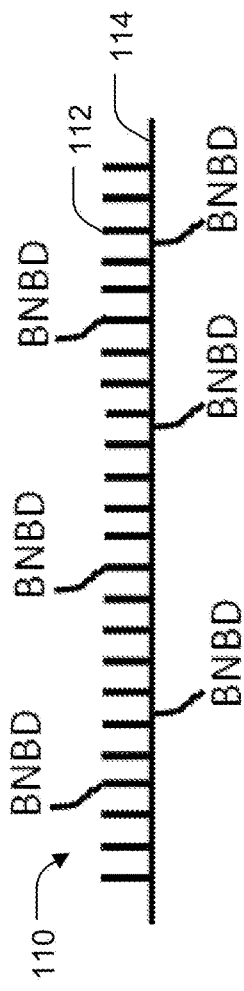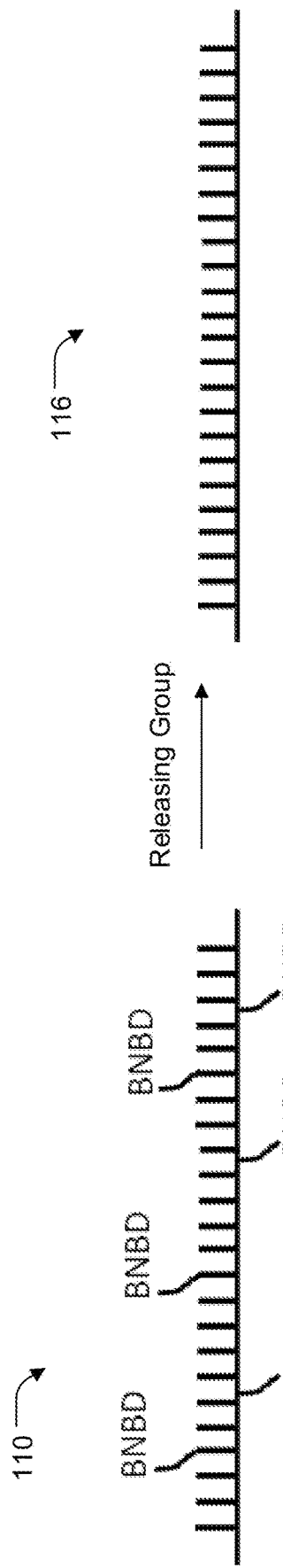

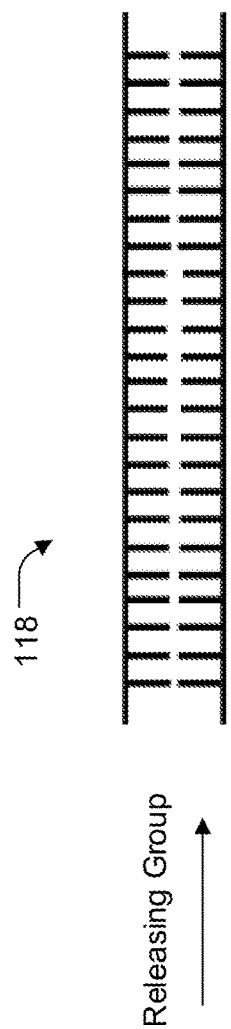
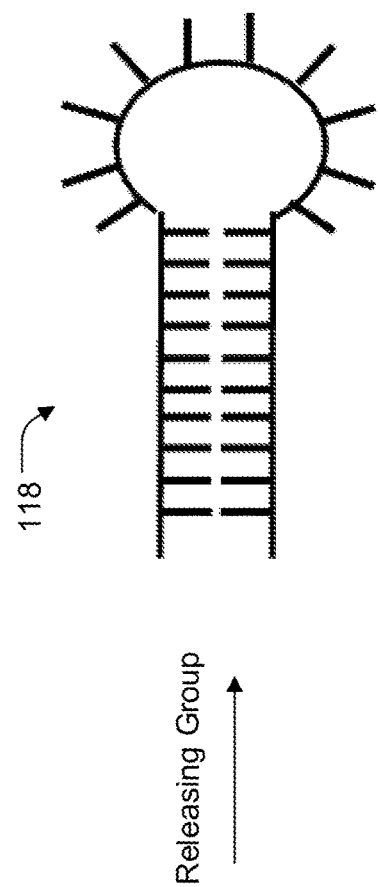
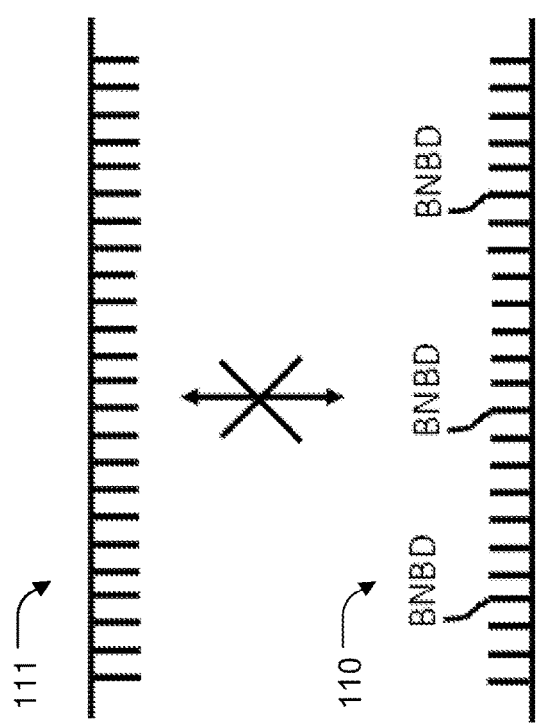
FIG. 5C
FIG. 5D

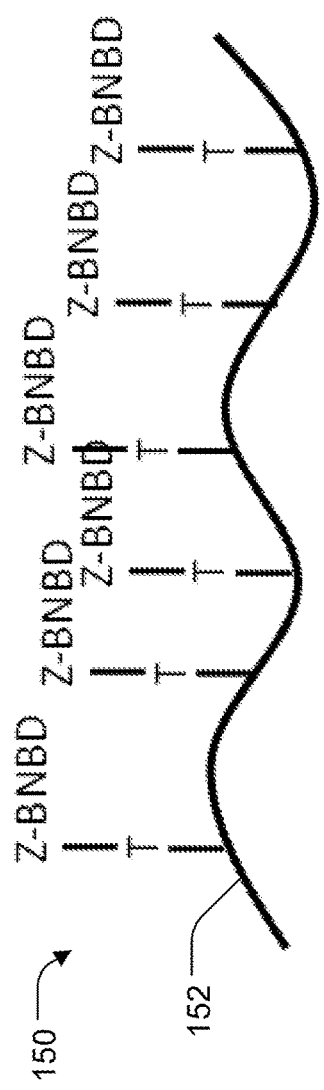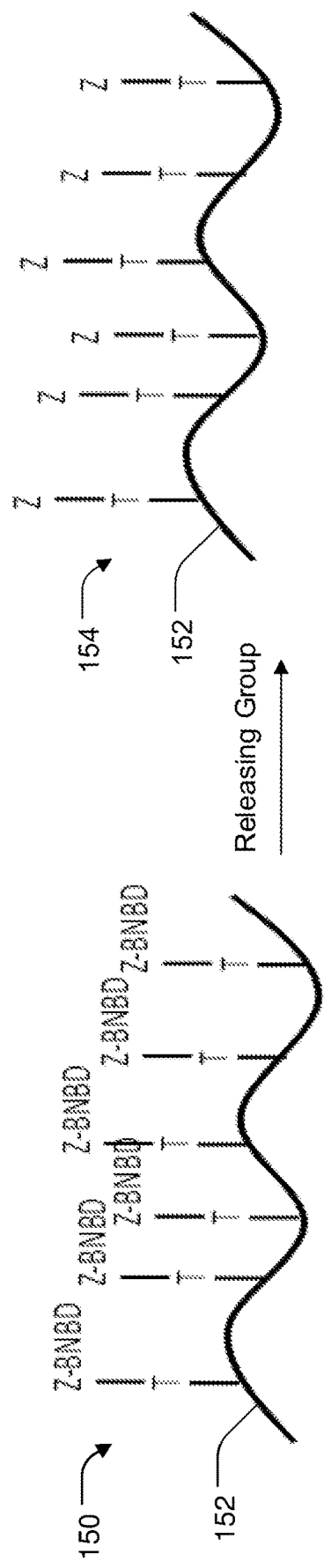

BENZONORBORNADIENE DERIVATIVES AND REACTIONS THEREOF

RELATED APPLICATION(S)

This application claims the benefit of U.S. Provisional Application No. 62/501,656 filed on May 4, 2017 and U.S. Provisional Application No. 62/502,427 filed on May 5, 2017, each of which is incorporated herein by reference.

BACKGROUND

Bioorthogonal chemistry generally refers to chemical reactions that can occur in biological systems without interfering with native biochemical processes. Bioorthogonal chemistry provides reactions that are compatible with biomolecules, which facilitates the performance of chemistry in living organisms. Biocompatible reaction development has focused primarily on transformations that link two molecules, as such bioorthogonal ligation reactions have broad applicability in bioconjugation chemistry, materials science, and chemical biology. Such reactions have further been used to localize drugs and imaging agents at sites of disease.

BRIEF DESCRIPTION OF THE DRAWINGS

FIG. 5A illustrates a modified nucleic acid, in accordance with an example of the present disclosure.

FIG. 5B illustrates a method of reconstituting a modified nucleic acid, in accordance with an example of the present disclosure.

FIG. 5C illustrates a method of controlling hybridization between individual nucleic acids, in accordance with an example of the present disclosure.

FIG. 5D illustrates a method of controlling nucleic acid folding, in accordance with an example of the present disclosure.

FIG. 9A illustrates a carrier molecule having a bioorthogonal molecule attached thereto, in accordance with an example of the present disclosure.

FIG. 9B illustrates a method of retaining a leaving group Z on a carrier molecule, in accordance with an example of the present disclosure.

Figure 1A:
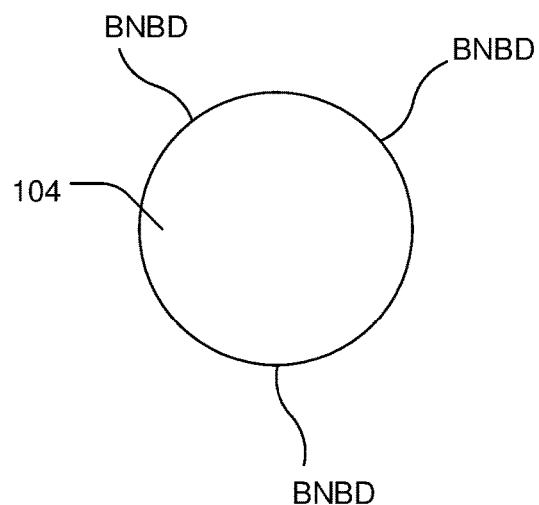
FIG. 1A illustrates a modified target molecule, in accordance with an example of the present disclosure.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

As used herein, the term "about" is used to provide flexibility and imprecision associated with a given term, metric or value. The degree of flexibility for a particular variable can be readily determined by one skilled in the art. However, unless otherwise enunciated, the term "about" generally connotes flexibility of less than 5% in some examples, less than 1% in other examples, and less than 0.01% in yet other examples.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

The term "dosage unit" or "dose" are understood to mean an amount of an active agent that is suitable for administration to a subject in order achieve or otherwise contribute to a therapeutic effect. In some examples, a dosage unit can refer to a single dose that is capable of being administered to a subject or patient, and that may be readily handled and packed, remaining as a physically and chemically stable unit dose.

As used herein, a "dosing regimen" or "regimen" such as "treatment dosing regimen," or a "prophylactic dosing regimen" refers to how, when, how much, and for how long a dose of an active agent or composition can or should be administered to a subject in order to achieve an intended treatment or effect.

As used herein, the terms "treat," "treatment," or "treating" refers to administration of a therapeutic agent to subjects who are either asymptomatic or symptomatic. In other words, "treat," "treatment," or "treating" can be to reduce, ameliorate or eliminate symptoms associated with a condition present in a subject, or can be prophylactic, (i.e. to prevent or reduce the occurrence of the symptoms in a subject). Such prophylactic treatment can also be referred to as prevention of the condition.

As used herein, the terms "therapeutic agent," "active agent," and the like can be used interchangeably and refer to an agent that can have a beneficial or positive effect on a subject when administered to the subject in an appropriate or effective amount.

The phrase "effective amount," "therapeutically effective amount," or "therapeutically effective rate(s)" of an active ingredient refers to a substantially non-toxic, but sufficient amount or delivery rates of the active ingredient, to achieve therapeutic results in treating a disease or condition for which the drug is being delivered. It is understood that various biological factors may affect the ability of a substance to perform its intended task. Therefore, an "effective amount," "therapeutically effective amount," or "therapeutically effective rate(s)" may be dependent in some instances on such biological factors. Further, while the achievement of therapeutic effects may be measured by a physician or other qualified medical person using evaluations known in the art, it is recognized that individual variation and response to treatments may make the achievement of therapeutic effects a subjective decision. The determination of a therapeutically effective amount or delivery rate is well within the ordinary skill in the art of pharmaceutical sciences and medicine.

As used herein, "formulation" and "composition" can be used interchangeably and refer to a combination of at least two ingredients. In some embodiments, at least one ingredient may be an active agent or otherwise have properties that exert physiologic activity when administered to a subject. For example, amniotic fluid includes at least two ingredients (e.g. water and electrolytes) and is itself a composition or formulation.

As used herein, a "subject" refers to an animal. In one aspect the animal may be a mammal. In another aspect, the mammal may be a human.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be presented herein in a range format. It is to be understood that such range format is used merely for convenience and brevity, and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Bioorthogonal Molecules, Compositions, and Reactions

Bioorthogonal chemistry provides biomolecule-compatible reactions capable of being performed in living organisms. Biocompatible reaction development has focused primarily on transformations that link two molecules, as such bioorthogonal ligation reactions have broad applicability in bioconjugation chemistry, materials science, and chemical biology. Such reactions can be used to localize drugs and imaging agents at specific locations, such as sites of disease. In contrast, the discovery of bioorthogonal cleavage reactions that allow for the controlled release of payloads has only recently attracted substantial research interest, even though such reactions are valuable in a wide range of applications. For example, dissociative bioorthogonal reactions can be used in proximity-reporting analytical probes for sensing genetic markers and proteins in cells and in animals. Further applications can include DNA sequencing, enzyme uncaging, cell imaging, biomacromolecule purification, multiplexed in situ protein detection, and as ultramild protecting groups, to name a few. Applications of dissociative in vivo chemistry leading to spatiotemporally controlled release of drugs are particularly appealing because of the potential for clinical translation in cancer chemotherapy. For example, implantation of tetrazine (Tz)-modified biomaterials can facilitate the localized activation of prodrugs (e.g. doxorubicin), potentially providing significantly more potent anti-tumor effects relative to systemic doxorubicin administration, which can also reduce side-effects. In another example approach, bioorthogonal reactions can be designed to activate antibody-drug conjugates in vivo. In this pre-targeting strategy, an antibody conjugated with a drug via a chemically-cleavable linker can accumulate at a desired site, and the subsequent administration of a trigger molecule can liberate the cytotoxic agent specifically in the target tissue.

The scarcity of bioorthogonal bond-cleavage reactions, however, remains a key bottleneck for the advancement of reaction-based applications in chemical biology and smart therapeutics. Until recently, modified Staudinger reactions were the only bioorthogonal release reactions available. The development of the inverse-electron demand Diels-Alder (IEDDA) pyridazine elimination reaction between carbamate-modified trans-cyclooctenes (TCO) and Tz was a breakthrough in this regard. The rate of this reaction was significantly faster than the Staudinger reaction, and it obviated the use of metabolically unstable phosphines, allowing for widespread use in chemical biology. Further examples of bioorthogonal cleavage reactions included the strain-promoted 1,3-dipolar cycloaddition of TCO and p-azidobenzylcarbamates, and Tz-mediated removal of vinyl ethers. However, reactions need to meet several strict requirements for in vivo use, including rapid reaction rate, near-quantitative payload release, non-toxic reagents, and extended serum stability. Currently available reactions meet these conditions only partially and further development will be necessary to achieve the full potential of in vivo drug activation.

Accordingly, the present disclosure describes bioorthogonal molecules (occasionally referred to herein as BNBD) that address many of these concerns. Generally, bioorthogonal molecules can have a structure according to Formula I:

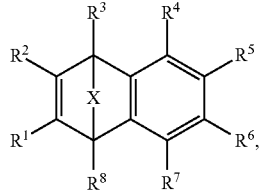

(I)

where X is a heteroatom, such as oxygen, sulfur, (modified) nitrogen, or the like, for example. $R^1$-$R^8$ are individually selected from hydrogen or a substituted or unsubstituted $C_1$-$C_4$ alkyl or alkylene group, COOH, COOR$^9$, COR$^9$, CONR$^9$R$^{10}$, CN, CF$_3$, SO$_2$R$^9$, or the like, with the proviso that one of $R^3$-$R^8$ comprises a leaving group. In some examples, $R^9$ and $R^{10}$ are independently selected from H and a substituted or unsubstituted $C_1$-$C_4$ alkyl or alkylene group.

In further detail, X can include a variety of heteroatoms. Some non-limiting examples of X can include O, S, N, N—Ac, N-Boc, SO, SO$_2$, SR$^+$, Se, PO$_2^-$, NRR'$^+$, or the like. In some examples, R and R' are independently selected from H or a substituted or unsubstituted $C_1$-$C_4$ alkyl or alkylene group. In some specific examples, X can include O or N, including N modified with acyl, alkyl, aryl, heteroaryl, and alkyoxycaronyl groups.

In some additional examples, $R^1$, $R^2$, or both can include an electron-withdrawing group E. A variety of electron withdrawing groups can be used in the bioorthogonal molecules, such as halides, amides, esters, carboxylic acids, acyl chlorides, ketones, aldehydes, amines, nitro groups, sulfonates, cyano groups, trihalides, the like, or a combination thereof. Non-limiting examples can include —COOH, —COOR$^9$, —COR$^9$, —CONR$^9$R$^{10}$, —CN, —CF$_3$, —SO$_2$R$^9$, —NO$_2$, or the like. In some examples, $R^9$ and $R^{10}$ are independently selected from H and a substituted or unsubstituted $C_1$-$C_4$ alkyl or alkylene group. In some examples, $R^1$ can include an electron withdrawing group. In some additional examples, $R^2$ can include an electron withdrawing group. In yet other examples, both $R^1$ and $R^2$ can include an electron withdrawing group. Thus, in some examples, the bioorthogonal molecule can have a structure according to Formula II:

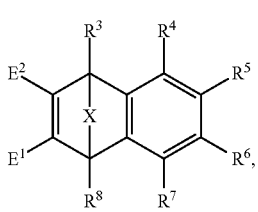

(II)

such as

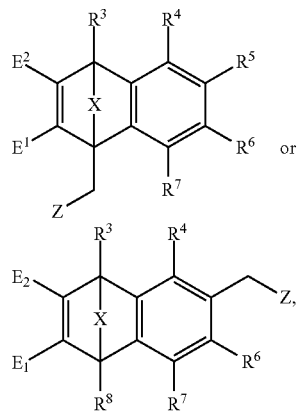

for example, where Z is a leaving group.

A variety of leaving groups can be used in the present bioorthogonal molecules. In some examples, the leaving group can be an A-Z group, where A is a linker group and Z is a leaving group. Where this is the case, the linker group can generally include a $C_1$-$C_3$ alkyl or alkylene group, although a variety of other linker groups may also be employed. Thus, in some examples, the leaving group can include —CH$_2$—Z, —CR$^1$(R$^2$)—Z, —CH—CH—CH$_2$—Z, or the like, which can be used for the controlled release of Z. Further, while the A-Z group can be positioned at any of $R^3$-$R^8$, in some specific examples, the A-Z group can be positioned at $R^5$ or $R^8$, such as in

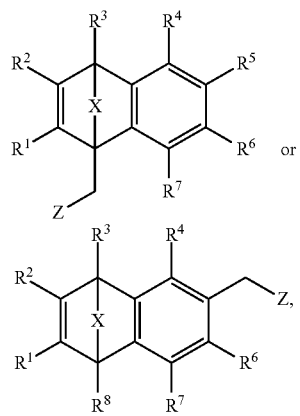

for example. Thus, in some examples, $R^5$ can include the leaving group. In other examples, $R^8$ can include the leaving group.

Z can also include a variety of suitable leaving groups. Non-limiting examples can include

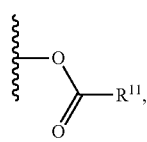

(esters, carbonates, carbamates)

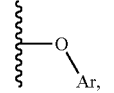

(Aromatic ethers)

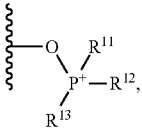

(Phosphates and derivatives thereof)

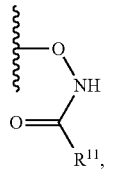

(Hydroxamate esters)

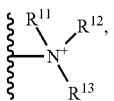

(ammonium compounds)

or the like. Thus, in some examples, the leaving group can include $COOR^{11}$, $O$-Aryl-$R^{11}$, $POR^{11}R^{12}R^{13+}$, $ONHOR^{11}$, or $NR^{11}R^{12}R^{13+}$, wherein $R^{11}$, $R^{12}$, and $R^{13}$ are independently selected from a second leaving group (e.g. a payload, a substrate, a reporter molecule, etc.), H, and a substituted or unsubstituted $C_1$-$C_4$ alkyl or alkylene group. In some specific examples, the leaving group can include $COOR^{11}$ or $POR^{11}R^{12}R^{13+}$, wherein $R^{11}$, $R^{12}$, and $R^{13}$ are independently selected from a second leaving group (e.g. a payload, a substrate, a reporter molecule, etc.), H, and a substituted or unsubstituted $C_1$-$C_4$ alkyl or alkylene group.

In some further examples, Z can be a releasable bioactive molecule D (drug, prodrug, therapeutic agent, vitamin, cytotoxic agent, the like). The drug can be attached directly to the general structure or via an immolative or cleavable linker, as described above. Accordingly, in some examples, the bioorthogonal molecule can have a structure such as

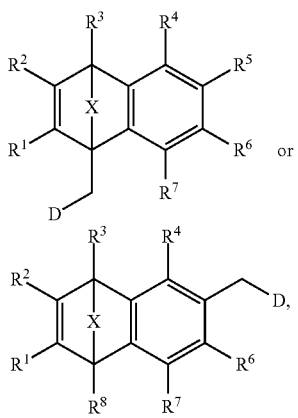

for example. In yet other examples, Z can be a reporter molecule (e.g. chromophore, fluorophore, profluorophore, luminophore, chemiluminophore, dye, radionuclide, or the like). In still additional examples, Z can be an affinity binder (e.g. biotin or derivatives thereof, for example).

In some examples, one or more of the substituents $R^1$-$R^8$ or X of the bioorthogonal molecule can include a tether (T), which can be chemically modified or conjugated as desired. Non-limiting examples of bioorthogonal molecules including a tether can be represented by

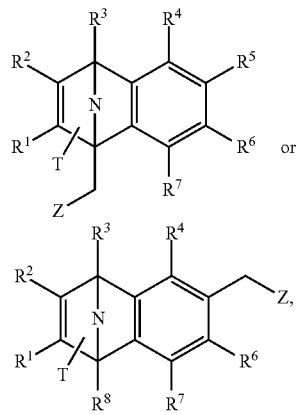

for example. However, the tether group need not attach at X. As illustrated in

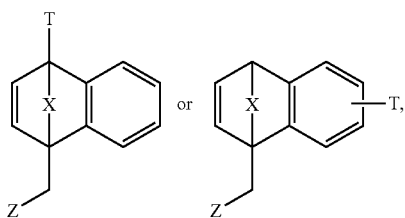

the tether group can be attached at any one of $R^1$-$R^8$ or X. In some specific examples, the tether group can be attached at one of $R^3$-$R^8$ or X. In some examples, the tether group can be attached at one of $R^3$-$R^8$. In still other examples, the tether group can be attached at X.

A tether group (T) can link the bioorthogonal molecule to a variety of substrates, such as a biomolecule (e.g. glutathione, serum albumin, immunoglobulin, DNA, RNA), a homing molecule (e.g. small-molecule ligand, peptide, polypeptide), a macromolecule (e.g. polymer, dendrimer, micelle), the like, or a combination thereof.

In some examples, bioorthogonal molecules can have a structure according to Formula V:

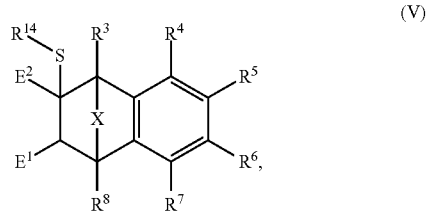

(V)

which can be formed by the reaction of compositions containing a bioorthogonal molecule having a structure according to Formula I and suitable nucleophiles, in which one of the substituents $R^3$-$R^8$ includes a releasable group Z, one of both of $R^1$ and $R^2$ can include an electron withdrawing group as described elsewhere herein, and $R^2$ can additionally include an $SR^{14}$ group. In some examples, $R^4$ can include H or a substituted or unsubstituted $C_1$-$C_4$ alkyl or alkylene group. In some examples, $R^4$ can be a biomolecule (e.g. glutathione, serum albumin, immunoglobulin, DNA, RNA). In some examples, a homing molecule can be linked to bioorthogonal molecule either directly or via a tether. In some examples, $R^4$ can be a homing molecule (e.g. small-molecule ligand, peptide, polypeptide) and the homing molecule can be linked to the bioorthogonal molecule either directly or via a tether. In some examples, $R^{14}$ can be a material or macromolecule (e.g. polymer, dendrimer, micelle), which, in some examples, can be linked to the bioorthogonal molecule either directly or via a tether. In some specific examples, Z can be positioned at the $R^5$ or $R^8$ position to generate a molecule such as

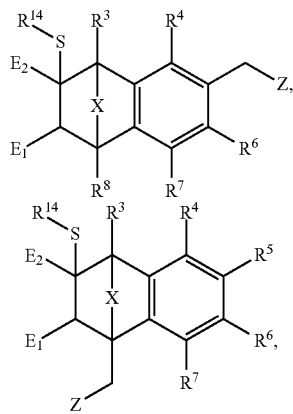

or the like.

Bioorthogonal molecules according to Formula I can be prepared in a variety of ways. For example, a bioorthogonal molecule having a structure according to Formula I can be prepared by reaction with a suitable nucleophile. As one non-limiting example, a precursor molecule of a bioorthogonal molecule having a structure according to Formula I can include an A-OH group, such as —$CH_2OH$, for example, at the $R^3$-$R^8$ group where it is desirable to position the A-Z group. The precursor molecule can be reacted with a suitable nucleophile to generate a bioorthogonal molecule having a structure according to Formula I. Similarly, Z can include a second leaving group (e.g., 4-nitrophenyloxy, perfluorophenyloxy, succinimidyl, halide, etc., for example). In additional examples, Z can include a leaving group (e.g., halide, sulfonate) and that forms a bioorthogonal molecule having a structure according to Formula I upon reaction with a suitable nucleophile.

The bioorthogonal molecule can also be included in a therapeutic composition. The therapeutic composition can include an effective amount or a therapeutically effective amount of a therapeutic agent coupled to the bioorthogonal molecule in a pharmaceutically acceptable carrier. As will be appreciated by one skilled in the art, the effective amount or therapeutically effective amount can be highly dependent on the particular therapeutic agent linked to the bioorthogonal molecule. Further a variety of therapeutic agents can be linked to the bioorthogonal molecule, such as a drug, prodrug, vitamin, cytotoxic agent, other therapeutic agent, the like, or a combination thereof. Nonlimiting examples of possible therapeutic agents can include doxorubicin, auristatins, mitomycin C, and the like.

The bioorthogonal molecule can be included in a pharmaceutically acceptable carrier. The nature of the pharmaceutically acceptable carrier can depend on the intended mode of administration. For example, the pharmaceutically acceptable carrier can be formulated to administer the therapeutic composition via injection, enteral administration, topical administration, transdermal administration, transmucosal administration, inhalation, implantation, or the like.

In some examples, the pharmaceutically acceptable carrier can be formulated to provide a therapeutic composition for administration via injection, such as intramuscular injection, intravenous injection, subcutaneous injection, intradermal injection, intrathecal injection, intraocular injection, or the like. In such examples, the pharmaceutically acceptable carrier can include a variety of components, such as water, a solubilizing or dispersing agent, a tonicity agent, a pH adjuster or buffering agent, a preservative, a chelating agent, a bulking agent, the like, or a combination thereof.

In some examples, an injectable therapeutic composition can include a solubilizing or dispersing agent. Non-limiting examples of solubilizing or dispersing agents can include polyoxyethylene sorbitan monooleates, lecithin, polyoxyethylene polyoxypropylene co-polymers, propylene glycol, glycerin, ethanol, polyethylene glycols, sorbitol, dimethylacetamide, polyethoxylated castor oils, n-lactamide, cyclodextrins, carboxymethyl cellulose, acacia, gelatin, methyl cellulose, polyvinyl pyrrolidone, the like, or combinations thereof.

In some examples, an injectable therapeutic composition can include a tonicity agent. Non-limiting examples of tonicity agents can include sodium chloride, potassium chloride, calcium chloride, magnesium chloride, mannitol, sorbitol, dextrose, glycerin, propylene glycol, ethanol, trehalose, phosphate-buffered saline (PBS), Dulbecco's PBS, Alsever's solution, Tris-buffered saline (TBS), water, balanced salt solutions (BSS), such as Hank's BSS, Earle's BSS, Grey's BSS, Puck's BSS, Simm's BSS, Tyrode's BSS, and BSS Plus, the like, or combinations thereof. The tonicity agent can be used to provide an appropriate tonicity of the therapeutic composition. In one aspect, the tonicity of the therapeutic composition can be from about 250 to about 350 milliosmoles/liter (mOsm/L). In another aspect, the tonicity of the therapeutic composition can be from about 277 to about 310 mOsm/L.

In some examples, an injectable therapeutic composition can include a pH adjuster or buffering agent. Non-limiting examples of pH adjusters or buffering agents can include a number of acids, bases, and combinations thereof, such as hydrochloric acid, phosphoric acid, citric acid, sodium hydroxide, potassium hydroxide, calcium hydroxide, acetate buffers, citrate buffers, tartrate buffers, phosphate buffers, triethanolamine (TRIS) buffers, the like, or combinations thereof. Typically, the pH of the therapeutic composition can be from about 5 to about 9, or from about 6 to about 8.

In some examples, an injectable therapeutic composition can include a preservative. Non-limiting examples of preservatives can include ascorbic acid, acetylcysteine, bisulfite, metabisulfite, monothioglycerol, phenol, metacresol, benzyl alcohol, methyl paraben, propyl paraben, butyl paraben, benzalkonium chloride, benzethonium chloride, butylated hydroxyl toluene, myristyl gamma-picolinium chloride, 2-phenoxyethanol, phenyl mercuric nitrate, chlorobutanol, thimerosal, tocopherols, the like, or combinations thereof.

In some examples, an injectable therapeutic composition can include a chelating agent. Non-limiting examples of chelating agents can include ethylenediaminetetra acetic acid, calcium, calcium disodium, versetamide, calteridol, diethylenetriaminepenta acetic acid, the like, or combinations thereof.

In some examples, an injectable therapeutic composition can include a bulking agent. Non-limiting examples of bulking agents can include sucrose, lactose, trehalose, mannitol, sorbitol, glucose, rafinose, glycine, histidine, polyvinyl pyrrolidone, the like, or combinations thereof.

In yet other examples, the pharmaceutically acceptable carrier can be formulated to provide a therapeutic composition for enteral administration, such as via solid oral dosage forms or liquid oral dosage forms. In the case of solid oral dosage forms, the pharmaceutically acceptable carrier can include a variety of components suitable for forming a capsule, tablet, or the like. In the case of a liquid dosage form, the pharmaceutically acceptable carrier can include a variety of components suitable for forming a dispersion, a suspension, a syrup, an elixir, or the like.

In some specific examples, the therapeutic composition can be formulated as a tablet. In such examples, the therapeutic composition can typically include a binder. Non-limiting examples of binders can include lactose, calcium phosphate, sucrose, corn starch, microcrystalline cellulose, gelatin, polyethylene glycol (PEG), polyvinyl pyrrolidone (PVP), hydroxypropyl cellulose, hydroxyethylcellulose, carboxymethyl cellulose (CMC), the like, or combinations thereof.

Where the therapeutic composition is formulated as a tablet, in some examples the therapeutic composition can also include a disintegrant. Non-limiting examples of disintegrants can include crosslinked PVP, crosslinked CMC, modified starch, sodium starch glycolate, the like, or combinations thereof.

In some examples the tablet can also include a filler. Non-limiting examples of fillers can include lactose, dicalcium phosphate, sucrose, microcrystalline cellulose, the like, or combinations thereof.

In some further examples, the tablet can include a coating, such as an enteric coating or other suitable coating. Such coatings can be formed with a variety of materials, such as hydroxypropyl methylcellulose (HPMC), shellac, zein, various polysaccharides, various enterics, the like, or combinations thereof.

In some examples, the tablet can include a variety of other ingredients, such as anti-adherents (e.g. magnesium stearate, for example), colorants, glidants (e.g. fumed silica, talc, magnesium carbonate, for example), lubricants (e.g. talc, silica, magnesium stearate, stearic acid, for example) preservatives, desiccants, and/or other suitable tablet excipients, as desired.

In some other examples, the therapeutic composition can be formulated as a capsule. In such examples, the capsule itself can typically include gelatin, hypromellose, HPMC, CMC, the like, or combinations thereof. A variety of excipients can also be included within the capsule, such as binders, disintegrants, fillers, glidants, preservatives, coatings, the like, or combinations thereof, such as those listed above with respect to tablets, for example, or other suitable variations.

In some examples, the therapeutic composition can be formulated as a liquid oral dosage form. A liquid oral dosage form can include a variety of excipients, such as a liquid vehicle, a solubilizing agent, a thickener or dispersant, a preservative, a tonicity agent, a pH adjuster or buffering agent, a sweetener, the like, or a combination thereof. Non-limiting examples of liquid vehicles can include water, ethanol, glycerol, propylene glycol, the like, or combinations thereof. Non-limiting examples of solubilizing agents can include banzalkonium chloride, benzethonium chloride, cetylpyridinium chloride, docusate sodium, nonoxynol-9, octoxynol, polyoxyethylene polyoxypropylene co-polymers, polyoxyl castor oils, polyoxyl hydrogenated castor oils, polyoxyl oleyl ethers, polyoxyl cetylstearyl ethers, polyoxyl stearates, polysorbates, sodium lauryl sulfate, sorbitan monolaurate, sorbitan monooleate, sorbitan monopalmitate, sorbitan monostearate, tyloxapol, the like, or combinations thereof. Non-limiting examples of thickeners or dispersants can include sodium alginate, methylcellulose, hydroxyethylcellulose, hydroxypropylcellulose, HPMC, CMC, microcrystalline cellulose, tragacanth, xanthangum, bentonite, carrageenan, guar gum, colloidal silicon dioxide, the like, or combinations thereof. The preservative, tonicity agent, pH adjuster or buffering agent can typically be any of those described above with respect to the injectable formulations or other suitable preservative, tonicity agent, pH adjuster or buffering agent. Sweeteners can include natural and/or artificial sweeteners, such as sucrose, glucose, fructose, stevia, erythritol, xylitol, aspartame, sucralose, neotame, acesulfame potassium, saccharin, advantame, sorbitol, the like, or combinations thereof, for example.

In yet other examples, the pharmaceutically acceptable carrier can be formulated to provide a therapeutic composition for topical, transdermal, or transmucosal administration, such as to the skin, to the eye, to the vaginal cavity, to the rectum, to the nasal cavity, the like, or a combination thereof. Further, the topical, transdermal, or transmucosal formulations can be formulated for local and/or systemic delivery of one or more components of the therapeutic composition.

Where the therapeutic composition is formulated for topical, transdermal, or transmucosal administration, the pharmaceutically acceptable carrier can include a variety of components suitable for forming a suspension, dispersion, lotion, cream, ointment, gel, foam, patch, powder, paste, sponge, the like, or a combination thereof. Non-limiting examples can include a solubilizer, an emulsifier, a dispersant, a thickener, an emollient, a pH adjuster, a tonicity agent, a preservative, an adhesive, a penetration enhancer, the like, or a combination thereof. Non-limiting examples of solubilizers and/or emulsifiers can include water, ethanol, propylene glycol, ethylene glycol, glycerin, polyethylene glycol, banzalkonium chloride, benzethonium chloride, cetylpyridinium chloride, docusate sodium, nonoxynol-9, octoxynol, polyoxyethylene polyoxypropylene co-polymers, polyoxyl castor oils, polyoxyl hydrogenated castor oils, polyoxyl oleyl ethers, polyoxyl cetylstearyl ethers, polyoxyl stearates, polysorbates, sodium lauryl sulfate, sorbitan monolaurate, sorbitan monooleate, sorbitan monopalmitate, sorbitan monostearate, tyloxapol, the like, or combinations thereof. In some examples, the solubilizer can also include a hydrocarbon or fatty substance, such as petrolatum, microcrystalline wax, paraffin wax, mineral oil, ceresi, coconut oil, bees wax, olive oil, lanolin, peanut oil, spermaceti wax, sesame oil, almond oil, hydrogenated castor oils, cotton seed oil, soybean oil, corn oil, hydrogenated sulfated castor oils, cetyl alcohol, stearyl alcohol, oleyl alcohol, lauryl alcohol, myristyl alcohol, stearic acid, oleic acid, palmitic acid, lauraic acid, ethyl oleate, isopropyl myristicate, the like, or combinations thereof. In some examples, the solubilizer can include a silicon, such as polydimethylsiloxanes, methicones, dimethylpropylsiloxanes, methyl phenyl polysiloxanes, steryl esters of dimethyl polysiloxanes, ethoxylated dimethicones, ethoxylated methicones, the like, or combinations thereof.

In some additional examples, the therapeutic composition can include a dispersant and/or thickening agent, such as polyacrylic acids (e.g. Carbopols, for example), gelatin, pectin, tragacanth, methyl cellulose, hydroxylethylcellulose, hydroxypropylcellulose, HPMC, CMC, alginate, starch, polyvinyl alcohol, polyvinyl pyrrolidone, co-polymers of polyoxyethylene and polyoxypropylene, polyethylene glycol, the like, or combinations thereof.

In some examples, the therapeutic composition can include an emollient, such as aloe vera, lanolin, urea, petrolatum, shea butter, cocoa butter, mineral oil, paraffin, beeswax, squalene, jojoba oil, coconut oil, sesame oil, almond oil, cetyl alcohol, stearyl alcohol, olive oil, oleic acid, triethylhexanoin, glycerol, sorbitol, propylene glycol, cyclomethicone, dimethicone, the like, or combinations thereof.

In some examples, the therapeutic composition can include an adhesive, such as acrylic adhesives, polyisobutylene adhesives, silicon adhesives, hydrogel adhesives, the like, or combinations thereof.

In some examples, the therapeutic composition can include a penetration enhancer, such as ethanol, propylene glycol, oleic acid and other fatty acids, azone, terpenes, terpenoids, bile acids, isopropyl myristate and other fatty esters, dimethyl sulphoxides, N-methyl-2-pyrrolidone and other pyrrolidones, the like, or combinations thereof.

The pH adjusters, tonicity agents, and preservatives in the topical, transdermal, or transmucosal therapeutic composition can generally include those pH adjusters and buffering agents, tonicity agents, and preservative agents listed above, or any other suitable pH adjusters, buffering agent, tonicity agent, or preservative for a particular formulation and/or use thereof. In some examples, the therapeutic composition can also include fumed silica, mica, talc, titanium dioxide, kaolin, aluminum glycinate, ethylenediaminetetraacetic acid, fragrances, colorants, other components as described above, the like, or combinations thereof.

In some additional examples, the pharmaceutically acceptable carrier can be formulated for administration via inhalation. In some examples, such formulations can include a propellant, such as hydrofluoralkanes, such as HFA134a, HFA227, or other suitable propellant. In yet other examples, the therapeutic composition can be formulated for administration via nebulization. In either case, the therapeutic composition can also include a variety of solubilizing agents, such as those described above. In other examples, the therapeutic composition can be formulated as a dry powder aerosol. In some examples, the therapeutic composition can include a particulate carrier and/or other particulate excipients, such as lactose, mannitol, other crystalline sugars, fumed silica, magnesium stearate, amino acids, the like, or combinations thereof.

In some specific examples, the pharmaceutically acceptable carrier can be formulated to provide a therapeutic composition for ocular administration. Non-limiting examples can include topical application to the eye in the form of a drop, a gel, a film, an insert, a sponge, an ointment, the like, or a combination thereof. In yet other examples, the therapeutic composition can be formulated for intraocular injection or implantation in the form of a solution, a depot, a scaffold, the like, or a combination thereof. Ocular compositions can include a variety of excipients, such as water, a tonicity agent, a thickening agent, a biodegradable polymer, a solubilizing agent, an emulsifier, a preservative, the like, or other suitable component, or a combination thereof. In some examples, the ocular composition can include a biodegradable polymeric matrix that can include a variety of biodegradable constituents, such as polylactic acid, poly (lactic-co-glycolic) acid, polyglycolic acid, poly(caprolactone), hyaluronic acid, polyhydroxybutyrate, polyvinyl alcohol, polyvinylpyrrolidone, carbomers, polyacrylic acid, polyoxyethylene/polyoxypropylene copolymers, other copolymers, albumins, casein, zein, collagen, other proteins, glucose, sucrose, maltose, trehalose, amylose, dextrose, fructose, mannose, galactose, other sugars, erythritol, threitol, arabitol, xylitol, ribitol, mannitol, sorbitol, galactitol, fucitol, iditol, inositol, volemitol, isomalt, maltitol, lactitol, maltotriitol, maltotetraitol, polyglycitol, other sugar alcohols, chondroitin and/or other glycosaminoglycans, inulin, starches, acacia gum, agar, carboxymethyl cellulose, methyl cellulose, ethyl cellulose, alginates, carrageenan, cassia gums, cellulose gums, chitin, chitosan, curdlan, gelatin, dextran, fibrin, fulcelleran, gellan gum, ghatti gum, guar gum, tragacanth, karaya gum, locust bean gum, pectin, starch, tara gum, xanthan gum, and other polysaccharides, and functionalized derivatives of any of the above, copolymers thereof, the like, or mixtures thereof.

It is noted that a variety of components are listed for use in specific carriers or carrier types. However, the lists of components are not necessarily intended to be exclusive to a particular carrier or carrier type. For example, the biodegradable polymers specifically listed with reference to ocular formulations may also be useful in other carriers or carrier types as well. Thus, where suitable, any of the components disclosed herein can be employed in any pharmaceutically acceptable carrier whether or not the particular component is specifically listed with specific reference to a particular carrier type.

In some examples, the therapeutic compositions described herein can be disposed in a suitable container. Such containers can include multiple-use containers or single use containers. Non-limiting examples can include bottles, vials, blister packs, bags, or the like.

In some examples, the container can be an amber colored container or other suitable container configured to protect the dosage form or therapeutic composition from light. In yet other examples, the container can include instructions and dosing information for the dosage form or therapeutic composition. The container can include a variety of materials, such as polyethylene, polypropylene, polycarbonate, polyvinyl chloride, glass, the like, or a combination thereof.

Generally, the leaving group Z of the bioorthogonal molecule will remain covalently attached to the bioorthogonal molecule until the bioorthogonal molecule interacts with a releasing molecule, such as a tetrazine molecule. In some examples, the releasing molecule can have a structure according to Formula III or Formula IV:

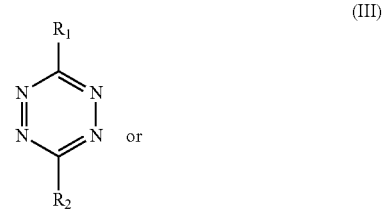

-continued

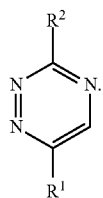
(IV)

With this in mind, in some examples, the therapeutic composition can include a releasing molecule, such as a tetrazine molecule, to react with the bioorthogonal molecule to release leaving group Z. Thus, in some examples, the bioorthogonal molecule and the releasing molecule can be included in the same composition and in the same container. Where this is the case, it may be desirable to minimize interaction between the bioorthogonal molecule and the releasing molecule prior to administration by adjusting the pH to minimize reactivity between the bioorthogonal molecule and the releasing molecule prior to administration, reducing solubility of the bioorthogonal molecule and/or the releasing molecule in the composition to minimize reactivity between the bioorthogonal molecule and the releasing molecule prior to administration, increasing the viscosity of the composition to minimize reactivity between the bioorthogonal molecule and the releasing molecule prior to administration, reducing the temperature of the composition to minimize reactivity between the bioorthogonal molecule and the releasing molecule prior to administration, the like, or a combination thereof. In some examples, mere administration can provide a suitable reaction environment for the bioorthogonal molecule and the releasing molecule. In other examples, adjustments can be made to the composition prior to administration to provide a suitable administration vehicle and/or reaction environment.

The present disclosure also describes a therapeutic system. The therapeutic system can include a therapeutic composition and a separate releasing composition. The therapeutic composition can include a bioorthogonal molecule as described herein and a pharmaceutically acceptable carrier, also as described herein. The releasing composition can include a releasing molecule and a second pharmaceutically acceptable carrier, as described herein.

In some examples, the therapeutic composition and the releasing composition can be disposed in separate containers. In some cases, this can prevent premature release of the therapeutic agent from the bioorthogonal molecule. In some examples, the therapeutic composition and the releasing composition can be mixed immediately prior to administration (e.g. within about 5 minutes, 10 minutes, 30 minutes, or 60 minutes). In other examples, the therapeutic composition and the releasing composition can be administered separately so that the individual compositions are not mixed prior to administration. It is noted that in some examples, the therapeutic composition and the releasing composition can have the same pharmaceutically acceptable carrier. In other examples, the therapeutic composition and the releasing composition can have distinct pharmaceutically acceptable carriers.

In some examples, the therapeutic composition and the releasing composition can be included in the same container. Where this the case, the common container may include a rupturable or otherwise removable membrane or barrier separating the therapeutic composition and the releasing composition. In some examples, the therapeutic composition and the releasing composition can be disposed in a syringe having a cork-screw mixer or the like to mix the therapeutic composition and the releasing composition as they are dispensed from the syringe. Other suitable arrangements of the therapeutic composition and the releasing composition in the common container can also be employed.

A variety of releasing molecules can be used in the releasing composition. Generally, any suitable tetrazine-based molecule can be used or other suitable compound for releasing the payload from the bioorthogonal molecule. In some specific examples, the releasing molecule can have a structure according to Formula III:

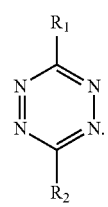
(III)

In some additional examples, the releasing molecule can have a structure according to Formula IV:

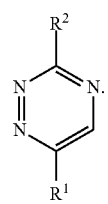
(IV)

The therapeutic compositions or therapeutic systems can be employed in a variety of treatment regimens or dosing regimens. For example, in some cases, the therapeutically effective amount can be administered via a single dose and/or a dosage regimen. In some examples, the dosage regimen can include administering the therapeutic composition at a suitable frequency. In some examples, the dosage regimen can include administering the therapeutic composition from 1 time per day to 12 times per day or more in individual doses. In some further examples, the dosage regimen can include administering the therapeutic composition from 1 time per day to 2, 3, 4, or 6 times per day in individual doses. In yet other examples, the therapeutic composition can be administered via infusion, or other equivalent process. Where this is the case, in some examples, the composition can be administered over a period of from about 30 minutes or 1 hour to about 6 hours or 12 hours or more. Further, depending on the adverse health condition, administration of the therapeutic composition can be performed over a period of from 1 day to 365 days or more, over a period from 1 day to 30 days, over a period of 7 days to 90 days, over a period of 1 month to 6 months, 12 months, 18 months, or 24 months, or other suitable treatment period at any suitable frequency, such as those described above, or other suitable frequency, such as once per week, twice per week, three times per week, once every two weeks, once per month, once every six weeks, once every two months, etc.

The bioorthogonal molecules described herein can have a variety of uses and can be employed in a variety of methods. For example, in some cases, the bioorthogonal molecule can be used as a protecting group that can be removed under mild conditions, including in biological samples and in vivo. This can be done in a variety of ways. For example, the structure of a target molecule can be temporarily modified with a reactive precursor of the bioorthogonal molecule, followed by subsequent removal of the bioorthogonal molecule from the target molecule by contact with a releasing molecule. In another example, the bioorthogonal molecule can be incorporated onto a target molecule during its synthesis, followed by subsequent removal of the bioorthogonal molecule from the target molecule by contact with a releasing molecule In some examples, a target molecule can be inactivated by derivatization with the bioorthogonal molecule, such that upon reaction with suitable molecules, such as a releasing molecule, the target molecule is reactivated by loss of the bioorthogonal molecule. In some examples, the bioorthogonal molecule can be attached to the modified target molecule via an immolative tether.

In some examples, polypeptides (e.g. proteins) or derivatives thereof can be modified at one or several of: amino-acid side chains (e.g. —NH$_2$ of Lys; —OH of Ser, Thr, Tyr; —SH of Cys), the amino- or carboxy-terminus, at modified side chains (e.g. phosphorylated Ser, Thr, Tyr), or at artificial amino acids part of the polypeptide sequence with the bioorthogonal molecule (e.g. BNBD), as illustrated in FIG. 1A. Specifically, FIG. 1A illustrates a target molecule 104 that has been reversibly modified with a bioorthogonal molecule (e.g. BNBD). While specific reference will be made to polypeptides with respect to FIGS. 1A-1C, the modified target molecule 104 can represent a variety of target molecules, such as a polypeptide, a carbohydrate, a lipid, a nucleic acid, or the like. The bioorthogonal molecule can be released from the modified target molecule 104 (e.g. a polypeptide) by interaction with a releasing group (e.g. tetrazine, for example).

Figure 1B:
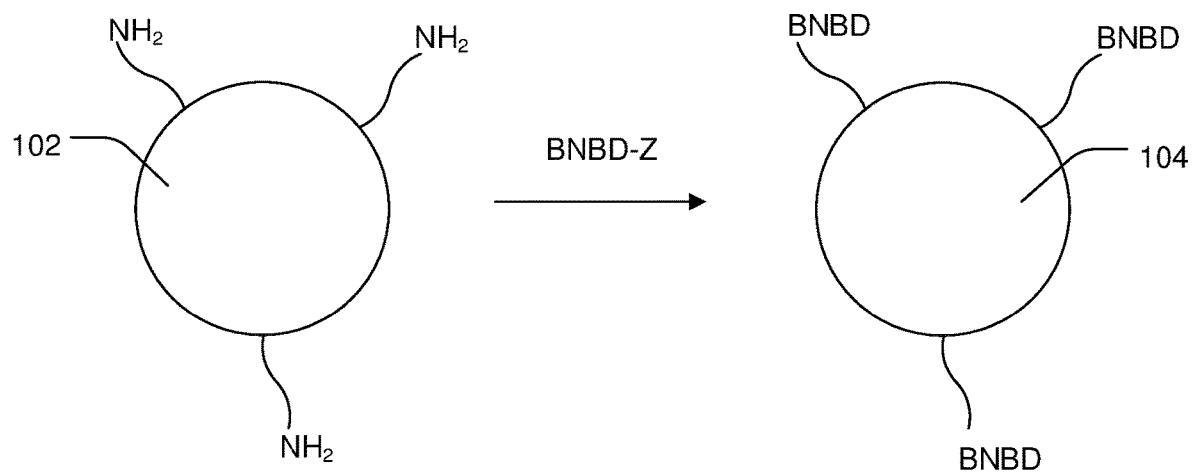
FIG. 1B illustrates a method of making a modified target molecule, in accordance with an example of the present disclosure.

Such modified target molecules can be prepared in a variety of ways. For example, as illustrated in FIG. 1B, a bioorthogonal molecule precursor (BNBD-Z), having a suitable leaving group, can be reacted with a suitable target molecule 102. This can removably couple the bioorthogonal molecule (e.g. BNBD) to the target molecule 102 to provide a modified target molecule 104. Suitable modified polypeptides and other suitable target molecules can also be prepared by expanded-genetic code methods or by adding the bioorthogonal molecule to the target molecule during the synthesis of the target molecule.

In some additional examples, modified polypeptides can be prepared by linking two precursor polypeptides (e.g. native chemical ligation, intein ligation), at least one of which is modified with the bioorthogonal molecule. The bioorthogonal molecules can also be used to perform enzymatic labeling substrates containing the bioorthogonal molecule.

Figure 1C:
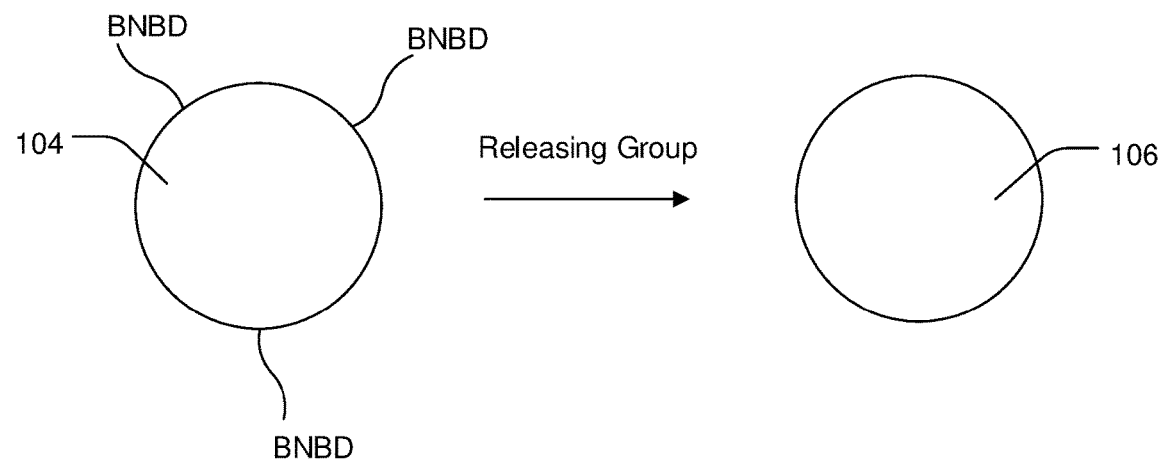
FIG. 1C illustrates a method of reconstituting a modified target molecule, in accordance with an example of the present disclosure.

In some examples, a polypeptide can be reconstituted by contact with suitable bioorthogonal molecules (e.g. BNBD), followed by removal by reaction with a suitable releasing group (e.g. Tz) as illustrated in FIG. 1C. In this example, modified target molecule 104 can be reacted with a releasing group to produce a reconstituted polypeptide 106.

Figure 2:
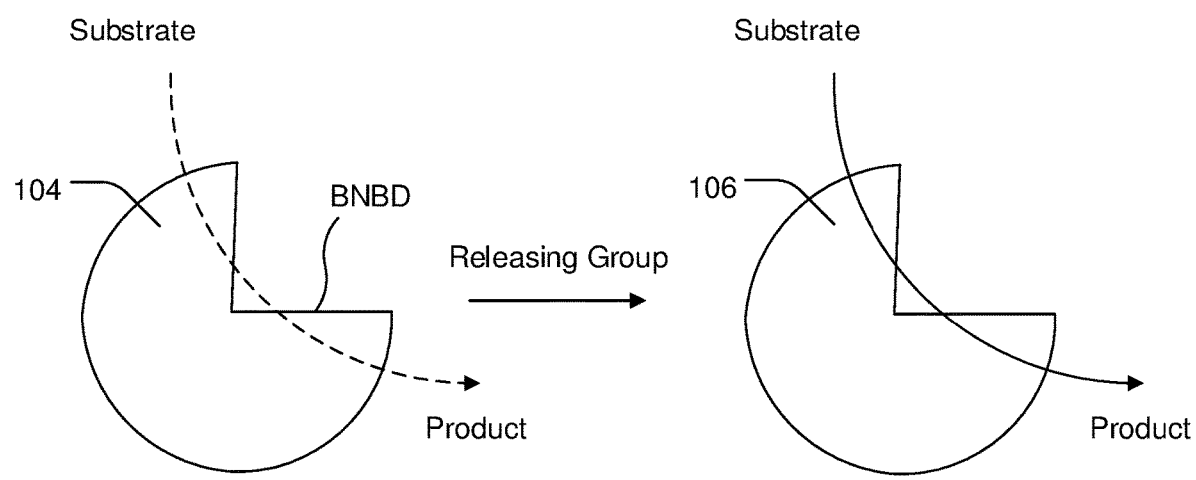
FIG. 2 illustrates a method of activating an inactive enzyme, in accordance with an example of the present disclosure.

In still additional examples, the activity of an enzyme can be controllably reconstituted by contacting and subsequently dissociating a suitable bioorthogonal molecule from the enzyme using a releasing group, as illustrated in FIG. 2. Specifically, the enzyme 104 can be modified by removably coupling a bioorthogonal molecule at any position that inactivates its function. The bioorthogonal molecule can be subsequently released from the inactive enzyme 104 using the releasing group to produce an active enzyme 106 having reconstituted activity.

In some further examples, the controlled reconstitution of enzyme activity can be associated with the generation of an analytic signal (e.g. fluorescence, bioluminescence, chemiluminescence, colorimetric, etc.). In additional examples, the controlled reconstitution of enzyme activity can be associated with the generation of a therapeutic agent. In still additional examples, the controlled reconstitution of enzyme activity can be associated with the activation of cytotoxic enzyme activity (e.g. enzyme toxins).

In some examples, a bioorthogonal molecule can be used to spatially and/or temporally control the activation of an enzyme. For example, a modified enzyme (i.e. modified with a bioorthogonal molecule) can be delivered to a specific location (e.g. tissue, tumor), followed by release of the bioorthogonal molecule via a releasing molecule and associated activation of the enzyme. In some further examples, enzyme activation can be followed by subsequent activation of prodrugs, activatable reporter groups, or can be associated with a therapeutic or cytotoxic effect.

Figure 3:
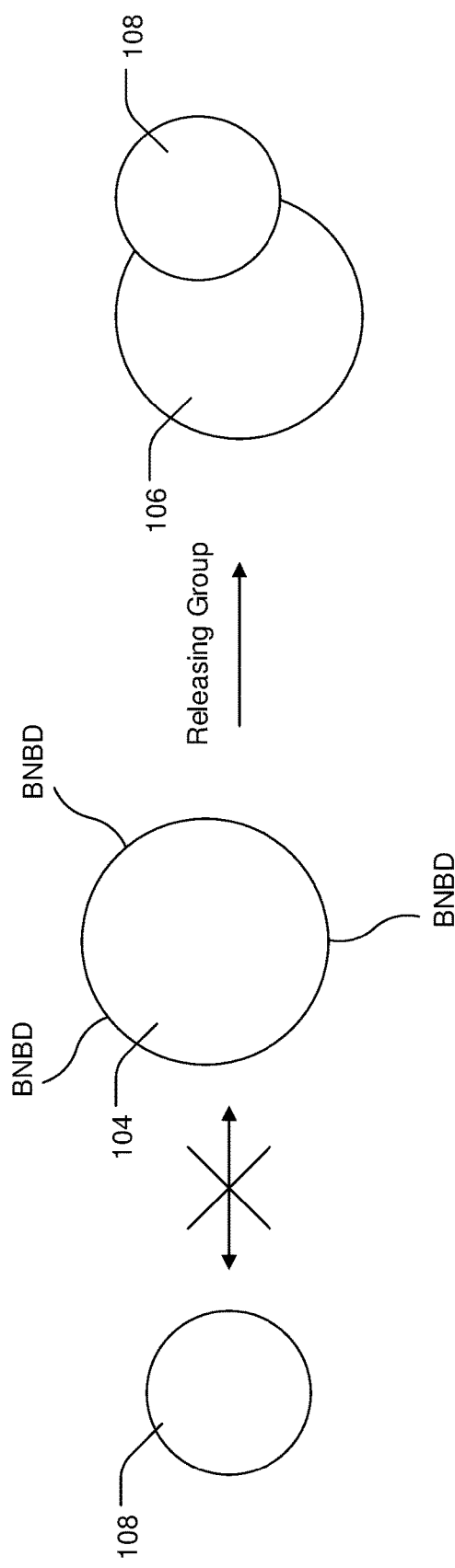
FIG. 3 illustrates a method of controlling interactions between a target molecule and another molecule, in accordance with an example of the present disclosure.

In still additional examples, the bioorthogonal molecules can be used in methods for the controlled release of a polypeptide for interactions with other biomolecules (e.g. proteins, nucleic acids, etc.), as illustrated in FIG. 3, for example. Specifically, polypeptide 104 can be modified by removably coupling a bioorthogonal molecule (e.g. BNBD) thereto to prevent interaction with biomolecule 108. When interaction with biomolecule 108 is desired, the bioorthogonal molecule can be removed via reaction with a releasing group to prepare reconstituted polypeptide 106 having restored interaction with biomolecule 108.

Bioorthogonal molecules can also be used in methods for controlled drug delivery. For example, a modified polypeptide can be delivered to a specific location (e.g. tissue, tumor) followed by activation of the polypeptide by release of the bioorthogonal molecule with a suitable releasing molecule. In some examples, the activated protein can be a cytokine, chemokine, enzyme hormone, protein toxin, the like, or a combination thereof.

Figure 4:
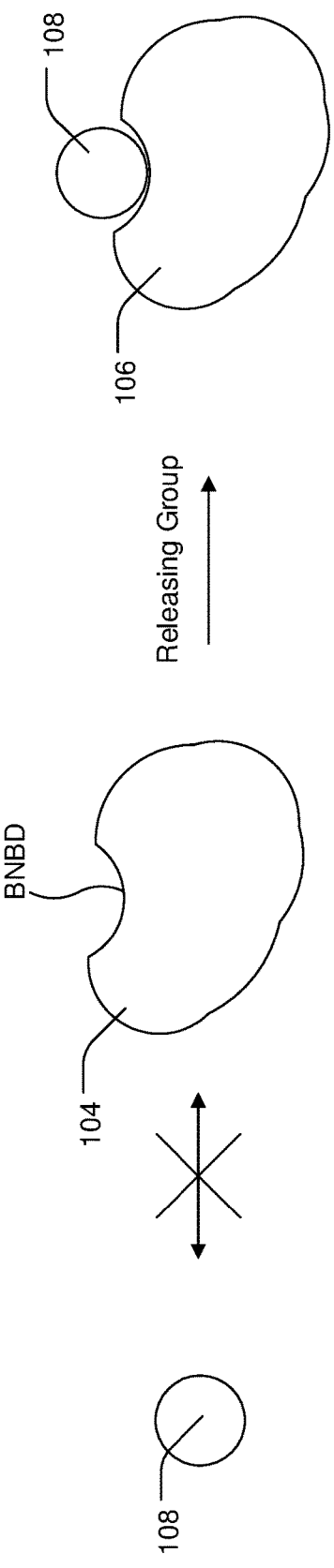
FIG. 4 illustrates another method of controlling interactions between a target molecule and another molecule, in accordance with an example of the present disclosure.

In additional examples, bioorthogonal molecules can be used in methods for the controlled release of a polypeptide therapeutic (e.g. cytokine, chemokine, peptide hormone, protein toxin). In yet other examples, bioorthogonal molecules can be used in methods for the controlled release of a polypeptide (e.g. receptor) for interacting with small molecules, as illustrated in FIG. 4. Specifically, a small-molecule binding pocket of modified polypeptide 104 can be blocked to removably coupling a bioorthogonal molecule at or near the binding pocket. This can prevent interaction of the protein ligand 108 with the polypeptide. When interaction is desired, a removing molecule can be introduced to remove the bioorthogonal molecule to produce a reconstituted polypeptide 106 having restored protein ligand 108 binding.

In some examples, molecules including oligonucleotides (e.g. DNA, RNA) or derivatives thereof (e.g. PNA, LNA, 2'-OMe-RNA, phosphorothioates) can be modified at nucleobases, the termini, and/or the backbone with one or more bioorthogonal molecules (e.g. BNBD). For example, bioorthogonal molecules can be directly attached to the specified residues or via immolative spacers. As illustrated in FIG. 5A, nucleic acid 110 can have bioorthogonal molecules attached at select nucleobases 112, on the backbone 114, or both, as desired. The following structures represent some examples of attachment points for the bioorthogonal molecule to a nucleic acid. For example, in some cases, the bioorthogonal molecule can be attached directly to the specific nucleobase as follows:

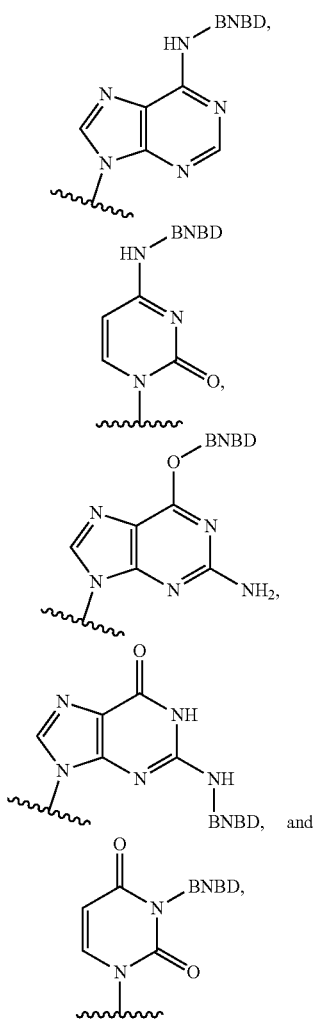

for example. In other examples, the bioorthogonal molecule can be attached to the nucleic acid at the backbone, such as in the following structure:

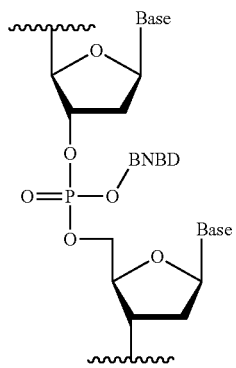

Regardless of the particular attachment point for the bioorthogonal molecules to the nucleic acid, the bioorthogonal molecules can be used in a variety of methods employing nucleic acids. For example, in some cases, the bioorthogonal molecules can be used in methods to reconstitute the structure of an oligonucleotide or a polynucleotide by contacting the bioorthogonal molecule with a releasing molecule to release the underlying oligonucleotide. One such example is illustrated in FIG. 5B. Specifically, a variety of bioorthogonal molecules are attached to a nucleic acid (e.g. an oligonucleotide or a polynucleotide) to form a modified nucleic acid 110. As desired, the bioorthogonal molecule can be reacted with a releasing group to produce a reconstituted nucleic acid 116.

The bioorthogonal molecules can also be used in methods to control the hybridization of oligonucleotides or polynucleotides via removal of bioorthogonal molecule modifications using a releasing molecule to release the target nucleic acid. One specific example of this is illustrated in FIG. 5C. Specifically, a target nucleic acid 111 can be prevented from hybridizing with modified nucleic acid probe 110 due to the removable coupling of a bioorthogonal molecule to the nucleic acid probe 110. Reaction with a releasing group can remove the bioorthogonal molecule from nucleic acid probe 110 to allow hybridization and to prepare a reconstituted nucleic acid 118.

Similarly, the bioorthogonal molecules can also be used in methods to control the folding of oligonucleotides or polypeptides by removal of bioorthogonal molecule modifications by reaction with a releasing molecule. For example, as illustrated in FIG. 5D, modified nucleic acid 110 can be prevented from folding due to the presence of bioorthogonal molecules removably coupled thereto. Reaction with a releasing group can remove the bioorthogonal molecules from the nucleic acid 110 to allow proper folding of the nucleic acid and preparation of a reconstituted nucleic acid 118. In some examples, the nucleic acid (e.g. an oligonucleotide) can be an aptamer or ribozyme.

Figure 5E:
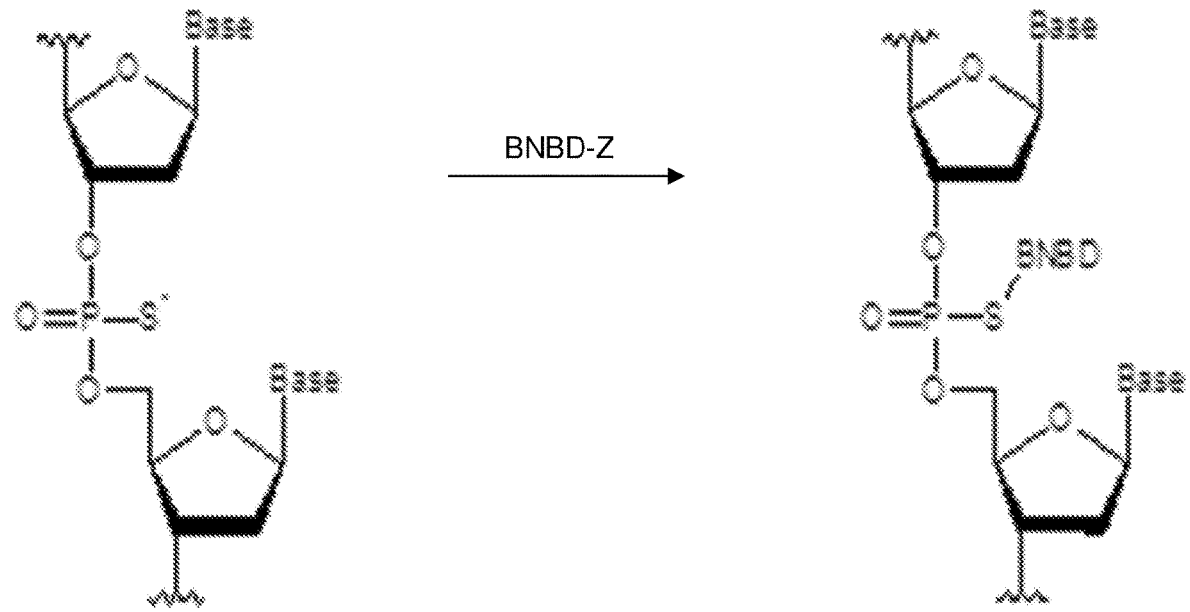
FIG. 5E illustrates a method of modifying a nucleic acid, in accordance with an example of the present disclosure.

In some examples, the bioorthogonal molecules can be used in methods for the synthesis of BNBD-modified oligonucleotides by reacting phosphorothioates with bioorthogonal molecules having a suitable leaving group (e.g. BNBD-Z, where Z is suitable leaving group.) On example of such a reaction is illustrated in FIG. 5E. In some other examples, the bioorthogonal molecules can be used in methods for the synthesis of modified oligonucleotides by incorporation of modified nucleotide derivatives during oligonucleotide solid phase synthesis. In some examples, the bioorthogonal molecules can be precursors for the solid-phase synthesis of modified oligonucleotides (for example by phosphite or phosphoramidite method). In some examples, the precursors can also be modified on the nucleobase. One non-limiting examples is depicted below for illustrative purposes only.

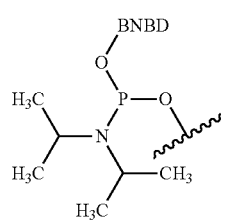

Figure 5F:
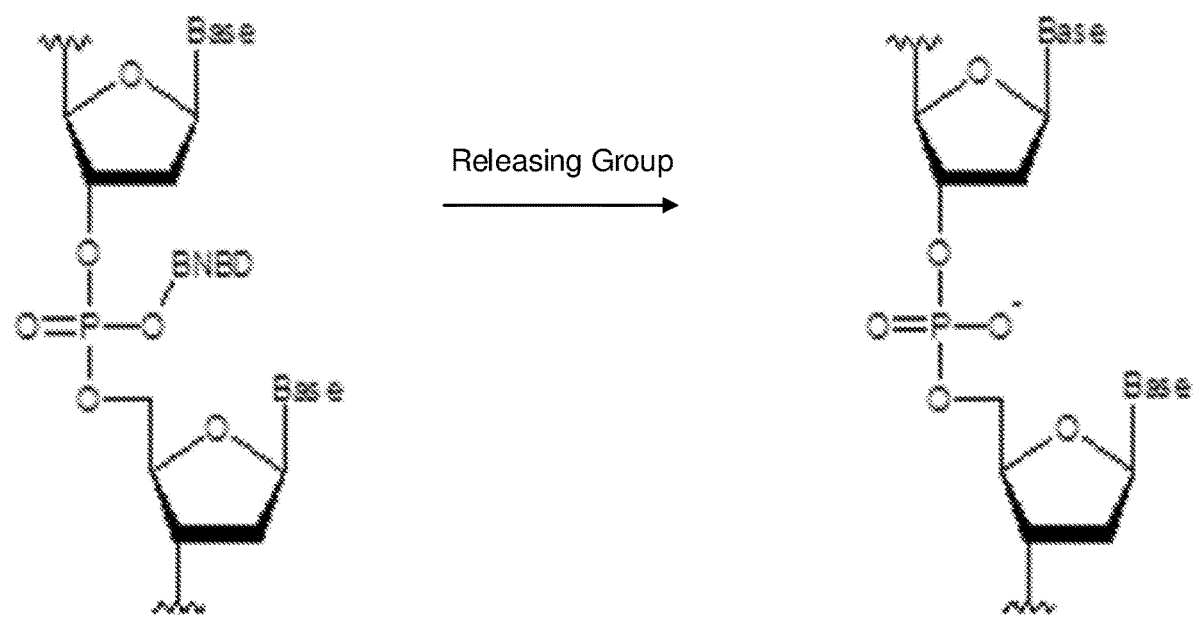
FIG. 5F illustrates a method of reconstituting a modified nucleic acid, in accordance with an example of the present disclosure.

Additionally, the bioorthogonal molecules can also be used in methods that remove bioorthogonal molecule modifications from oligonucleotide backbones by reaction with a releasing molecule. In some examples, the backbone can have a phosphate or phosphorothioate structure. One example of such a reaction is illustrated in FIG. 5F. In some specific examples, the bioorthogonal molecules can be used in methods for the removal of a bioorthogonal molecule from an oligonucleotide terminus by reaction with a suitable releasing molecule. In some examples, a method can include multiple cycles of incorporating a nucleotide containing a modification of the bioorthogonal molecule and removal of the bioorthogonal molecule by contact with a suitable releasing molecule.

Figure 5G:
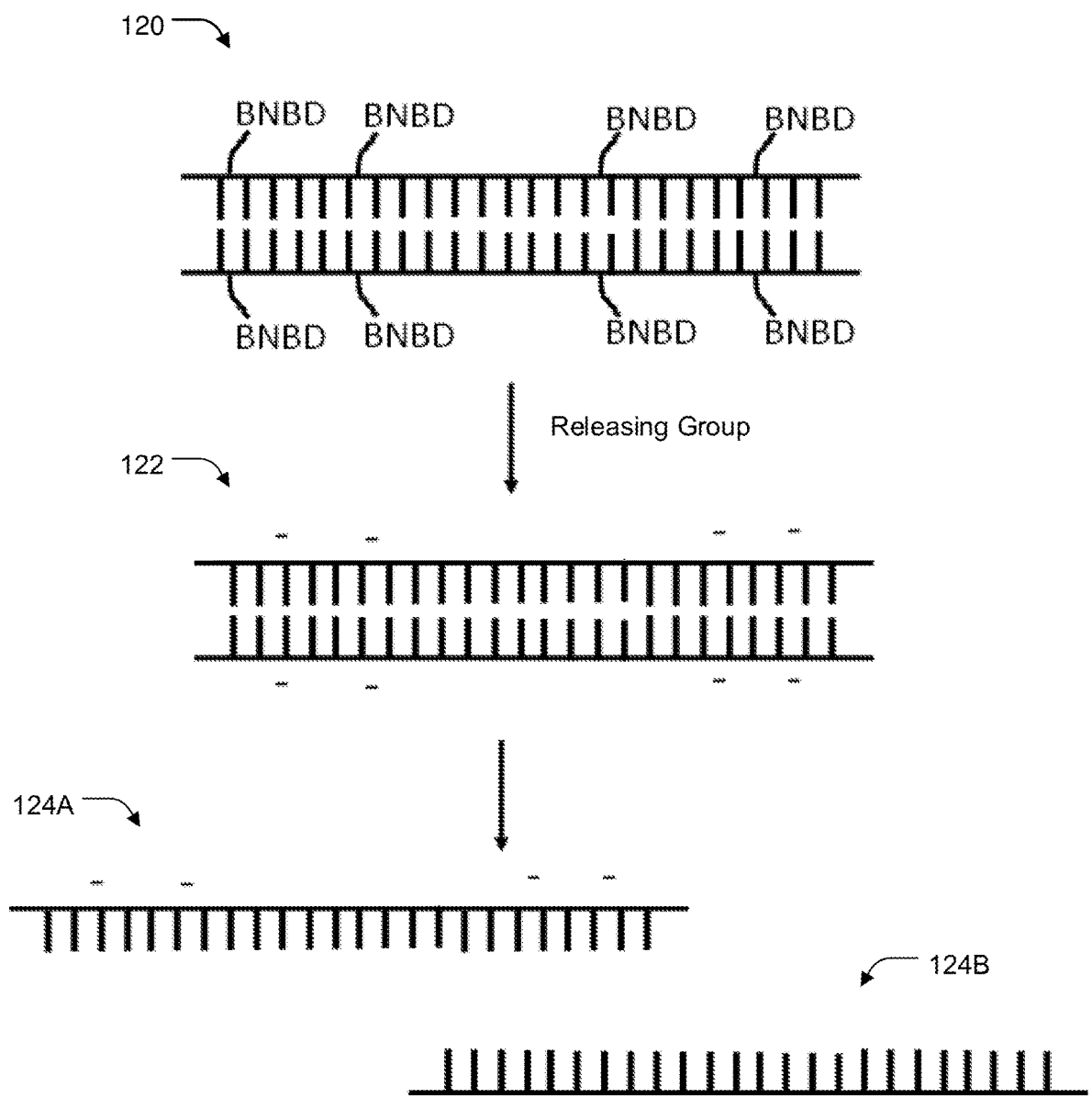
FIG. 5G illustrates a method of facilitating dissociation of nucleic acids, in accordance with an example of the present disclosure.

In some examples, the bioorthogonal molecules can be used in methods that control the dissociation of oligonucleotides by removal of one or more bioorthogonal molecule modifications from the backbone, as illustrated in FIG. 5G, for example. Specifically, modified nucleic acid 120 can include bioorthogonal molecule modifications that stabilize the modified nucleic acid 120 or otherwise prevent the dissociation of the individual nucleic acid strands. Reaction with a releasing group can remove the bioorthogonal molecule modifications from the modified nucleic acid 120 to prepare a nucleic acid 122 that is less stable or otherwise prone to dissociation. The nucleic acid 122 can dissociate into separate nucleic acid strands 124A, 124B.

In some additional examples, the bioorthogonal molecules can be used in methods for cell delivery of oligonucleotides and intracellular activation of oligonucleotides. The methods can include modifying an oligonucleotide with the bioorthogonal molecule to make it permeable to a membrane that is otherwise impermeable to the free oligonucleotide (e.g. cell membrane) followed by removal of the modifications by contact with a releasing molecule, causing the retention of the oligonucleotide within the compartment formed by the impermeable membrane (e.g. cell).

In some examples, the bioorthogonal molecules can be used in methods to elucidate the composition of an oligonucleotide molecule (e.g. DNA sequencing) by sequential incorporation of one or several nucleotides resulting in the modification of one of the termini (such as the 3' terminus, for example) with a bioorthogonal molecule, a reading step, and removal of the modification.

In some examples, the bioorthogonal molecule can include a precursor for the enzymatic incorporation of modified nucleotides into an oligonucleotide sequence. The bioorthogonal molecule modification can be linked to the oligonucleotide directly or via a immolative linker. In some examples, the precursor molecules can be modified at any position of the nucleobase or carbohydrate, for example.

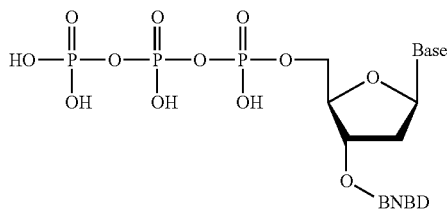

Figure 6A:
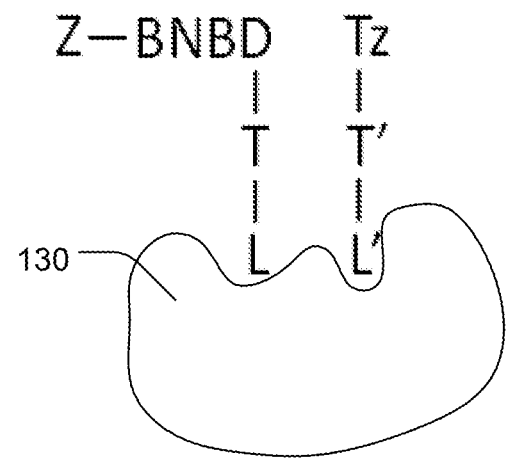
FIG. 6A illustrates a bioorthogonal molecule and a releasing molecule proximately bound to a target molecule, in accordance with an example of the present disclosure.
Figure 7A:
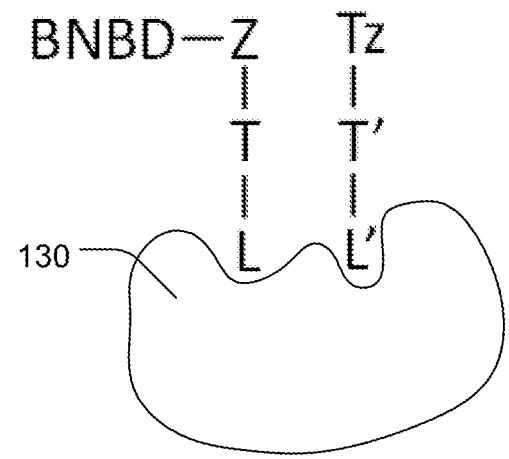
FIG. 7A illustrates a bioorthogonal molecule and a releasing molecule proximately bound to a target molecule, in accordance with an example of the present disclosure.

In some examples, the bioorthogonal molecule (sometimes referred to herein as BNBD) can have a structure that includes a targeting moiety (abbreviated L), a tether (abbreviated as T), and a leaving group (abbreviated as Z), such as L-T-BNBD-Z or L-T-Z-BNBD, for example. The targeting moiety can be but is not restricted to small-molecules, polypeptides, oligonucleotides, polymers, liposomes, micelles, or the like. In some examples, the releasing molecule (abbreviated Tz) can include a targeting moiety (abbreviated L) and a tether (abbreviated as T), such as L-T-Tz, for example. In some examples, compositions can include a bioorthogonal molecule and a releasing molecule, in which the targeting moieties L and L' bind to proximal sites of a common target. For example, FIG. 6A illustrates a bioorthogonal molecule L-T-BNBD-Z bound to a first site of a target molecule 130 and a releasing molecule L'-T'-Tz bound to a site proximal to the first site. FIG. 7A illustrates another example of a bioorthogonal molecule L-T-Z-BNBD bound to a first site of a target molecule 130 and a releasing molecule L'-T'-Tz bound to a site proximal to the first site.

It is noted that the various combinations of targeting moieties and target molecules are not particularly limited, and that any suitable targeting moiety, target molecule, or combinations thereof can be employed. In some specific examples, L and L' can be small molecules and the target molecule can be a polypeptide (including multimeric proteins and protein complexes). In additional examples, L and L' can be oligonucleotides (e.g. aptamers) and the target molecule can be a polypeptide (including multimeric proteins and protein complexes). In still additional examples, L and L' can be polypeptides and the target molecule can be a polypeptide (including multimeric proteins and protein complexes). In some specific examples, L and L' can be antibodies or fragments thereof.

Similarly, the leaving group Z is also not particularly limited and any suitable leaving group can be employed. In some specific examples, Z can be a reporter group (e.g. fluorophore, chemiluminophore, bioluminophore, radionuclide), affinity binder (e.g. hapten, biotin), a therapeutic agent, or the like.

Figure 6B:
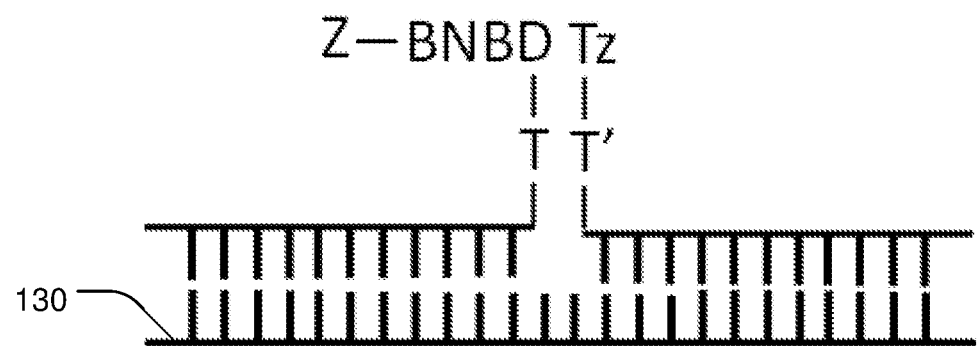
FIG. 6B illustrates a bioorthogonal molecule and a releasing molecule proximately bound to a target nucleic acid, in accordance with an example of the present disclosure.
Figure 7B:
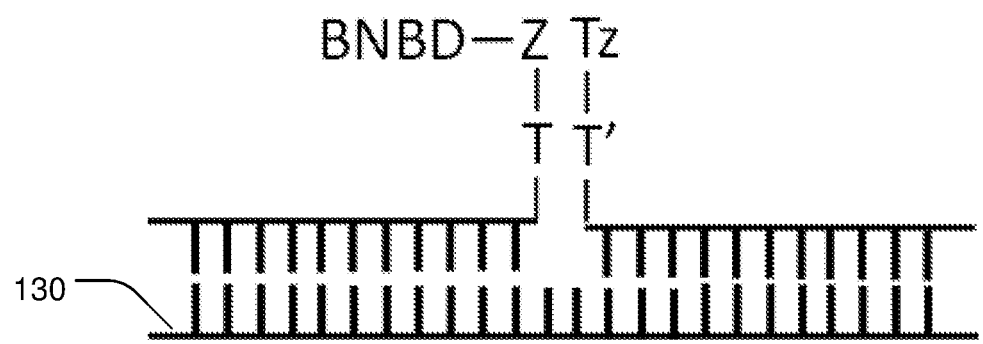
FIG. 7B illustrates a bioorthogonal molecule and a releasing molecule proximately bound to a target nucleic acid, in accordance with an example of the present disclosure.

In some examples, compositions can include both a bioorthogonal molecule and a releasing molecule in which L and L' are oligonucleotides and the target is a nucleic acid. For example, as illustrated in FIGS. 6B and 7B, both the bioorthogonal molecule and the releasing molecule can include a oligonucleotide targeting moieties that can hybridize to or otherwise bind to a common target nucleic acid molecule.

In some examples, as illustrated below, compositions can include a bioorthogonal molecule (abbreviated as BNBD-Z or Z-BNBD), a tether (abbreviated as T), a releasing group (abbreviated as Tz), and a moiety with affinity to each other (abbreviated as C):

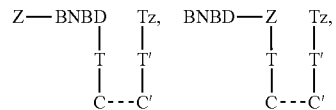

or the like. The interaction between C and C' can be any suitable interaction. In some specific examples, the interaction between C and C' can be a covalent interaction. In other examples, the interaction between C and C' can be a non-covalent interaction.

Figure 6C:
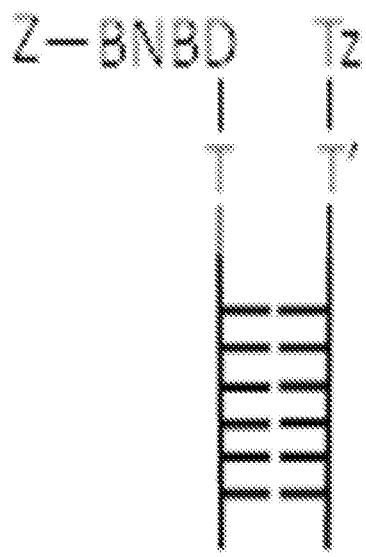
FIG. 6C illustrates a bioorthogonal molecule and a releasing molecule having hybridized targeting moieties, in accordance with an example of the present disclosure.
Figure 6D:
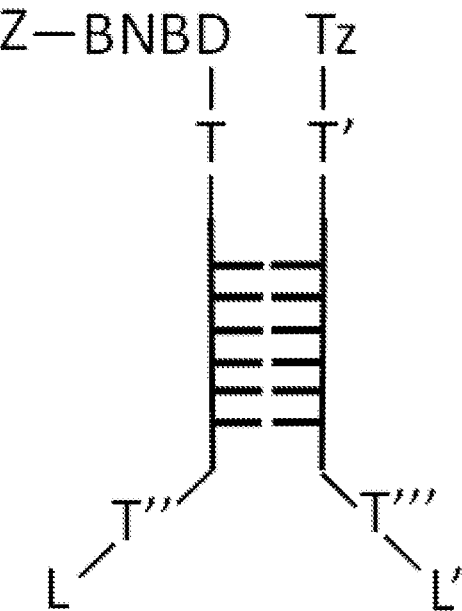
FIG. 6D illustrates another bioorthogonal molecule and a releasing molecule having hybridized targeting moieties, in accordance with an example of the present disclosure.
Figure 7C:
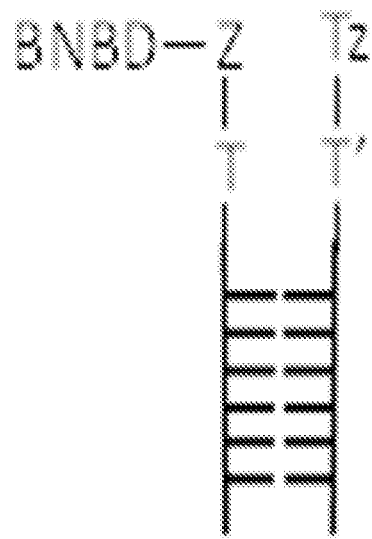
FIG. 7C illustrates a bioorthogonal molecule and a releasing molecule having hybridized targeting moieties, in accordance with an example of the present disclosure.
Figure 7D:
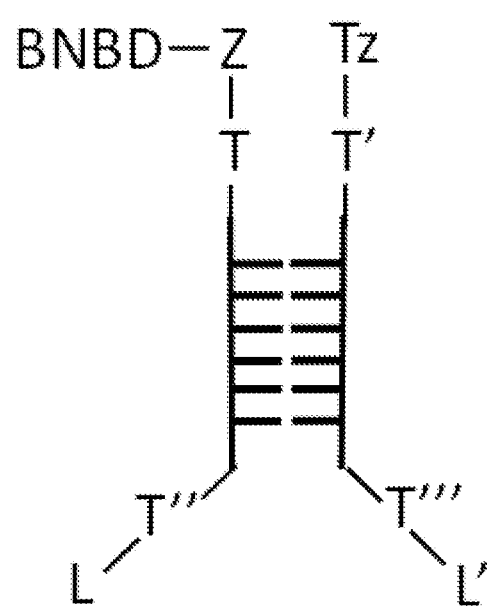
FIG. 7D illustrates another bioorthogonal molecule and a releasing molecule having hybridized targeting moieties, in accordance with an example of the present disclosure.

In some examples, C and C' can be oligonucleotides. Some non-limiting examples of such structures are illustrated in FIGS. 6C and 7C. In some examples, where C and C' are oligonucleotides, the oligonucleotides can be modified with targeting molecules (abbreviated as L) and can further include tethers (abbreviated T). Non-limiting examples of such structures are illustrated in FIGS. 6D and 7D. However, it is noted that the various elements of the bioorthogonal molecule and releasing molecule can be arranged in any suitable configuration.

Figure 6E:
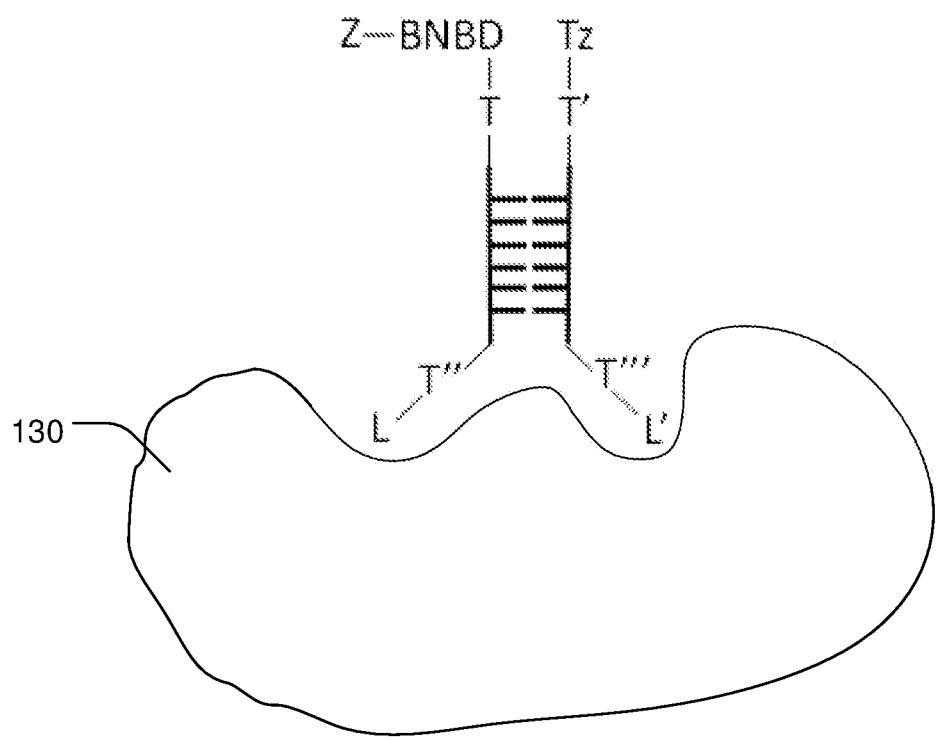
FIG. 6E illustrates a bioorthogonal molecule and a releasing molecule proximately bound to a target molecule, in accordance with an example of the present disclosure.
Figure 7E:
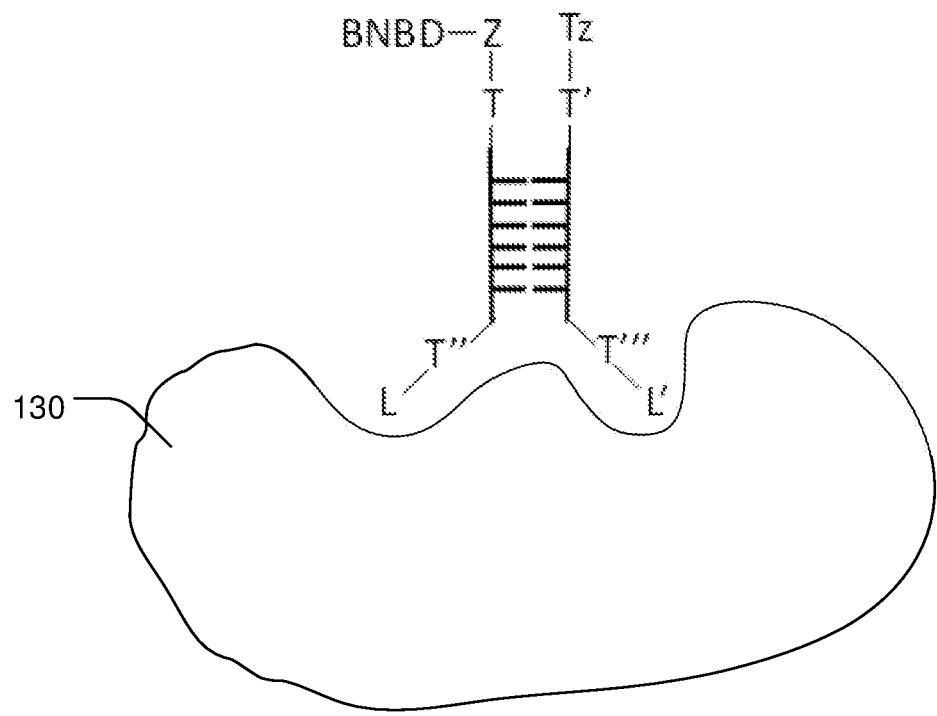
FIG. 7E illustrates a bioorthogonal molecule and a releasing molecule proximately bound to a target molecule, in accordance with an example of the present disclosure.

In some additional examples, the targeting moieties can bind to proximal sites on an analyte molecule or target molecule (e.g. biomacromolecules). For example, FIGS. 6E and 7E each illustrate different arrangements of bioorthogonal molecules bound to proximal sites on a target molecule 130.

In some specific examples, L and L' can be small molecules and the target molecule can be a polypeptide (including multimeric proteins and protein complexes). In some examples, L and L' can be oligonucleotides (e.g. aptamers) and the target molecule can be a polypeptide (including multimeric proteins and protein complexes). In yet additional examples, L and L' can be polypeptides and the target molecule can be a polypeptide (including multimeric proteins and protein complexes). In still additional examples, L and L' can be antibodies or fragments thereof.

In some additional examples, Z can be a reporter group (e.g. fluorophore, chemiluminophore, bioluminophore, radionuclide), affinity binder (e.g. hapten, biotin), therapeutic agent, or the like.

The bioorthogonal molecules can also be used in methods for the detection of an analyte (such as a biomacromolecule, for example) where a reporter signal can be amplified by repeated contacting of the bioorthogonal molecules with the target molecule, proximity-accelerated reaction of the molecules, release of Z, and dissociation of the molecules.

In some examples, the bioorthogonal molecules can be used in methods for the detection of an analyte (such as a biomacromolecule, for example) where the release of Z is linked to a reporter signal (e.g. fluorescence turn-on, activation of MRI contrast agent, chemiluminescence signal, bioluminescence signal). In some examples, the bioorthogonal molecule and target molecule can include a quencher/fluorophore pair.

Figure 6F:
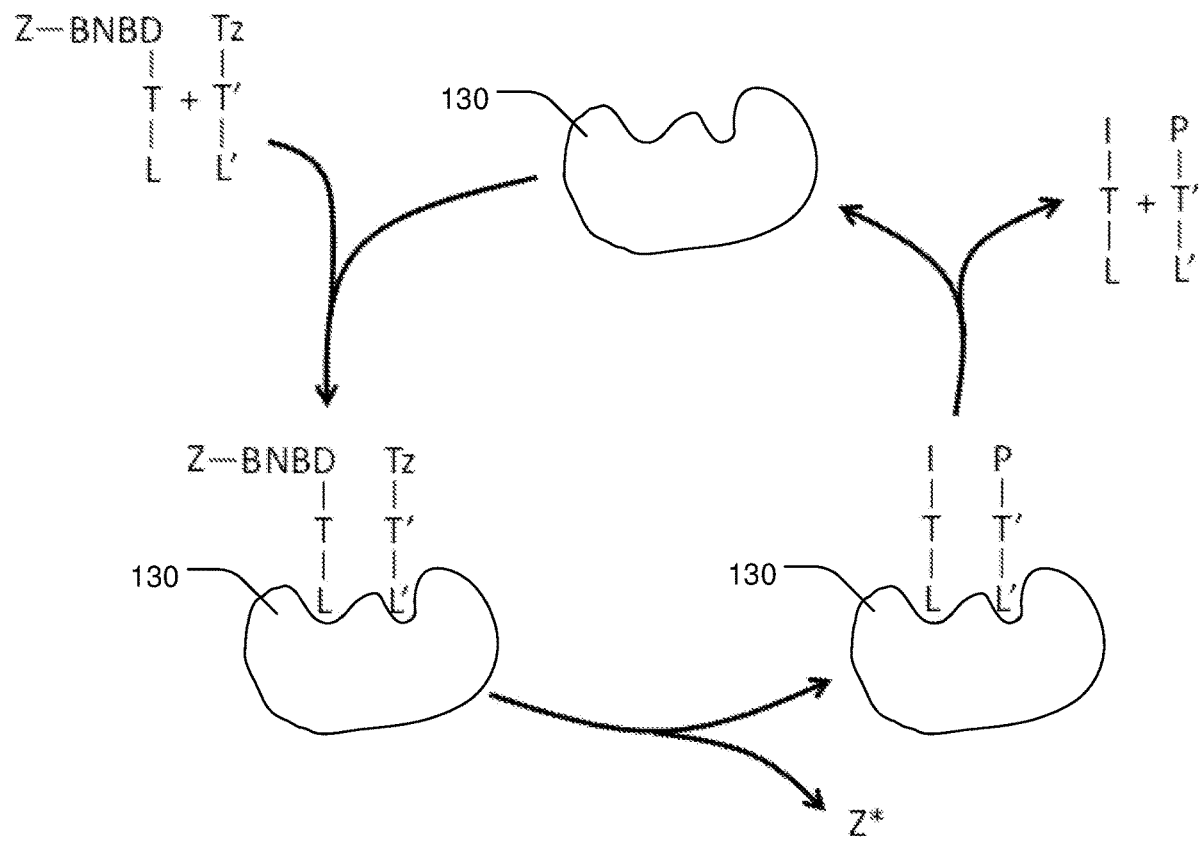
FIG. 6F illustrates a method of releasing a leaving group from a bioorthogonal molecule, in accordance with an example of the present disclosure.

In some examples, the bioorthogonal molecule can be used in methods for the detection of an analyte (such as a biomacromolecule, for example) where the reporter signal is amplified by repeated contacting of the bioorthogonal molecule with the target molecule, proximity-accelerated reaction of the molecules, release of Z, and dissociation of the molecules. One example of this is illustrated in FIG. 6F. Specifically, bioorthogonal molecule (L-T-BNBD-Z) and releasing molecule (L'-T'-Tz) can bind to target analyte 130 at proximal binding sites. This can facilitate proximity-accelerated reaction of the bioorthogonal molecule and the releasing molecule, resulting in the release of Z (reported molecule) and the subsequent dissociation of the side products (L-T-I and L'-T'-P) from the target analyte 130.

In some examples, the target molecule can be a biomarker. In some examples, the bioorthogonal molecules can be used in methods for delivering or localizing a therapeutic agent or reporter molecule in which a homing molecule that binds to a biomarker is modified with a template molecule that can be targeted by compositions as described herein. In some examples, the template molecule can be an oligonucleotide.

In some examples, the bioorthogonal molecules can be used in methods for delivering or localizing a therapeutic agent or reporter molecule in which proximal binding of two homing molecules reveal a template molecule that can be targeted by compositions as described herein.

In some examples, the bioorthogonal molecules can be used in methods of spatiotemporally controlled release of therapeutics or imaging agents in which compositions described herein are co-administered simultaneously or sequentially with a time-delay by any means of administration (e.g. topical, orally, intravenously, intramuscularly).

In some examples, the bioorthogonal molecules can be used in methods of spatiotemporally controlled release of therapeutics or imaging agents in which compositions described herein can accumulate at specific locations such as but not restricted to a specific tissue (e.g. tumor) or organ (e.g. bladder, kidney, liver).

In some examples, the bioorthogonal molecules can be used in methods of delivering molecules into a cell or other objects (e.g. organelle, epidermis) with a partially permeable membrane, in which the molecule of interest is modified with moieties of the bioorthogonal molecule to be permeable to the membrane (e.g. plasma membrane). In a subsequent step, contact with releasing molecules can remove the bioorthogonal molecules, which can cause retention of the molecules of interest within the enclosed space of the membrane (i.e. cell) because of reduced membrane permeability.

In some examples, compositions can include the bioorthogonal molecule and/or the releasing molecule in which the molecules are modified with moieties that lead to preferred accumulation at specific locations such as but not restricted to a specific tissue (e.g. tumor) or organ (e.g. bladder, kidney, liver).

In some examples, compositions can include the bioorthogonal molecule and/or the releasing molecule in which the molecules are modified with moieties that improve the pharmacokinetic properties and reaction with the releasing molecule as a method for slow release of the therapeutic agent Z.

In some examples, compositions can include the bioorthogonal molecule and/or the releasing molecule in which Z is a therapeutic agent that can be unstable to storage and handling but whose stability is enhanced by modification with a bioorthogonal molecule.

In some examples, compositions of molecules can include the bioorthogonal molecule and/or the releasing molecule in which Z is a therapeutic agent that can be unstable throughout the trajectory of administration (e.g. in digestive system), but whose stability is enhanced by modification with a bioorthogonal molecule. In some examples, Z can be a molecule with poor oral bioavailablility.

Figure 8A:
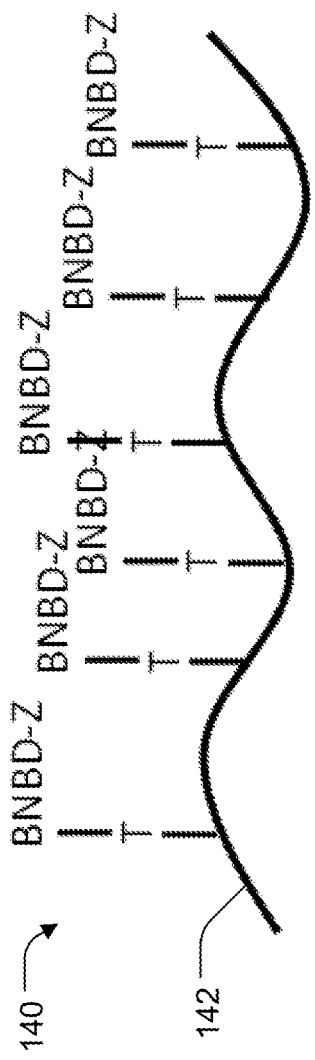
FIG. 8A illustrates a carrier molecule having a bioorthogonal molecule attached thereto, in accordance with an example of the present disclosure.

In some examples, target molecules can include a carrier molecule (e.g. protein, oligonucleotide, colloid, nanoparticle, liposome, micelle, dendrimer, surface, polymer, viral particle, cell surface, hydrogel, small molecule) modified with one or more bioorthogonal molecules (abbreviated BNBD-Z) conjugated either directly or via a tether (abbreviated T). In some examples, the carrier molecule leads to accumulation at a specific anatomical localization (e.g. tissue, organ) and/or endows beneficial pharmacokinetic properties. Multiple bioorthogonal molecules with the same or different leaving groups Z can be attached to one or more carrier molecules. In one example, two or more different therapeutic agents can be attached to a single carrier molecule. In another example, the target molecule (via multiple bioorthogonal molecules) can include both releasable therapeutic agents and releasable reporter molecules. Non-limiting examples of this are illustrated in FIGS. 8A and 9A, which depict the target molecule 140 including a carrier molecule 142 and a plurality of bioorthogonal molecules bound to the carrier molecule 142 via a tether group.

Figure 8B:
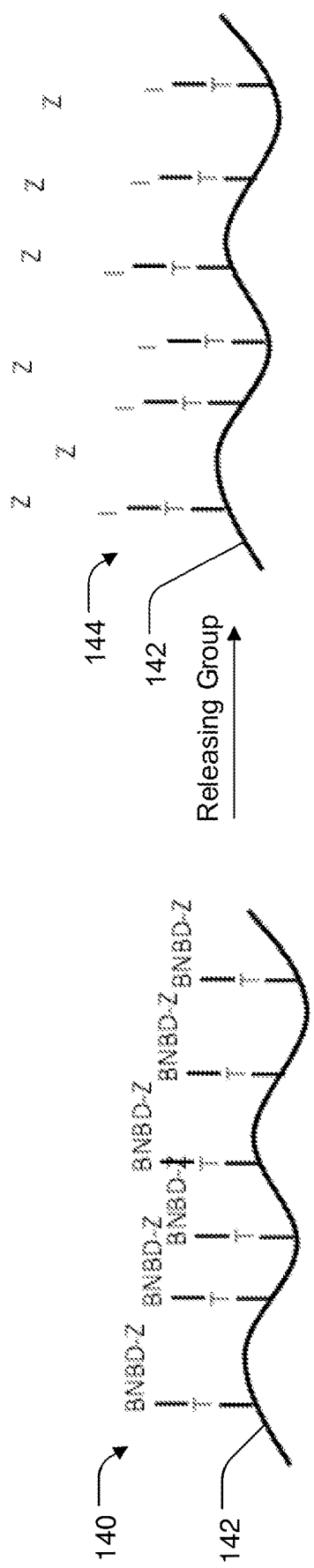
FIG. 8B illustrates a method of releasing a leaving group Z from a carrier molecule, in accordance with an example of the present disclosure.

In some examples, compositions can include a releasing molecule (abbreviated as Tz) and a carrier molecule modified with one or more bioorthogonal molecules (shown as BNBD-Z), in which the releasing molecule triggers the release of Z. For example, as illustrated in FIGS. 8B and 9B, a target molecule 140 or 150 can include a carrier molecule 142 or 152 having a plurality of bioorthogonal molecules attached thereto via a tether T.

Reaction with a releasing group can release Z from the bioorthogonal molecule. In some examples, as illustrated in FIG. 8B, Z can be released into solution. In other examples, as illustrated in FIG. 9B, Z can remain attached in a liberated form on the carrier molecule 152.

Figure 8C:
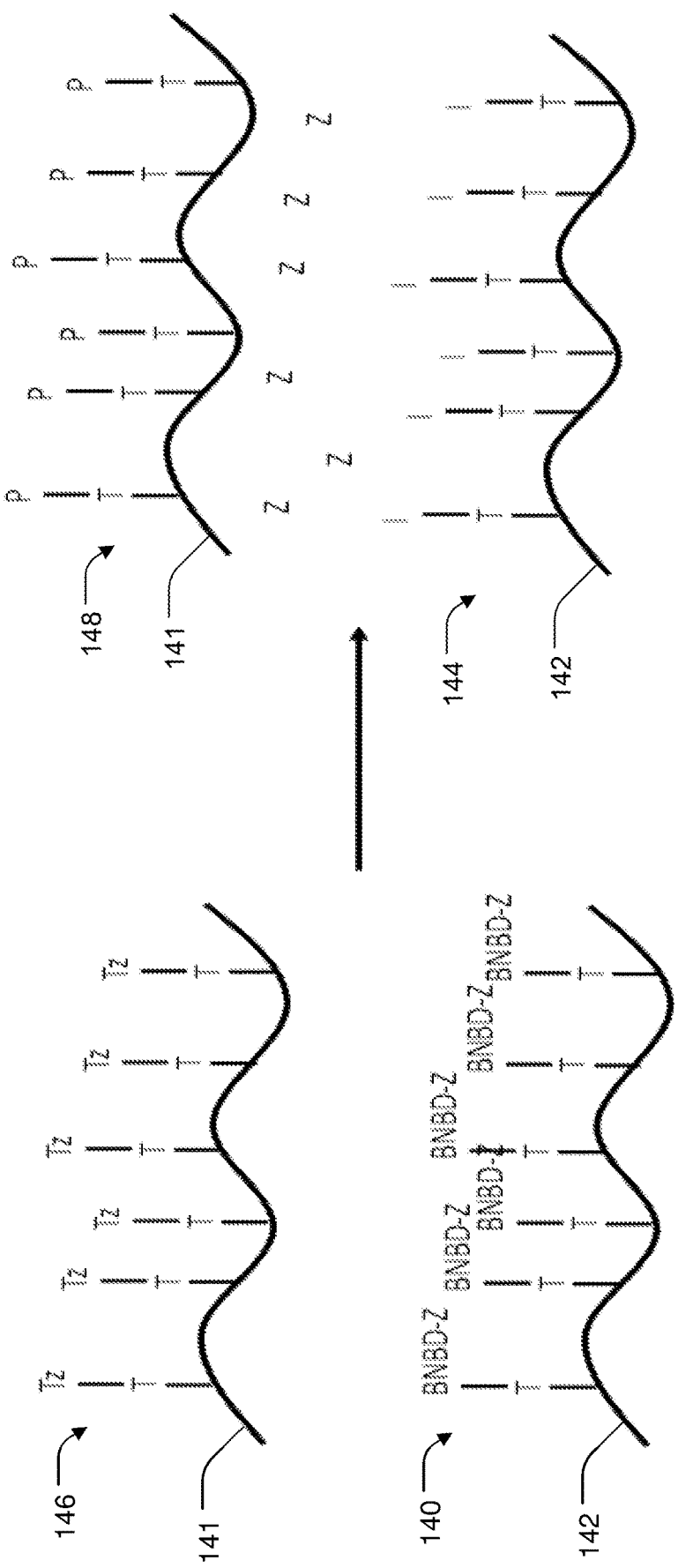
FIG. 8C illustrates another method of releasing a leaving group Z from a carrier molecule, in accordance with an example of the present disclosure.
Figure 9C:
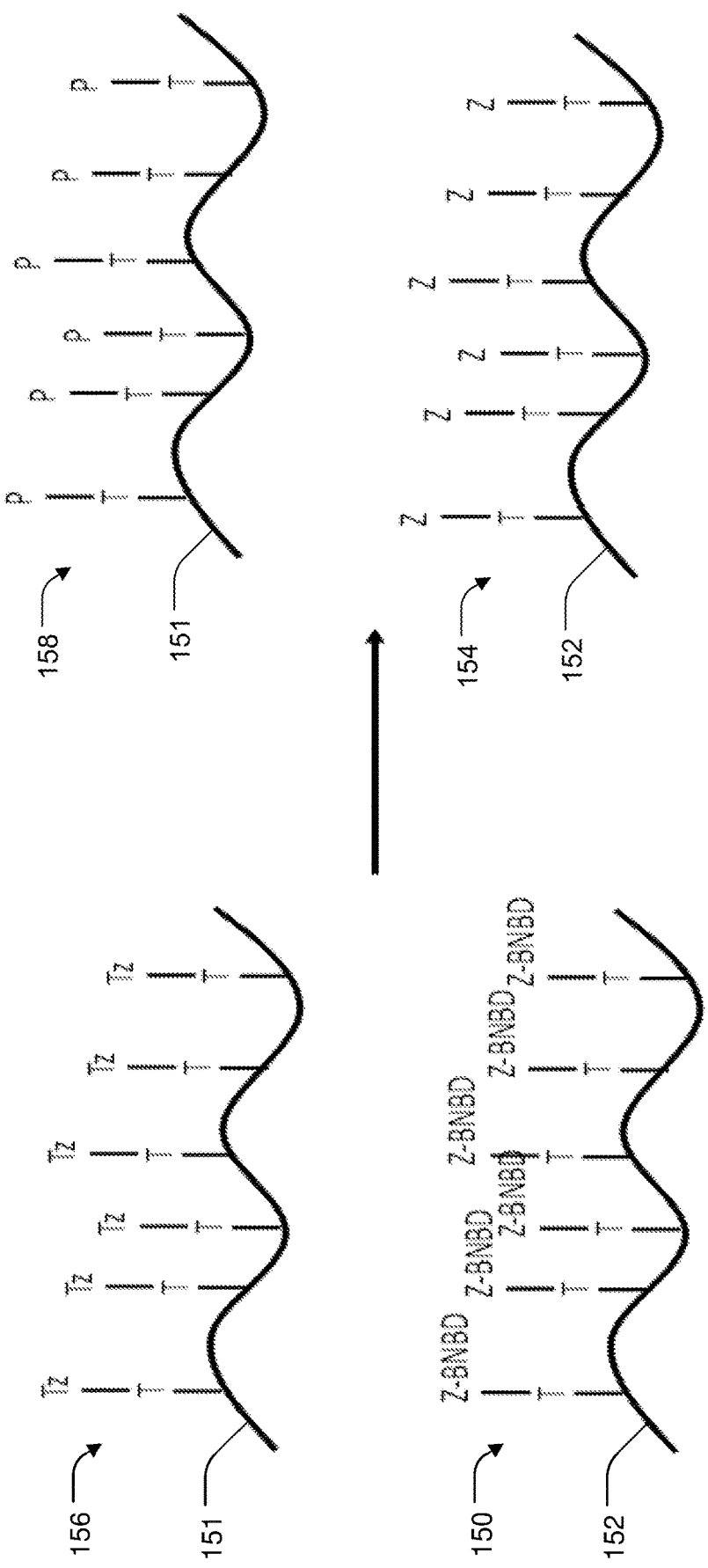
FIG. 9C illustrates another method of retaining a leaving group Z on a carrier molecule, in accordance with an example of the present disclosure.

In some examples, compositions can include a first carrier molecule modified with one or more releasing molecules (shown as Tz), and a second carrier molecule modified with one or more bioorthogonal molecules. In this example, the first and second carrier molecules can interact to trigger the release of Z. Non-limiting examples are illustrated in FIGS. 8C and 9C. Specifically, a releasing molecule 146 or 156 can include a first carrier molecule 141 or 151 having a plurality of releasing groups attached thereto. A first target molecule can include a second carrier molecule 142 or 152 including a plurality of bioorthogonal molecules attached thereto. Interaction between the releasing molecule 146 or 156 and the target molecule 140 or 150 can produce a first product molecule 148 or 158 and a second product molecule 144 or 154. In some examples, as illustrated in FIG. 8C, Z can be released into solution. In other examples, as illustrated in FIG. 9C, Z can remain attached in a liberated form on the carrier molecule 152.

Figure 10A:
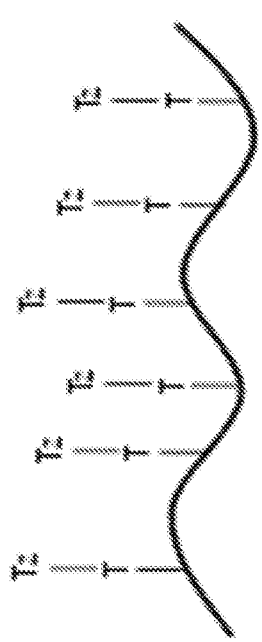
FIG. 10A illustrates a method of releasing a leaving group Z from a bioorthogonal molecule, in accordance with an example of the present disclosure.
Figure 10A:
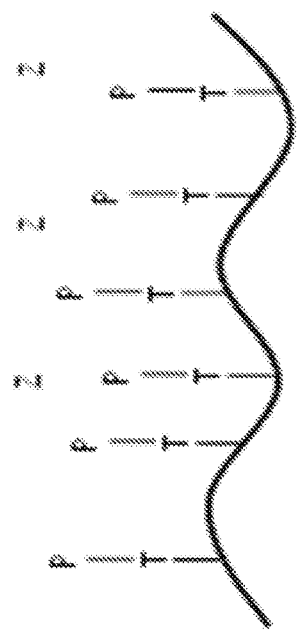

In some examples, compositions can include a bioorthogonal molecule (abbreviated as BNBD-Z) and a carrier molecule modified with one or more releasing molecules (shown as Tz). Reaction between the bioorthogonal molecule and the releasing molecule can trigger the release of Z. One non-limiting example is illustrated in FIG. 10A.

In some examples, the bioorthogonal molecules can be used in methods of spatiotemporally controlled release of therapeutics or imaging agents in which compositions including a bioorthogonal molecule or a releasing molecule, at least one of which is linked to a carrier molecule, are co-administered simultaneously or sequentially with a time delay by any means of administration (e.g. topical, orally, intravenously, intramuscularly).

In some examples, the bioorthogonal molecules can be used in methods of spatiotemporally controlled release of therapeutics or imaging agents in which carrier molecules with attached bioorthogonal molecules are implanted at a specific location (e.g. hydrogel, stint, biomaterial) and administration of releasing molecules releases Z.

In some examples, the bioorthogonal molecules can be used in methods of spatiotemporally controlled release of therapeutics or imaging agents in which carrier molecules with attached releasing molecules are implanted at a specific location (e.g. hydrogel, stint, biomaterial) and administration of bioorthogonal molecules releases Z.

In some examples, bioorthogonal molecules can have a structure X-T-BNBD-Z, in which BNBD stands for a bioorthogonal molecule having a general structure according to Formula I, and where X is a group that reacts with cycloalkenes (e.g. cis-cyclootene, cyclorpropene), Z is a leaving group, and T is a tether. In some examples, the bioorthogonal molecule can be modified with additional functional groups or reporter molecules (e.g. fluorophores, radionuclides, haptens, affinity binders).

In some examples, bioorthogonal molecules can have a structure Y-T-BNBD-Z, in which BNBD stands for molecules having a general structure according to Formula I, Y is a group that is inert to cycloalkenes (e.g. cis-cyclootene, cyclorpropene, norbornene) but orthogonally reacts with other groups (example of reagent pairs: azide/cyclooctyne), Z is a releasable group, and T is a tether. In some examples, the bioorthogonal molecules can be modified with additional functional groups or reporter molecules (e.g. fluorophores, radionuclides, haptens, affinity binders).

In some examples, releasing molecules containing two or more releasing molecules or groups (abbreviated Tz) can be attached to a carrier or modified with a reporter or other molecule (T is tether, wavy line indicates site of modification or attachment, B indicates branch point), such as:

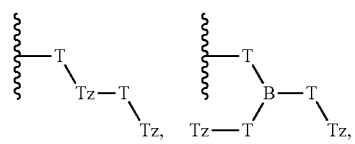

or the like.

In some examples, releasing molecules or groups can be attached to carrier molecules or reporter molecules (abbreviated R) including for example fluorophores, radionuclides, haptens, chromophores, or the like. Non-limiting examples can include:

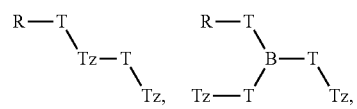

or the like.

In some examples, molecules can include one or more bioorthogonal molecules (abbreviated as BNBD-Z) and a group that reacts with releasing molecules and are attached to a carrier or modified with a reporter or other molecule (abbreviated X, T is a tether, wavy line indicates site of modification or attachment, B indicates branch point).

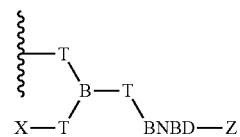

In some examples, molecules can include one or more bioorthogonal molecules of (abbreviated as BNBD-Z) and a group (abbreviated Y) that is unreactive to releasing molecules but orthogonally reacts with other groups (e.g. azide, cyclooctyne, etc.) and are attached to a carrier or modified with a reporter or other molecule (abbreviated X, T is a tether, wavy line indicates site of modification or attachment, B indicates branch point).

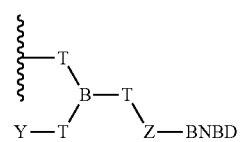

In some specific examples, these molecules can be attached to carrier molecules or reporter molecules (abbreviated R) including for example fluorophores, radionuclides, haptens, chromophore. Non-limiting examples can include:

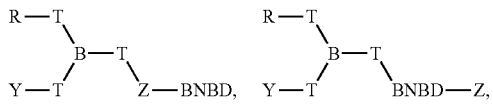

or the like.

Figure 10B:
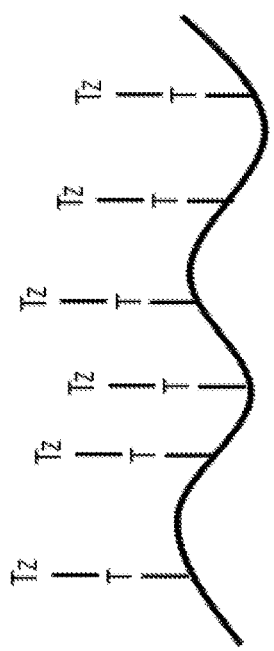
FIG. 10B illustrates another method of releasing a leaving group Z from a bioorthogonal molecule, in accordance with an example of the present disclosure.
Figure 10B:
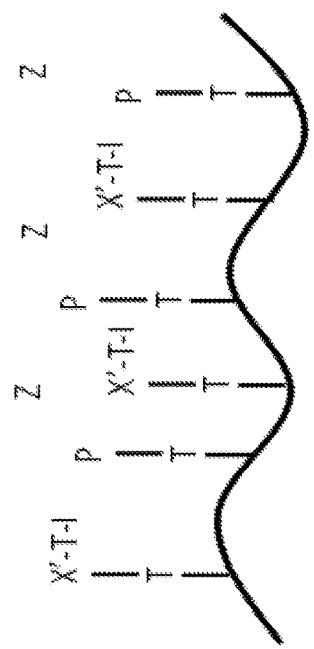
Figure 10C:
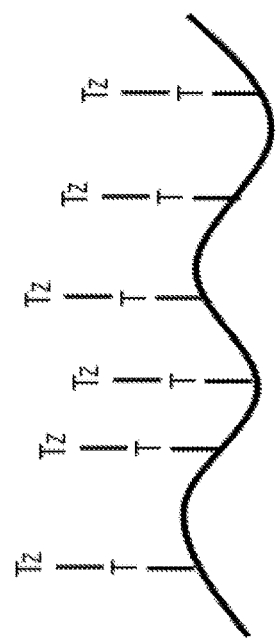
FIG. 10C illustrates a method of transferring a leaving group Z to a carrier molecule, in accordance with an example of the present disclosure.
Figure 10C:
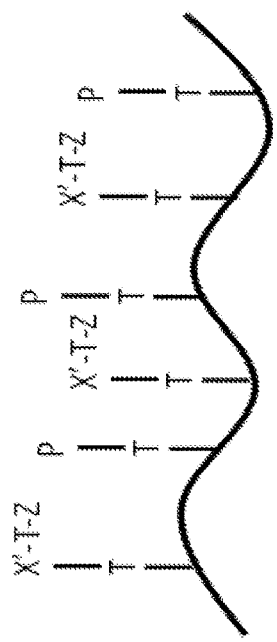

In some examples, compositions including a molecule having a structure X-T-BNBD-Z and a carrier molecule (e.g. protein, oligonucleotide, colloid, nanoparticle, liposome, micelle, dendrimer, surface, polymer, viral particle, cell surface, hydrogel) can be modified with two or more releasing molecules (shown as Tz), which can lead to covalent linkage of the former molecules to the releasing molecule with simultaneous release of Z. (X': linker structure formed by the reaction of Tz and X; P and I: side-products formed by the reaction of BNBD and Tz). Non-limiting examples of such reactions are illustrated in FIGS. 10B and 10C. In some examples, as illustrated in FIG. 10B, the released group Z can be liberated into solution. In other examples, as illustrated in FIG. 10C, Z can remain attached to the carrier molecule and side product I can be released into solution.

Figure 11A:
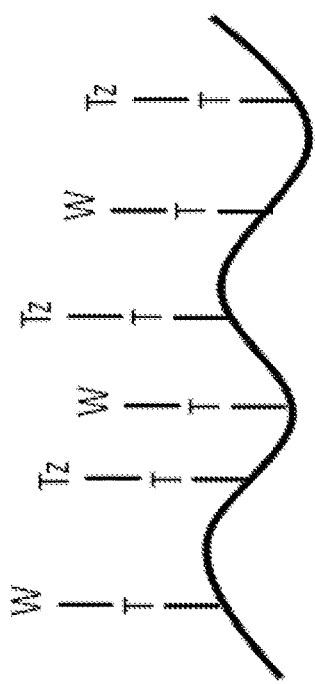
FIG. 11A illustrates a method of releasing a leaving group Z from a bioorthogonal molecule, in accordance with an example of the present disclosure.
Figure 11A:
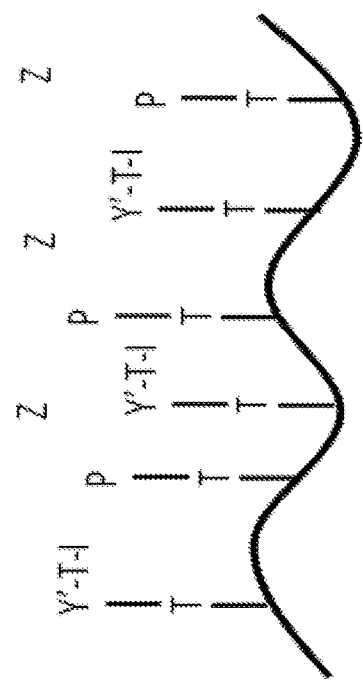
Figure 11B:
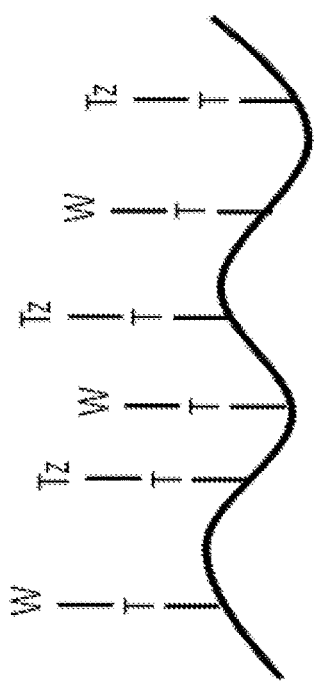
FIG. 11B illustrates a method of transferring a leaving group Z to a carrier molecule, in accordance with an example of the present disclosure.
Figure 11B:
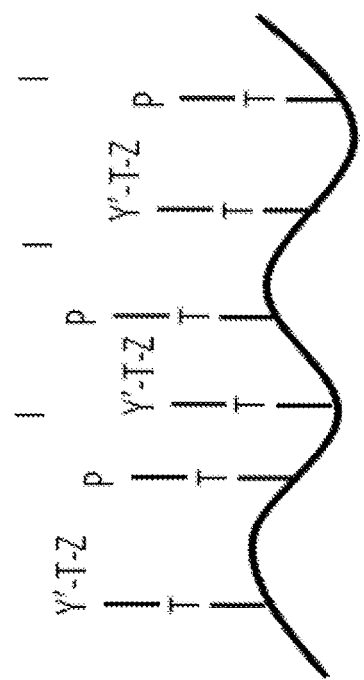

In other examples, a carrier molecule (e.g. protein, oligonucleotide, colloid, nanoparticle, liposome, micelle, dendrimer, surface, polymer, viral particle, cell surface, hydrogel) can be modified with two or more molecules or groups (W) that form a covalent linkage with Y (Y') and releasing molecules (Tz) that release Z. (P and I: side-products formed by the reaction of BNBD and Tz). In some examples, as illustrated in FIG. 11A, the released moiety Z can be liberated into solution. In other examples, as illustrated in FIG. 11B, Z can remain attached to the carrier molecule and side product I can be released into solution.

Figure 12A:
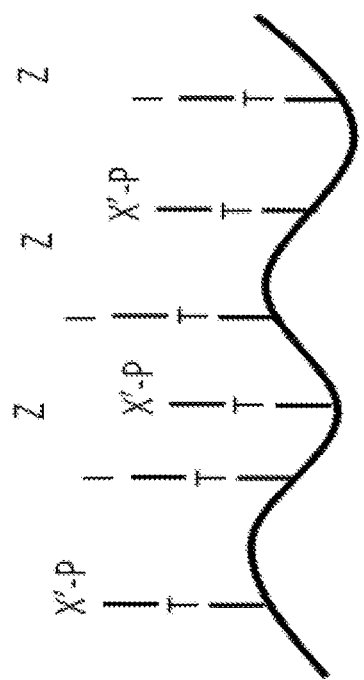
FIG. 12A illustrates a method of releasing a leaving group Z from a carrier molecule, in accordance with an example of the present disclosure.
Figure 12A:
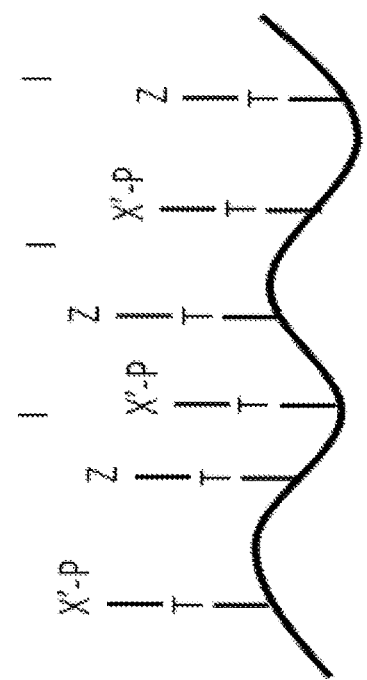
Figure 12A:
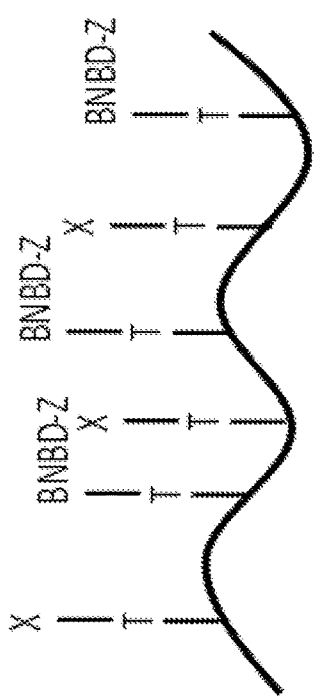
Figure 12B:
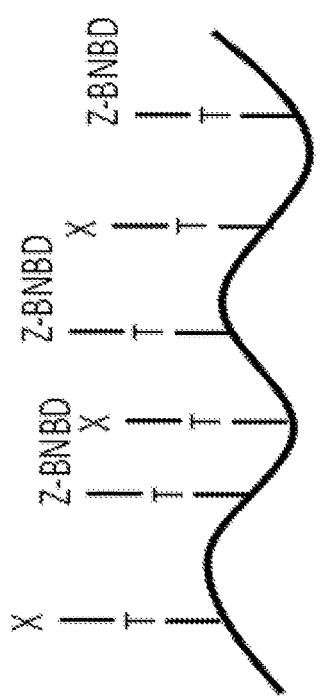
FIG. 12B illustrates a method of retaining a leaving group Z on a carrier molecule, in accordance with an example of the present disclosure.

In some examples, compositions can include a first molecule that includes two or more releasing molecules (abbreviated as Tz-Tz) and a second molecule including a carrier molecule (e.g. protein, oligonucleotide, colloid, nanoparticle, liposome, micelle, dendrimer, surface, polymer, viral particle, cell surface, hydrogel) modified with two or more bioorthogonal molecules (shown as BNBD-Z) as well as a second type of molecule that reacts with releasing molecules (shown as X), which lead to covalent linkage of the former molecules to the latter molecule with simultaneous release of Z. (X': linker structure formed by the reaction of Tz and X; P and I: side-products formed by the reaction of BNBD and Tz). In some examples, as illustrated in FIG. 12A, the released moiety Z can be liberated into solution. In other examples, as illustrated in FIG. 12B, Z can remain attached to the carrier molecule and side product I can be released into solution.

In some examples, bioorthogonal molecules can function as a cleavable linker between two molecules of interest attached via Z and T. In some examples, the molecules of interest attached via Z and T can be combinations of biomacromolecules (e.g. oligonucleotide, polypeptide). In some examples, one or more of the modifications (Z or T) can be linked to a surface. In some examples, one or more of the modifications (Z or T) can be linked to a solid support (e.g. nanoparticle, colloid, polymeric support). In some examples, various materials and macromolecules (e.g. polymers, hydrogels, dendrimers) can include connective bioorthogonal molecule elements.

Figure 13A:
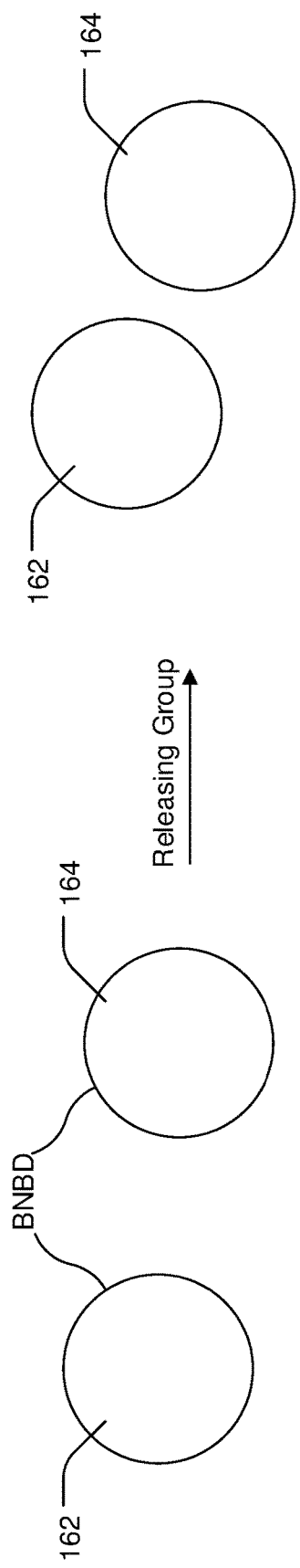
FIG. 13A illustrates a method of linking separate molecules together, in accordance with an example of the present disclosure.

In some examples, compositions can include releasing molecules and bioorthogonal molecules linking two molecules of interest, where contact of the releasing molecule and the bioorthogonal molecule causes the dissociation of the two molecules of interest. One examples of this is illustrated in FIG. 13A. Specifically, a first molecule 162 and a second molecule can be bound together via a bioorthogonal molecule. Reaction of the bioorthogonal molecule with a releasing group can allow dissociation of the first molecule 162 and the second molecule 164.

Figure 13B:
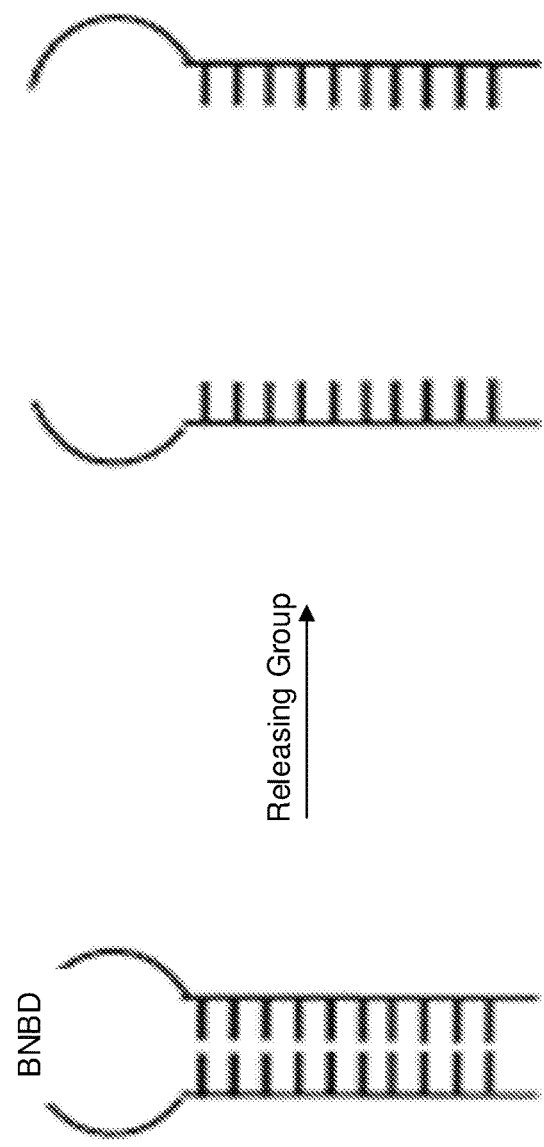
FIG. 13B illustrates a method of linking separate nucleic acids together, in accordance with an example of the present disclosure.

In some examples, the two molecules of interest can be polypeptides or oligonucleotides. In the case of oligonucleotides, cleavage may cause dissociation of a duplex, as illustrated in FIG. 13B.

In some examples, compositions can include releasing molecules and bioorthogonal molecules where two molecules of interest are attached to a surface or solid support, in which contact of the releasing molecule and the bioorthogonal molecule causes the cleavage of a molecules of interest from a surface or a solid support.

Figure 13C:
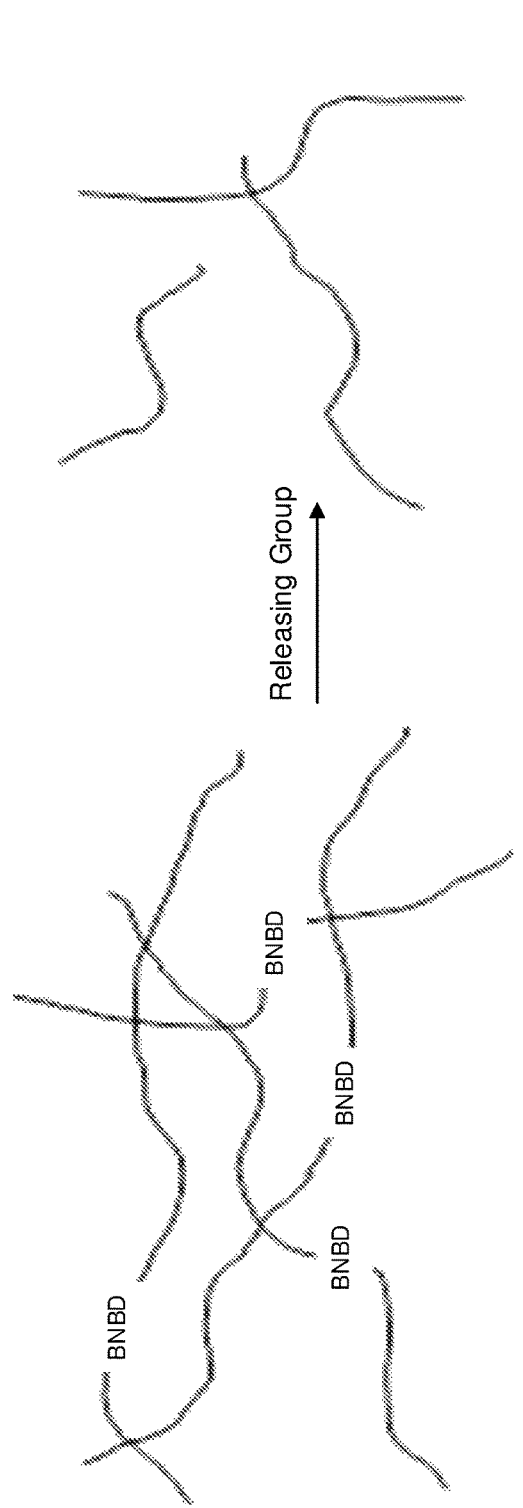
FIG. 13C illustrates a method of linking separate materials/macromolecules together, in accordance with an example of the present disclosure.

In some examples, compositions can include releasing molecules and materials and macromolecules, which include connective bioorthogonal molecule elements and in which contact of the releasing molecules and the bioorthogonal molecules with the material/macromolecule leads to partial or complete degradation of the latter, as illustrated in FIG. 13C.

Figure 13D:
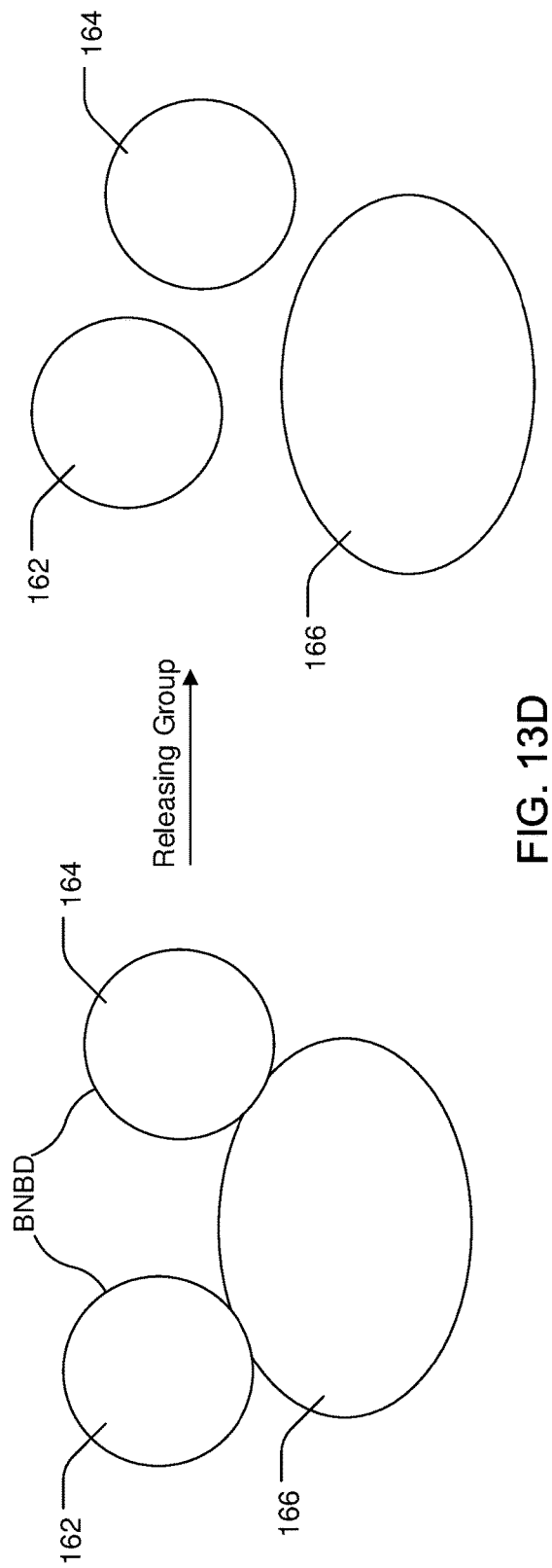
FIG. 13D illustrates a method of controlling the affinity of separate molecules for one another, in accordance with an example of the present disclosure.

In some examples, the bioorthogonal compounds can be used in methods for controlling the affinity of a molecule of interest connected by a linker containing a bioorthogonal molecule to a target molecule, in which cleavage of the linker induced by a releasing molecule reduces the affinity to the target. For example, as illustrated in FIG. 13D, a first molecule 162 and a second molecule 164 can be connected by a linker including a bioorthogonal molecule. This can increase the affinity of the first molecule 162 and second molecule 164 for the target molecule 166. Reaction with a releasing group can release the bioorthogonal molecule from the linker group to allow dissociation of the first molecule 162 and the second molecule 164, which can also decrease the affinity toward target molecule 166. Thus, the strong binding between the target molecule 166 and the first and second molecules 162, 164 can be reduced to weak binding therebetween as a result of the release of the bioorthogonal molecule from the linker group.

Figure 13E:
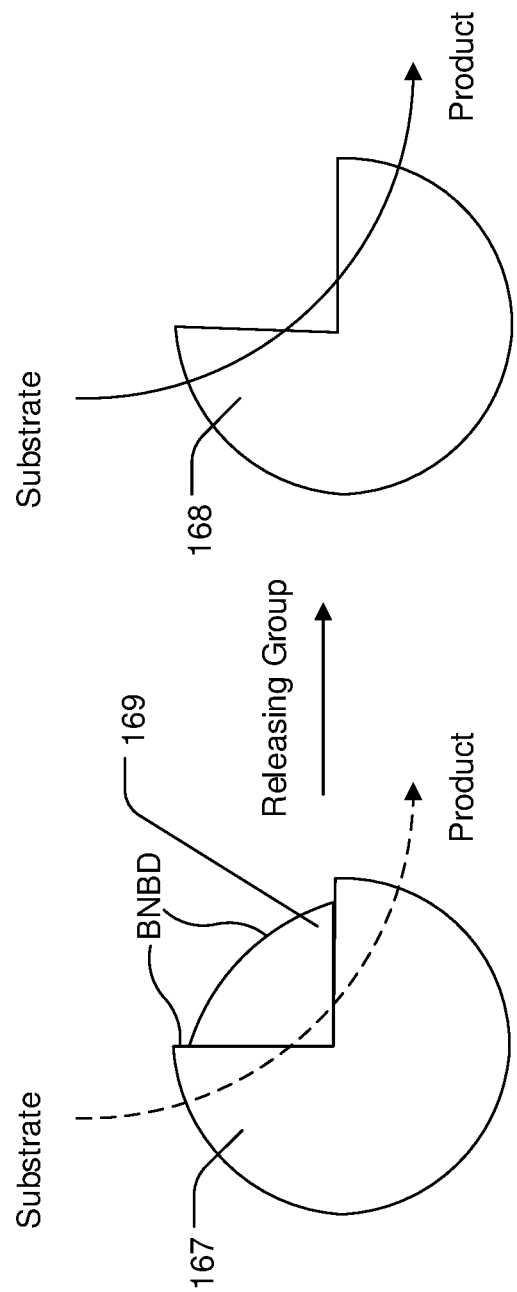
FIG. 13E illustrates a method of controlling the activity of an enzyme, in accordance with an example of the present disclosure.

In some examples, the bioorthogonal molecule can be used in methods for controlling the activity of an enzyme modified with an inhibitor via a linker containing a bioorthogonal molecule by cleavage of the linker by a releasing molecule, which reduces the inhibition of the enzyme. For example, as illustrated in FIG. 13E, an inactive enzyme 167 can be modified with an inhibitor 169. The inhibitor 169 and the inactive enzyme 167 can be linked together via a linker including a bioorthogonal molecule. Reaction with a releasing group can cause the release of the bioorthogonal molecule and the inhibitor 169 to produce an active enzyme 168. In some examples, activation of the enzyme can be coupled to a reporter event (e.g. bioluminescence, activation of a fluorophore) or therapeutic event (e.g. prodrug activation).

Figure 13F:
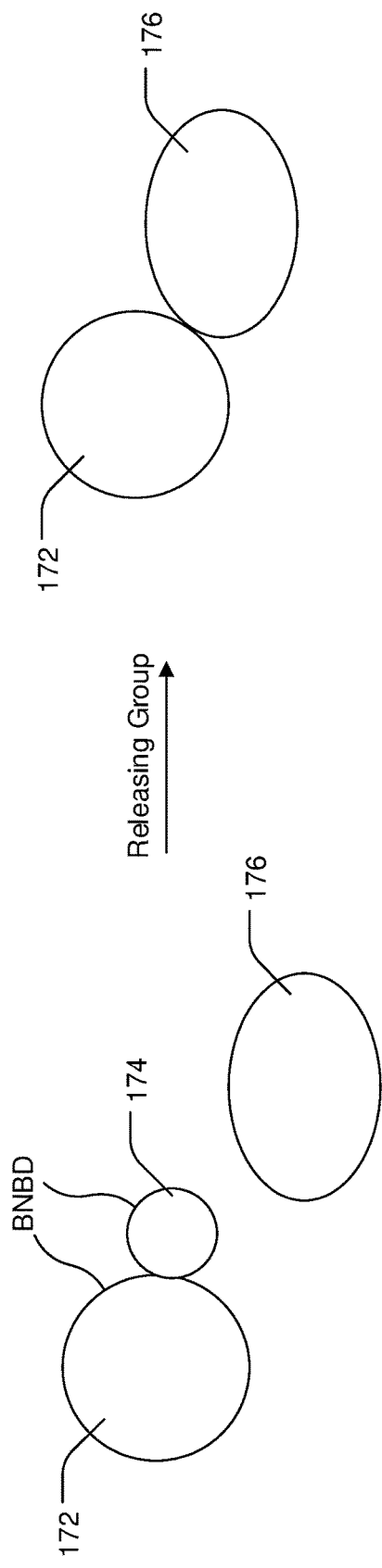
FIG. 13F illustrates a method of controlling the affinity of separate molecules for one another, in accordance with an example of the present disclosure.

In some examples, the bioorthogonal molecule can be used in methods for controlling the affinity of a molecule including a molecule of interest and an affinity-control molecule, which reduces the affinity to the target, connected by a linker including a bioorthogonal molecule to a target molecule, in which cleavage of the linker by a releasing molecule restores the affinity of the molecule of interest to a target molecule. For example, as illustrated in FIG. 13F, a target molecule 172 and an affinity-control molecule 174 can be linked together via a linker including a bioorthogonal molecule. This can decrease the affinity of the target molecule 172 to a molecule of interest 176. Reaction of a releasing group with the bioorthogonal molecule can release the bioorthogonal molecule from the linker, which can also release the affinity-control molecule 174 from the target molecule. This can increase the affinity of the target molecule 172 for the molecule of interest 176.

Figure 13G:
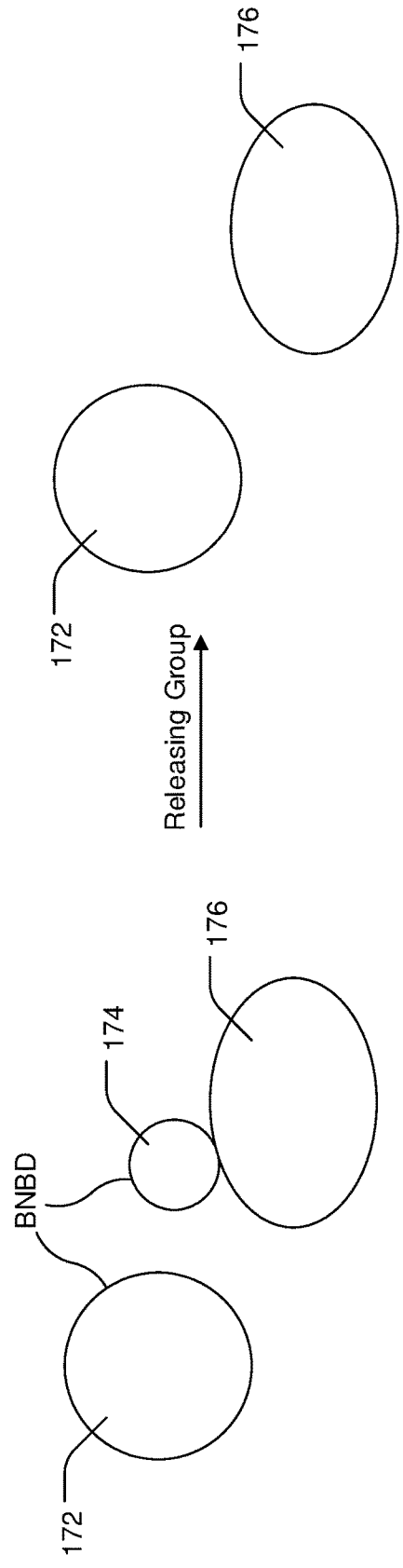
FIG. 13G illustrates a method of controlling the affinity of separate molecules for one another, in accordance with an example of the present disclosure.

In some examples, the bioorthogonal molecules can be used in methods for controlling the proximity of a molecule of interest and a target molecule. The molecule of interest can be linked to a localization molecule via a linker containing a bioorthogonal molecule and localized to a specific site (e.g. anatomical location, intracellular location, surface) on a second molecule. Cleaving the linker with a releasing molecule can dissociate the molecule of interest and the target molecule. For example, as illustrated in FIG. 13G, a target molecule 172 can be linked to a localization molecule 174 via a linker including a bioorthogonal molecule. The localization molecule 174 can facilitate interaction between the target molecule 172 and the molecule interest 176. Reaction of the bioorthogonal molecule with a releasing group can release the bioorthogonal molecule and the localization molecule 174, which can decrease the affinity of the target molecule 172 and the molecule of interest 176 to prevent or minimize further interaction therebetween. In some examples, the target molecule may modify the molecule of interest.

Figure 13H:
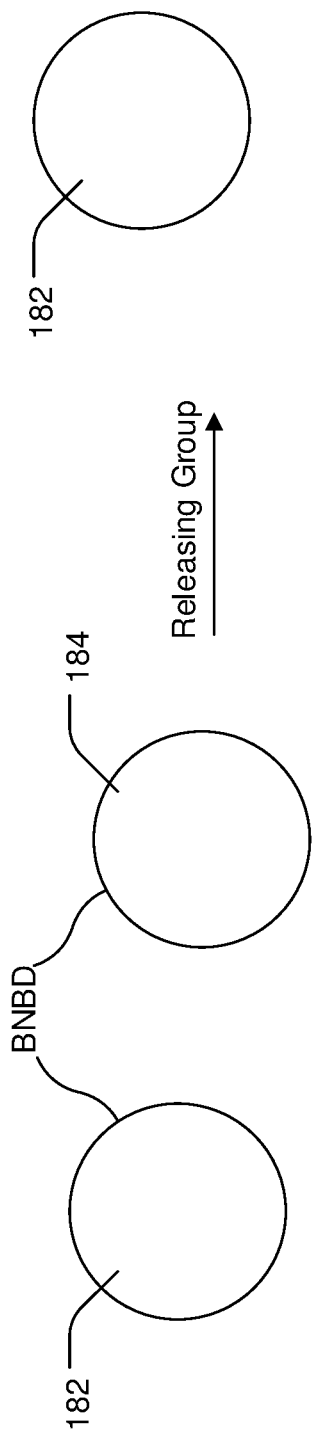
FIG. 13H illustrates a method of controlling the half-life of a target molecule, in accordance with an example of the present disclosure.

In some examples, the bioorthogonal molecules can be used in methods for controlling the half-life of a molecule of interest. The molecule of interest can be linked to a removal molecule, via a linker containing a bioorthogonal molecule, in a system (e.g. cell, organism, patient). Cleaving the linker with a releasing molecule can increase the half-life of the molecule of interest. For example, as illustrated in FIG. 13H, a target molecule 182 can be linked to a removal molecule 184 via a linker including a bioorthogonal molecule. Reaction of the bioorthogonal molecule with a releasing group can remove the bioorthogonal molecule and the removal molecule 184 to increase the half-life of the target molecule 182. In some examples, the removal molecule can target the molecule of interest to the proteasome, or lysosome. In yet additional examples, the removal molecule can interact with a molecule that tags it for removal (e.g. E3 ubiquitin ligase). In still other examples, the removal molecules can localize to excretory organs.

In some other examples, the molecule of interest can be linked to a retention molecule, via a linker containing a bioorthogonal molecule, in a system (e.g. cell, organism, patient). Cleaving the linker with a releasing molecule can decrease the half-life of the molecule of interest and lead to removal of the molecule of interest from the system. This can also be illustrated using FIG. 13H, where the molecule 184 represents a retention molecule instead of a removal molecule. Reaction of the bioorthogonal molecule with a releasing group can remove the bioorthogonal molecule and the retention molecule 184 to decrease the half-life of the target molecule 182. In some examples, the retention molecule can be a molecule that enhances the circulatory half-life of a molecule such as serum albumin or a molecule that binds serum albumin.

In some examples, the bioorthogonal molecule can be used in methods for controlling the localization of a molecule of interest linked to a localization molecule via a linker containing a bioorthogonal molecule to a specific site (e.g. anatomical location, intracellular location, surface). Cleaving the linker with a releasing molecule can cause dissociation of the molecule of interest from the specific site.

In some examples, the bioorthogonal molecule can be used in methods of imaging one or a series of objects with molecules including a binding moiety (e.g. small-molecule, polypeptide, oligonucleotide) and a reporter molecule (e.g. fluorophore) connected via a linker containing a bioorthogonal molecule. In this example, a first set of molecules can bind to the target molecules, the reporter signal can be measured (e.g. fluorescence microscopy), the reporter molecule can released by cleavage of the linker by contact with a releasing molecule, and delivery of a second set of molecules for reporting. The cycle can be repeated as desired.

Figure 13I:
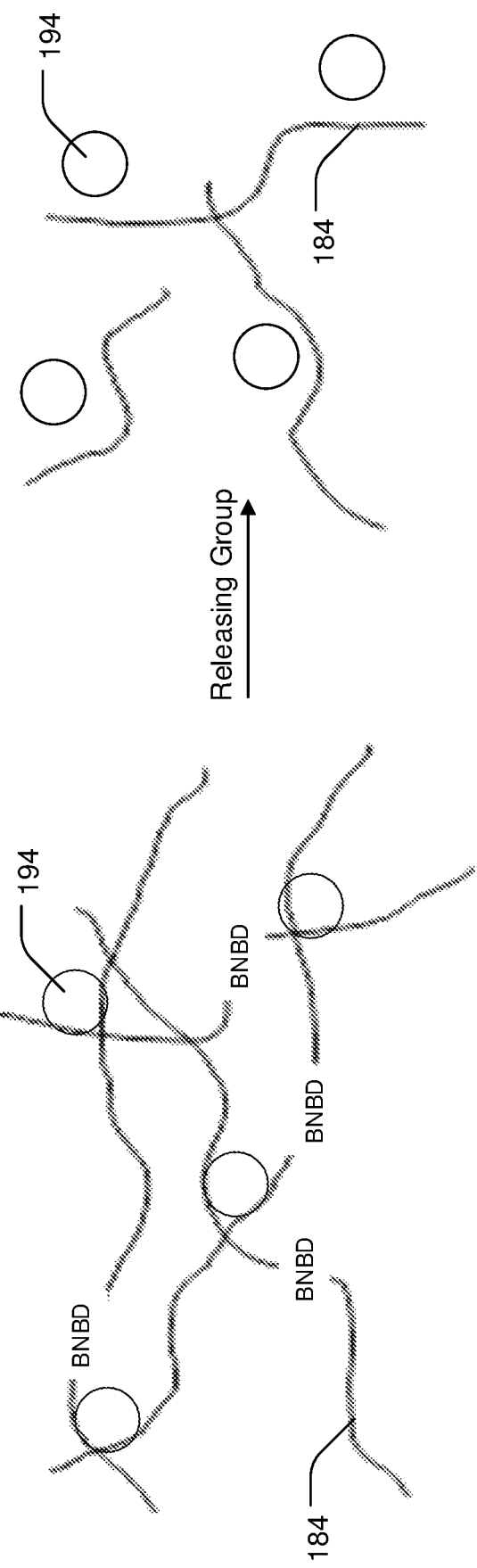
FIG. 13I illustrates a method of releasing macromolecules from a material, in accordance with an example of the present disclosure.

In some examples, the bioorthogonal molecule can be used in methods for the spatio-temporal release of molecules, in which the molecules of interest are embedded in a material or macromolecule including connective bioorthogonal molecule elements and are released upon partial or complete degradation of the material/macromolecule upon contact with a releasing molecule. For example, as illustrated in FIG. 13I, a material 184 and associated macromolecules 194 can be bound together via connective bioorthogonal molecule elements. Reaction of the bioorthogonal molecule elements with a releasing group can partially or completely degrade the material 184 to release individual material segments 184 and individual macromolecules 194.

In some examples, bioorthogonal molecules can be used in methods for the spatio-temporal release of molecules, in which the molecules of interest are bound to a molecule consisting of two affinity binders connected by a linker containing a bioorthogonal molecules, which upon contact with a releasing molecule releases the molecule of interest.

In some examples, a bioorthogonal molecule having a structure according to Formula V can be used in methods of spatio-temporal controlled release of a molecule of interest Z (e.g. therapeutic agent, reporter molecule) by spontaneous decomposition of the bioorthogonal molecule. In some additional examples, Z can be a therapeutic agent adapted for any desired means of administration (e.g. orally, intravenously, intravesically, topically, intramuscularly). In some examples, $R^9$ can enhance the circulatory half-life of the molecule of interest. In other examples, $R^9$ can causes the enhanced accumulation of molecules of interest at sites of interest (e.g. tissue, tumor, organ).

Various aspects of the bioorthogonal molecules and associated compositions, systems, and methods can be illustrated via a number of non-limiting examples, as follows:

In some examples, a bioorthogonal molecule, can include a molecule having a structure according to:

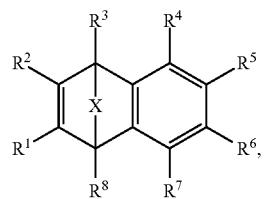

wherein $R^1$-$R^8$ are independently selected from H, a substituted or unsubstituted $C_1$-$C_4$ alkyl or alkylene group, COOH, COOR$^9$, COR$^9$, CONR$^9$R$^{10}$, CN, CF$_3$, and SO$_2$R$^9$, where R$^9$ and R$^{10}$ are independently selected from H and a substituted or unsubstituted C$_1$-C$_4$ alkyl or alkylene group, with the proviso that one of R$^3$-R$^8$ comprises a leaving group, and wherein X is O, S, N, SO, SO$_2$, SR*, Se, PO$_2^-$, or NRR'$^+$, and where R and R' are independently selected from H or a substituted or unsubstituted C$_1$-C$_4$ alkyl or alkylene group.

In some examples of a bioorthogonal molecule, X is O or N.

In some examples of a bioorthogonal molecule, R$^5$ or R$^8$ includes the leaving group.

In some examples of a bioorthogonal molecule, the leaving group is coupled to R$^5$ or R$^8$ via a linker group.

In some examples of a bioorthogonal molecule, the linker group is a substituted or unsubstituted C$_1$-C$_3$ alkyl or alkylene group.

In some examples of a bioorthogonal molecule, R$^8$ includes the leaving group.

In some examples of a bioorthogonal molecule, the leaving group includes a payload selected from the group consisting of a therapeutic agent, a prodrug, a vitamin, a cytotoxic agent, a protein, a nucleic acid, a lipid, a polymer, and combinations thereof.

In some examples of a bioorthogonal molecule, the leaving group includes COOR$^{11}$, O-Aryl-R$^{11}$, POR$^{11}$R$^{12}$R$^{13+}$, ONHOR$^{11}$, or NR$^{11}$R$^{12}$R$^{13+}$, wherein R$^{11}$, R$^{12}$, and R$^{13}$ are independently selected from a payload, H, and a substituted or unsubstituted C$_1$-C$_4$ alkyl or alkylene group.

In some examples of a bioorthogonal molecule, the leaving group comprises COOR$^{11}$ or POR$^{11}$R$^{12}$R$^{13+}$, wherein R$^{11}$, R$^{12}$, and R$^{13}$ are independently selected from a payload, H, and a substituted or unsubstituted C$_1$-C$_4$ alkyl or alkylene group.

In some examples of a bioorthogonal molecule, the molecule has a structure according to:

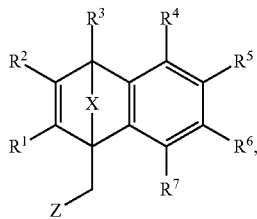

where Z is the leaving group.

In some examples of a bioorthogonal molecule, R$^1$, R$^2$, or both comprise and electron withdrawing group.

In some examples of a bioorthogonal molecule, the electron withdrawing group is a member of the group consisting of COOH, COOR$^9$, COR$^9$, CONR$^9$R$^{10}$, CN, CF$_3$, SO$_2$R$^9$, and NO$_2$, where R$^9$ and R$^{10}$ are independently selected from H and a substituted or unsubstituted C$_1$-C$_4$ alkyl or alkylene group.

In some examples of a bioorthogonal molecule, the bioorthogonal molecule further includes a tether group configured to tether the molecule to a substrate.

In some examples of a bioorthogonal molecule, the tether group is attached to the molecule at one of R$^3$-R$^8$ or at X.

In some examples of a bioorthogonal molecule, the tether group is attached to the molecule at X.

In some examples of a bioorthogonal molecule, the substrate is a protein, a nucleic acid, a lipid, or a polymer.

In some examples of a bioorthogonal molecule, the bioorthogonal molecule further includes an SR$^{14}$ group coupled to the bioorthogonal molecule at R$^2$, wherein R$^{14}$ is selected from H or a substituted or unsubstituted C$_1$-C$_4$ alkyl or alkylene group.

In some examples of a bioorthogonal molecule, the bioorthogonal molecule including the SR$^{14}$ group further includes an electron withdrawing group coupled to the molecule at R$^1$, R$^2$, or both.

In some examples of a bioorthogonal molecule, the electron withdrawing group is selected from the group consisting of COOH, COOR$^9$, COR$^9$, CONR$^9$R$^{10}$, CN, CF$_3$, and SO$_2$R$^9$, where R$^9$ and R$^{10}$ are independently selected from H and a substituted or unsubstituted C$_1$-C$_4$ alkyl or alkylene group.

In some examples of a bioorthogonal molecule, both R$^1$ and R$^2$ include individual electron withdrawing groups.

In some examples, a therapeutic composition includes a bioorthogonal molecule as described herein and a pharmaceutically acceptable carrier.

In some examples of a therapeutic composition, the bioorthogonal molecule is attached to a carrier molecule.

In some examples of a therapeutic composition, the carrier molecule is a member selected from the group consisting of a protein, a oligonucleotide, a colloid, a nanoparticle, a liposome, a micelle, a dendrimer, a surface, a polymer, a viral particle, a cell surface, a hydrogel, a small molecule, and combinations thereof.

In some examples of a therapeutic composition, the pharmaceutically acceptable carrier is formulated for administration via injection or is an injectable dosage form.

In some examples of a therapeutic composition, the pharmaceutically acceptable carrier is formulated for enteral administration or is an enteral dosage form.

In some examples of a therapeutic composition, the pharmaceutically acceptable carrier is formulated as a capsule or tablet.

In some examples of a therapeutic composition, the pharmaceutically acceptable carrier is formulated for topical or transdermal administration or is a topical dosage form or transdermal dosage form.

In some examples of a therapeutic composition, the pharmaceutically acceptable carrier is formulated as a gel formulation.

In some examples of a therapeutic composition, the pharmaceutically acceptable carrier is formulated as an adhesive patch.

In some examples of a therapeutic composition, the pharmaceutically acceptable carrier is formulated for transmucosal administration or is a transmucosal dosage form.

In some examples of a therapeutic composition, the pharmaceutically acceptable carrier is formulated as a dissolvable buccal film or tablet.

In some examples of a therapeutic composition, the pharmaceutically acceptable carrier is formulated as an eye drop.

In some examples of a therapeutic composition, the therapeutic composition further comprises a releasing molecule.

In some examples, a therapeutic system can include a therapeutic composition as described herein including a bioorthogonal molecule as described herein and a pharmaceutically acceptable carrier. The therapeutic system can also include a releasing composition including a releasing molecule and a second pharmaceutically acceptable carrier.

In some examples of a therapeutic system, the therapeutic composition is disposed in a first container and the releasing composition is disposed in a second container.

In some examples of a therapeutic system, the bioorthogonal molecule has a structure according to:

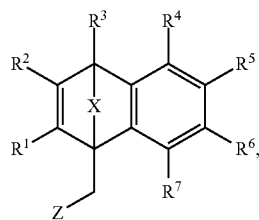

where Z is the leaving group.

In some examples of a therapeutic system, the releasing molecule has a structure according to Formula (III):

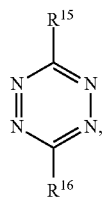

(III)

where $R^{15}$ and $R^{16}$ are independently selected from H, 2-pyridine, and Ph-CONH(($CH_2$)$_2$O)$_3$Me.

In some examples of a therapeutic system, the releasing molecule has a structure according to Formula (IV):

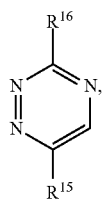

(IV)

where $R^{15}$ and $R^{16}$ are independently selected from H, 2-pyridine, and Ph-CONH(($CH_2$)$_2$O)$_3$Me.

In some examples, a method of reversibly modifying a target molecule can include removably coupling a bioorthogonal molecule as described herein to the target molecule and reacting the bioorthogonal molecule with a releasing molecule to remove the bioorthogonal molecule from the target molecule.

In some examples of a method of reversibly modifying a target molecule, the bioorthogonal molecule is coupled to the target molecule via reaction of the target molecule with a reactive precursor of the bioorthogonal molecule.

In some examples of a method of reversibly modifying a target molecule, the bioorthogonal molecule is incorporated onto the target molecule during synthesis of the target molecule.

In some examples of a method of reversibly modifying a target molecule, coupling the bioorthogonal molecule to the target molecule inactivates the target molecule.

In some examples of a method of reversibly modifying a target molecule, the bioorthogonal molecule acts as a protecting group.

In some examples of a method of reversibly modifying a target molecule, the target molecule is a member of the group consisting of a polypeptide, a carbohydrate, a nucleic acid, a lipid, and combinations thereof.

In some examples, a method of administering a therapeutic agent to a subject can include administering a bioorthogonal molecule as described herein to the subject, the bioorthogonal molecule having the therapeutic agent releasably coupled thereto. The method also includes reacting the bioorthogonal molecule with a releasing molecule to separate the bioorthogonal molecule from the therapeutic agent.

In some examples of a method of administering a therapeutic agent to a subject, the bioorthogonal molecule is coupled to a carrier molecule.

In some examples of a method of administering a therapeutic agent to a subject, the therapeutic agent is released from the carrier molecule after reaction of the bioorthogonal molecule with the releasing molecule.

In some examples of a method of administering a therapeutic agent to a subject, the therapeutic agent is retained on the carrier molecule after reaction of the bioorthogonal molecule with the releasing molecule.

In some examples of a method of administering a therapeutic agent to a subject, the releasing molecule is coupled to a carrier molecule.

In some examples of a method of administering a therapeutic agent to a subject, the therapeutic agent is released from the bioorthogonal molecule after reaction of the bioorthogonal molecule with the releasing molecule coupled to the carrier molecule.

In some examples of a method of administering a therapeutic agent to a subject, the therapeutic agent is retained on the carrier molecule after reaction of the bioorthogonal molecule with the releasing molecule coupled to the carrier molecule.

EXAMPLES

Reagents and Methods

As a general overview, all chemical reagents and solvents were obtained from commercial sources (Sigma-Aldrich, Alfa-Aesar, Combi-Blocks, Acros-Organic, TCI) and used without further purification. Mass spectra were measured by the University of Utah Chemistry Mass Spectrometry Facility. Thin-layer chromatography (TLC) analysis was carried out to monitor the process of reactions. Purification of compounds was achieved by column chromatography with silica gel 300-400 mesh. $^1$H NMR and $^{13}$C NMR spectra were recorded on a Varian Mercury-400 spectrometer with chemical shifts expressed as ppm (in $CDCl_3$, MeOD-$d_4$ or DMSO-$d_6$) using $Me_4Si$ (TMS) as internal standard.

Mechanistic studies in DMSO-$d_6$ were performed by preparing stock solutions of benzonorbornadiene derivatives 1-3 (24 mM) (See FIG. 15) and DPTz (24 mM) in DMSO-$d_6$. Aliquots of the benzonorbornadiene derivatives 1-3 stock solution (125 μL) and DPTz stock solution (375 μL) were combined to give final concentrations of 6 mM for the 1-3 and 18 mM for DPTz. 18-crown-6-ether was added as internal standard for peak integration. The samples were incubated at 37° C. and $^1$H NMR spectra recorded at the indicated time points (5 min, 30 min, 2 h, 6 h and 24 h) at 25° C.

Mechanistic studies in DMSO-$d_6$/$D_2O$ (9:1, v/v) were performed by preparing stock solutions of benzonorbornadiene derivatives 2 (40 mM) and DPTz (24 mM) in DMSO-$d_6$. Aliquots of 2 stock solution (75 µL), DPTz solution (375 µL) and $D_2O$ (50 µL) were combined to give final concentrations of 6 mM for the 2 and 18 mM for DPTz. 18-crown-6-ether was added as internal standard for peak integration. The samples were incubated at 37° C. and $^1$H NMR spectra recorded at the indicated time points (5 min, 30 min, 2 h, 6 h and 24 h) at 25° C.

Characteristic peaks in $^1$H NMR of reaction mixtures were integrated in experiment performed as described for the $^1$H NMR mechanistic studies in DMSO-$d_6$/$D_2O$ (9:1, v/v). Data was acquired by $^1$H NMR monitoring at different time points (5 min, 30 min, 2 h, 6 h and 24 h) in triplicates.

pNA release was quantified by integration of characteristic $^1$H NMR peaks in experiments similar to the $^1$H NMR mechanistic studies. Aliquots of 1-3 stock solution and DPTz solution gave final concentrations of 4.5 mM for the 1-3 and 18 mM for DPTz (4 eq). 18-crown-6-ether was added as internal standard for peak integration. The samples were incubated at 37° C. and $^1$H NMR spectra recorded at the indicated time points (6 h and 24 h) at 25° C. The release studies were conducted in triplicate. The results are expressed as the mean±standard deviation (n=3).

All payload release and stability tests were performed by analytical reverse-phase HPLC (Thermo Scientific, USA) by using a LUNA C18 column (5 M, 250×10 mm, Phenomenex, USA). Specifically, stock solutions of probes 1-3 (24 mM) and tetrazine (24 mM) in DMSO were prepared. Aliquots of the benzonorbornadiene derivatives 1-3 stock solution (125 µL) and tetrazine stock solution (375 µL) were combined to give final concentrations of 6 mM for the 1-3 and 18 mM for the DPTz. Samples were incubated at 37° C. and aliquotes were taken at five time points (5 min, 30 min, 2 h, 6 h and 24 h) and diluted by 25-fold with MeCN to quench the reaction and analyzed by HPLC monitoring. (Blue line: 317 nm channel; Red line: 378 nm channel)

Release studies of prodrug 5 (See FIG. 15) were performed as follows. Stock solutions of prodrug 5 (2 mM) and PEG-Tz (16 mM) in DMSO were prepared. Aliquots of 5 stock solution (100 µL), Tz stock solution (100 µL), DMSO (300 µL) and 0.01 M PBS (500 µL) were combined to give final concentrations of 200 µM for the 5 and 1.6 mM for PEG-Tz. The sample was incubated at 37° C. in the dark and HPLC spectra were recorded at the indicated time points (5 min, 30 min, 2 h and 6 h) at 480 nm.

Stability studies of prodrug 5 in DMSO-PBS (1:1, v/v) were performed as follows. Stock solutions of prodrug 5 (2 mM) in DMSO were prepared. Aliquots of 5 stock solution (100 µL), DMSO (400 µL) and 0.01 M PBS (500 µL) were combined to give final concentrations of 200 µM for the 5 in DMSO-PBS (1:1, v/v). The sample was incubated in the dark at 37° C. and analyzed by HPLC at the indicated time points (5 min, 6 h and 24 h) at 480 nm. No free doxorubicin or doxorubicin-containing side products were observed.

Stability studies of prodrug 5 in PBS:Serum were performed as follows. Stock solutions of prodrug 5 (2.5 mM) in DMSO were prepared. Aliquots of 5 stock solution (20 µL), 0.01 M PBS (480 µL) and human serum (500 µL) (Sigma-Aldrich, USA) were combined to give final concentrations of 50 µM for the 5 in PBS: Serum (1:1, v/v). The sample was thoroughly mixed and incubated at 37° C. in the dark and subsequently a 50 µL aliquot of the sample was taken at indicated time points (5 min, 6 h, 24 h and 48 h) and quenched by 200 µL ice cold acetonitrile, followed by centrifugation at 13300 rpm for 5 min. The supernatant was injected and analyzed by HPLC at 480 nm. No free doxorubicin or doxorubicin-containing side products were observed in the stability test of 5.

Stability studies of compound 2 were performed as follows. Stock solutions of 2 (2.5 mM) in DMSO were prepared. Aliquots of 2 stock solution (20 µL), 0.01 M PBS (480 µL) and human serum (500 µL) (Sigma-Aldrich, USA) were combined to give final concentrations of 50 µM for the 2 in PBS: Serum (1:1, v/v). The sample was thoroughly mixed and incubated at 37° C. in the dark and subsequently a 50 µL aliquot of the sample was taken at indicated time points (5 min, 6 h, 24 h, 48 h, 72 h and 7 days) and quenched by 200 µL ice cold acetonitrile, followed by centrifugation at 13300 rpm for 5 min. The supernatant was injected and analyzed by HPLC at 317 nm. No free p-Nitroaniline or p-Nitroaniline-containing side products were observed in the stability test of 2.

UV-VIS photospectrometic kinetic measurements were performed on a BioTek Synergy HT Microplate Reader (BioTek, USA) in a 96-well plate formate. In further detail, for analysis of reaction kinetics in DMSO and DMSO/$H_2O$ (9:1, v/v), stock solutions of benzonorbornadiene derivatives 1-3 (60 mM or 12.5 mM) and tetrazine (15 mM or 2.5 mM) in DMSO were prepared. Final solutions containing tetrazine (2 mM or 0.25 mM) and 1-3 (20 mM, 30 mM, 40 mM and 50 mM or 2.5 mM, 3.75 mM, 5 mM, 6.25 mM) were prepared in 96-well plates and thoroughly mixed at 37° C. for UV-Vis measurements. For analysis of reaction kinetics in DMSO/PBS (3:2, v/v), final solutions containing tetrazine (0.05 mM) and 1-2 (0.5 mM), tetrazine alone (0.05 mM) were prepared in 96-well plates and thoroughly mixed at 37° C. for UV-Vis measurements. The reactions were monitored at 525 nm, which is a local absorbance maximum of tetrazine. All kinetic experiments were run in triplicates. Pseudo-first order curve fitting was performed with Origin 8.0 software using the exponential formula: $y = A_1 x e^{kx} + y_0$.

Cell proliferation assays were performed on an Envision 2104 Multilabel Reader (PerkinElmer, USA). Specifically, A549 lung cancer cells (ATCC, USA) were maintained in a humidified $CO_2$ (5%) incubator at 37° C. in DMEM (Thermo Fisher, USA) supplemented with 10% fetal bovine serum in the presence of 1% Penicillin-Streptomycin-Glutamine (Thermo Fisher, USA) and 0.2% Normocin (InvivoGen, USA). The cells were plated in 96-well TC treated plates (PerkinElmer, USA) at a 5000 cells/well density 24 h prior to the experiment. Prodrug 5, compound 2 (2 mM in DMSO) and PEG-Tz (40 mM in DMSO) were serially diluted in pre-warmed culture medium. Prodrug 5 and compound 2 are in a series of final concentrations ranging from 0.001 to 10 µM with 200 µM, 100 µM, 50 µM, 25 µM PEG-Tz before the experiment and added to the wells (100 µL final volume per well). Doxorubicin was used as the positive control with same series of concentrations ranging from 0.001 to 10 µM. PEG-Tz was also tested with same series of concentrations ranging from 0.02 to 200 µM, no obvious toxicity was observed. After 72 h incubation at 37° C., cell proliferation was assessed by a CellTiter-Glo® viability assay. Lyophilized CellTiter Glo Substrate (Promega, USA) was dissolved in the CellTiter Glo Buffer to get CellTiter-Glo® Reagent, and from which 100 µL was added to each well. After 15 min incubation at 25° C., the medium was gently measured with Envision 2104 Multilabel Reader (PerkinElmer, USA) to get the luminescent based on quantitation of the ATP present, an indicator of metabolically active cells. The proliferation assay was performed in triplicate (n=3). $EC_{50}$ values were derived from the normalized cell growth and corresponding sigmoidal curves were fitted and generated with Origin 8.0.

Synthetic Reactions

Figure 14A:
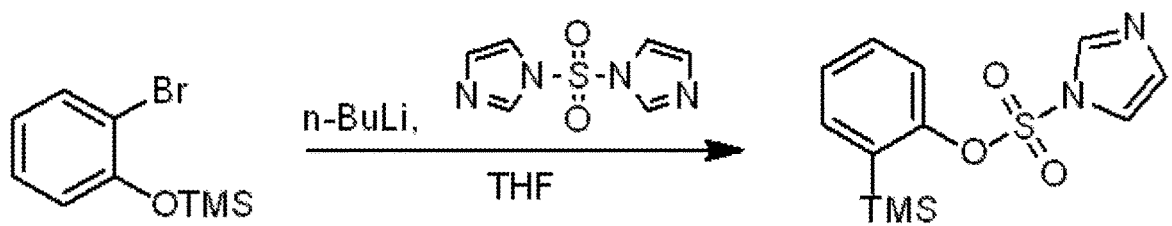
FIGS. 14A-14S illustrate individual reaction schemes for compounds of interest.

Compounds used in the present example were synthesized as follows:

2-(Trimethylsilyl)phenyl imidazolsulfonate 2-(Trimethylsilyl)phenyl imidazolsulfonate was prepared as illustrated in FIG. 14A.

$^1$H NMR (400 MHz, CDCl$_3$) δ 7.92 (s, 1H), 7.54-7.53 (m, 1H), 7.39 (s, 1H), 7.32-7.22 (m, 3H), 6.50 (t, J=4.4 Hz, 1H), 0.35 (s, 9H). The $^1$H NMR data agreed with reported spectra of this compound.

1,4-dihydro-1,4-epoxynaphthalen-1-yl)methanol (1d)

Figure 14B:
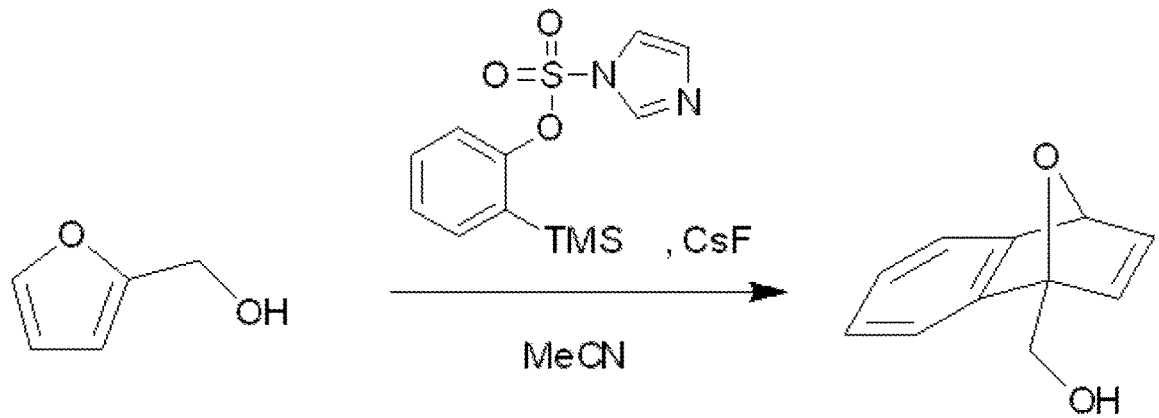

1,4-dihydro-1,4-epoxynaphthalen-1-yl)methanol was prepared according to the reaction scheme presented in FIG. 14B. In further detail, to a solution of 2-(trimethylsilyl)phenyl imidazolsulfonate (2.37 g, 8.0 mmol) and furan-2-ylmethanol (1a; 1.26 g, 12.8 mmol) in anhydrous MeCN (30 mL) was added CsF (2.43 g, 16 mmol). The reaction mixture was heated and maintained at 50° C. for 8 h. The mixture was extracted with EtOAc (250 mL) and washed with water (2×150 mL). The separated organic layer was again washed with brine (3×150 mL) and concentrated under reduced pressure. The crude was purified by column chromatography (hexane:EtOAc=3:1, v/v) to give the desired product as a yellow solid in a yield of 510 mg (36%).

$^1$H NMR (400 MHz, CDCl$_3$) δ 7.24-7.22 (m, 1H), 7.18-7.16 (m, 1H), 7.05 (dd, J$_1$=1.6 Hz, J$_2$=5.6 Hz, 1H), 6.98-6.96 (m, 2H), 6.88 (d, J=5.2 Hz, 1H), 5.70 (d, J=1.6 Hz, 1H), 4.48-4.37 (m, 2H), 2.58 (t, d, J=6.0 Hz, 1H). $^{13}$C NMR (100 MHz, CDCl$_3$) δ 150.5, 147.8, 144.9, 142.4, 125.2, 125.1, 120.2, 119.6, 93.7, 82.2, 60.3. HRMS (ESI): calcd. for C$_{11}$H$_{10}$O$_2$[M+Na]$^+$ 197.0578, found 197.0583.

1,4-dihydro-1,4-epoxynaphthalen-1-yl)methyl (4-nitrophenyl)carbamate (1)

Figure 14C:
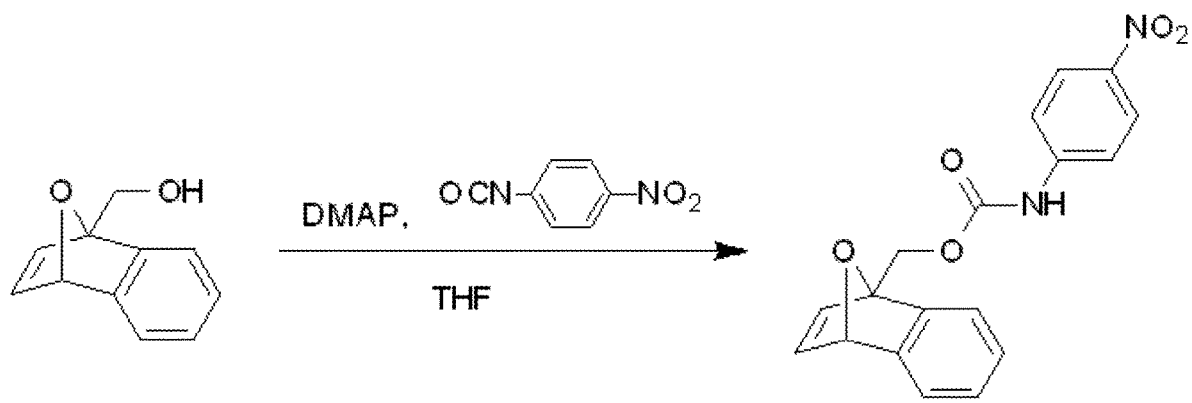

1,4-dihydro-1,4-epoxynaphthalen-1-yl)methyl (4-nitrophenyl)carbamate was prepared according to the reaction scheme presented in FIG. 14C. In further detail, to a solution of 1d (556 mg, 3.2 mmol) and DMAP (507 mg, 4.16 mmol) in anhydrous THF (40 mL) was added 4-nitrophenyl isocyanate (1.3 g, 8.0 mmol). The reaction mixture was stirred at 50° C. for 12 h. The mixture was diluted with EtOAc (150 mL) and washed with water (2×100 mL) and brine (3×150 mL). The separated organic layer was dried with Na$_2$SO$_4$ and concentrated under reduced pressure. The crude compound was purified by column chromatography (hexane:EtOAc=3:1, v/v) to afford the desired compound as a yellow solid in a yield of 180 mg (29%).

$^1$H NMR (400 MHz, CDCl$_3$) δ 8.21 (d, J=9.2 Hz, 2H), 7.55 (d, J=8.8 Hz, 2H), 7.31-7.28 (m, 1H), 7.22-7.20 (m, 1H), 7.16-7.13 (m, 2H), 7.03-7.01 (m, 2H), 6.89 (d, J=5.6 Hz, 1H), 5.77 (d, J=1.6 Hz, 1H), 5.16 (d, J=12.8 Hz, 1H), 5.02 (d, J=13.2 Hz, 1H). $^{13}$C NMR (100 MHz, CDCl$_3$) δ 152.4, 149.8, 147.1, 145.3, 143.5, 141.6, 125.5, 125.3, 125.2, 120.5, 119.4, 117.8, 91.1, 82.4, 62.4. HRMS (ESI): calcd. for C$_{18}$H$_{14}$N$_2$O$_5$ [M+Na]$^+$ 361.0800, found 361.0804.

Figure 14D:
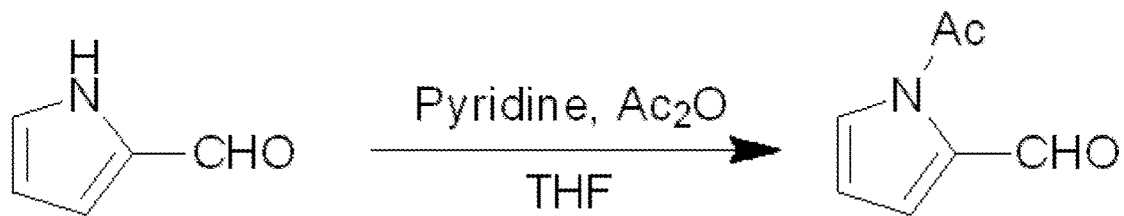

1-acetyl-1H-pyrrole-2-carbaldehyde 1-acetyl-1H-pyrrole-2-carbaldehyde was prepared as illustrated in the scheme represented in FIG. 14D.

$^1$H NMR (400 MHz, CDCl$_3$) δ 10.29 (s, 1H), 7.33 (dd, J$_1$=1.6 Hz, J$_2$=2.8 Hz, 1H), 7.21 (dd, J=1.6 Hz, J$_2$=4.0 Hz, 1H), 6.35 (t, J=3.2 Hz, 1H), 2.66 (s, 3H). The $^1$H NMR data agreed with reported spectra of this compound.

1-(2-(hydroxymethyl)-1H-pyrrol-1-yl)ethanone (2a)

Figure 14E:
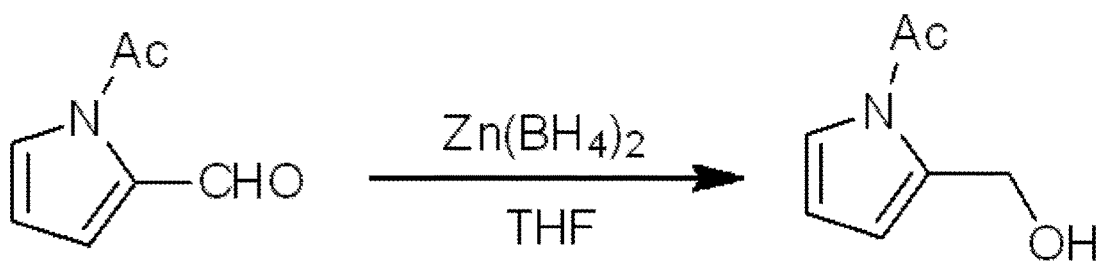

1-(2-(hydroxymethyl)-1H-pyrrol-1-yl)ethanone (2a) was prepared as illustrated in the scheme represented in FIG. 14E.

$^1$H NMR (400 MHz, CDCl$_3$) δ 7.06 (d, J=1.6 Hz, J$_2$=3.2 Hz, 1H), 6.21-6.19 (m, 2H), 4.61 (s, 2H), 2.57 (s, 3H). $^{13}$C NMR (100 MHz, CDCl$_3$) δ 171.5, 135.4, 121.7, 114.7, 112.2, 57.8, 23.7. The $^1$H NMR data agreed with reported spectra of this compound.

1-(2-(((tert-butyldimethylsilyl)oxy)methyl)-1H-pyrrol-1-yl)ethanone (2b)

Figure 14F:
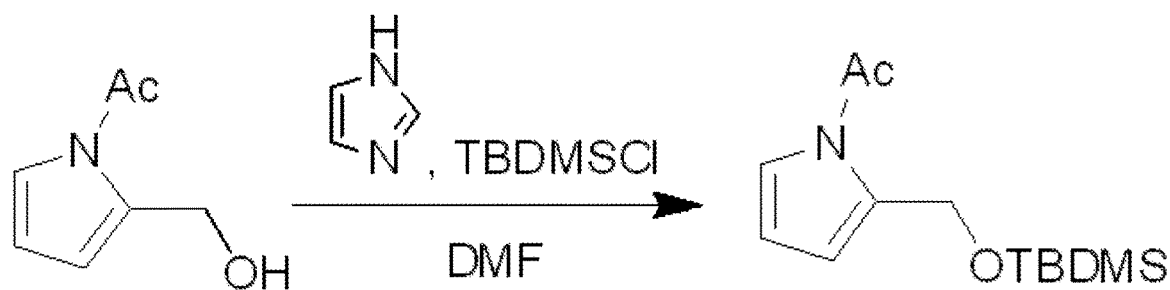

1-(2-(((tert-butyldimethylsilyl)oxy)methyl)-1H-pyrrol-1-yl)ethenone was prepared according to the reaction scheme illustrated in FIG. 14F. In further detail, to a solution of 2a (1.2 g, 8.6 mmol) and imidazole (877 mg, 12.9 mmol) in anhydrous DMF (10 mL) was added tert-butylchlorodimethylsilane (1.52 g, 10.3 mmol) at 0° C. The reaction mixture was warmed to room temperature and kept at this temperature for 3 h. The reaction was quenched with sat. aq. NaHCO$_3$ solution (200 mL), diluted with water (150 mL) and extracted with EtOAc (2×150 mL). The combined organic layers were washed with brine (150 mL), dried over Na$_2$SO$_4$ and concentrated under reduced pressure. The crude product was purified by column chromatography (hexane:EtOAc=20:1, v/v) to give the product as a brown oil in a yield of 1.25 g (58%).

$^1$H NMR (400 MHz, CDCl$_3$) δ 7.06-7.04 (m, 1H), 6.31-6.30 (m, 1H), 6.22 (t, J=3.2 Hz, 1H), 4.94 (brs, 2H), 2.53 (s, 3H), 0.93 (s, 9H), 0.09 (s, 6H). $^{13}$C NMR (100 MHz, CDCl$_3$) δ 169.0, 136.9, 120.3, 112.0, 111.5, 60.7, 25.9, 23.5, 18.4, −5.4. HRMS (ESI): calcd. for C$_{13}$H$_{23}$NO$_2$Si [M+Na]$^+$ 276.1396, found 276.1398.

1-(((tert-butyldimethylsilyl)oxy)methyl)-1,4-dihydro-1,4-epiminonaphthalen-9-yl)ethanone (2c)

Figure 14G:
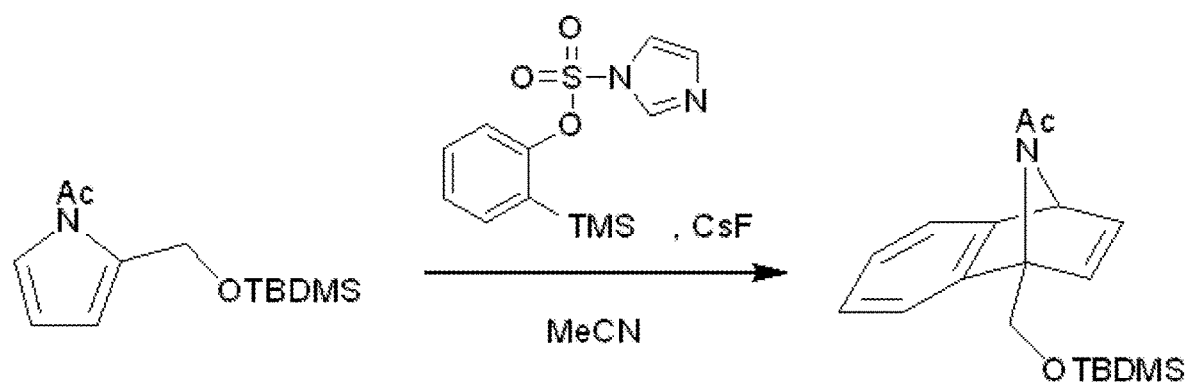

1-(((tert-butyldimethylsilyl)oxy)methyl)-1,4-dihydro-1,4-epiminonaphthalen-9-yl)ethenone was prepared according to the reaction scheme illustrated in FIG. 14G. In further detail, to a solution of 2-(trimethylsilyl)phenyl imidazolsulfonate (0.98 g, 3.3 mmol) and 2b (1.25 g, 5 mmol) in anhydrous MeCN (20 mL) was added CsF (1 g, 6.6 mmol). The reaction mixture was heated and maintained at 60° C. for 12 h. The mixture was diluted with EtOAc (150 mL) and washed with water (2×50 mL). The separated organic layer was again washed with brine (2×150 mL) and concentrated under reduced pressure. The crude was purified by column chromatography (hexane:EtOAc=2:1, v/v) to give the product as a brown oil in a yield of 350 mg (32%).

$^1$H NMR (400 MHz, CDCl$_3$) δ 7.46 (d, J=8.0 Hz, 1H), 7.21 (d, J=8.0 Hz, 1H), 7.14 (brs, 1H), 7.00-6.93 (m, 3H), 5.41 (s, 1H), 4.96 (d, J=8.0 Hz, 1H), 4.68 (d, J=8.0 Hz, 1H), 1.93 (s, 3H), 0.96 (s, 9H), 0.21 (s, 3H), 0.19 (s, 3H). $^{13}$C NMR (100 MHz, CDCl$_3$) δ 167.5, 151.1, 148.5, 145.5, 141.2, 125.2, 124.7, 121.2, 119.7, 77.1, 67.1, 60.9, 25.9, 22.7, 18.2, −5.3, −5.4, −5.5. HRMS (ESI): calcd. for C$_{19}$H$_{27}$NO$_2$Si [M+Na]$^+$ 352.1709, found 352.1716.

1-(hydroxymethyl)-1,4-dihydro-1,4-epiminonaphthalen-9-yl)ethanone (2d)

Figure 14H:
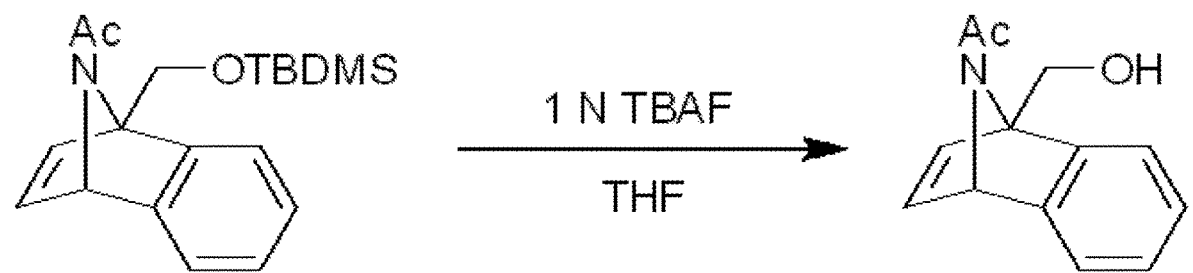

1-(hydroxymethyl)-1,4-dihydro-1,4-epiminonaphthalen-9-yl)ethenone was prepared according to the reaction scheme illustrated in FIG. 14H. In further detail, to a solution of 2c (350 mg, 1.1 mmol) in THF (4 mL) was added 1 M tetra n-butyl ammonium fluoride (2 mL. 2 mmol) at room temperature, and the mixture was stirred for 2 h. The mixture was diluted with Et$_2$O/EA mixture (100 mL, 1:1) and washed with water (50 mL) and brine (2×50 mL) and the separated organic layer was dried with Na$_2$SO$_4$, and concentrated under reduced pressure. The crude product was purified by column chromatography (hexane:EtOAc=10:1, v/v) to afford the product as a brown oil in a yield of 200 mg (85%).

$^1$H NMR (400 MHz, CDCl$_3$) δ 7.29-7.26 (m, 2H), 7.08-7.06 (m, 1H), 7.04-7.00 (m, 2H), 6.93 (d, J=5.6 Hz, 1H), 5.51 (d, J=2.4 Hz, 1H), 5.30-5.26 (m, 1H), 4.59 (dd, J,=3.2 Hz, J$_2$=7.2 Hz, 2H), 2.05 (s, 3H). $^{13}$C NMR (100 MHz, CDCl$_3$) δ 164.8, 148.2, 147.8, 145.4, 143.3, 125.5, 125.3, 120.5, 120.2, 79.0, 66.8, 58.0, 22.3. HRMS (ESI): calcd. for C$_{13}$H$_{13}$NO$_2$ [M+Na]$^+$ 238.0844, found 238.0842.

9-acetyl-1,4-dihydro-1,4-epiminonaphthalen-1-yl) methyl (4-nitrophenyl)carbamate (2)

Figure 14I:
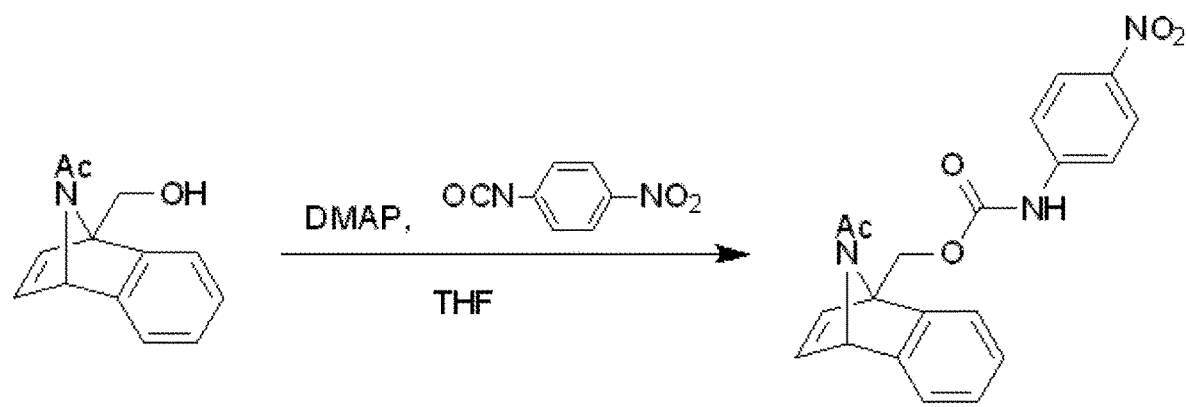

9-acetyl-1,4-dihydro-1,4-epiminonaphthalen-1-yl)methyl (4-nitrophenyl)carbamate was prepared according to the reaction scheme illustrated in FIG. 14I. In further detail, to a solution of 2d (200 mg, 0.9 mmol) and DMAP (146 mg, 1.2 mmol) in anhydrous THF (12 mL) was added 4-nitrophenyl isocyanate (300 mg, 2 mmol). The reaction mixture was stirred at 50° C. for 10 h. The mixture was diluted with EtOAc (150 mL) and washed with water (200 mL) and brine (2×150 mL). The separated organic layer was dried with Na$_2$SO$_4$, and concentrated under reduced pressure, purified by column chromatography (hexane:EtOAc=5:1, v/v) to afford the desired compound as yellow solid in a yield of 70 mg (22%).

$^1$H NMR (400 MHz, DMSO-d$_6$) δ 10.50 (s, 1H), 8.22 (d, J=9.6 Hz, 2H), 7.76 (d, J=9.6 Hz, 2H), 7.37-7.35 (m, 2H), 7.18-7.16 (m, 1H), 7.06 (d, J=5.6 Hz, 1H), 7.01-6.99 (m, 2H), 5.84 (d, J=2.4 Hz, 1H), 5.40-5.30 (m, 2H), 1.89 (s, 3H). $^{13}$C NMR (100 MHz, DMSO-d$_6$) δ 169.3, 153.6, 149.7, 149.3, 146.1, 144.9, 143.9, 142.2, 125.5, 125.2, 121.0, 120.6, 118.2, 75.3, 67.0, 62.2, 23.4. HRMS (ESI): calcd. for C$_{20}$H$_{17}$N$_3$O$_5$[M+Na]$^+$ 402.1066, found 402.1075.

Tert-butyl 2-formyl-1H-pyrrole-1-carboxylate

Figure 14J:
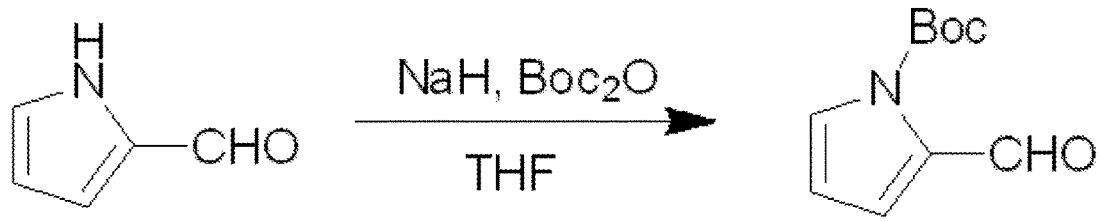

Tert-butyl 2-formyl-1H-pyrrole-1-carboxylate was prepared as illustrated in the scheme depicted in FIG. 14J.

$^1$H NMR (400 MHz, CDCl$_3$) δ 10.23 (s, 1H), 7.34 (brs, 1H), 7.06 (brs, 1H), 6.18 (t, J=4.0 Hz, 1H), 1.55 (s, 9H). The $^1$H NMR data agreed with reported spectra of this compound.

Tert-butyl 2-(hydroxymethyl)-1H-pyrrole-1-carboxylate (3a)

Figure 14K:
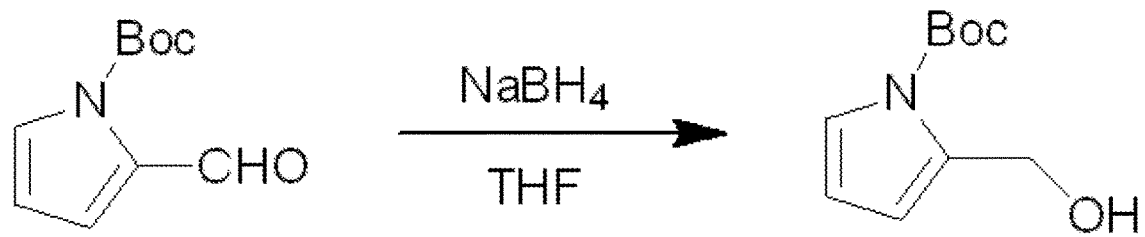

Tert-butyl 2-(hydroxymethyl)-1H-pyrrole-1-carboxylate (3a) was prepared as illustrated in the scheme depicted in FIG. 14K.

$^1$H NMR (400 MHz, CDCl$_3$) δ 7.16 (d, J=1.2 Hz, 1H), 6.18 (brs, 1H), 6.10 (brs, 1H), 4.64 (d, J=7.6 Hz, 2H), 3.60 (d, J=7.2 Hz, 1H), 1.61 (s, 9H). $^{13}$C NMR (100 MHz, CDCl$_3$) δ 150.0, 134.8, 121.9, 113.6, 110.4, 84.5, 57.7, 28.0. The $^1$H NMR data agreed with reported spectra of this compound.

Tert-butyl 2-(((tert-butyldimethylsilyl)oxy)methyl)-1H-pyrrole-1-carboxylate (3b)

Figure 14L:

Tert-butyl 2-(((tert-butyldimethylsilyl)oxy)methyl)-1H-pyrrole-1-carboxylate was prepared according to the reaction scheme illustrated in FIG. 14L. In further detail, to a solution of 3a (7.0 g, 35.5 mmol) and imidazole (3.6 g, 53 mmol) in anhydrous DMF (30 mL) was added tert-butylchlorodimethylsilane (6.5 g, 44 mmol) at 0° C. The reaction mixture was allowed to warm to room temperature and stirred for 12 h. The reaction mixture was extracted with DCM (300 mL), quenched with sat. aq. NaHCO$_3$ solution (150 mL), and washed with water (2×200 mL). The combined organic layers were washed with brine (2×200 mL), dried over Na$_2$SO$_4$ and concentrated under reduced pressure. The crude product was purified by column chromatography (hexane:EtOAc=20:1, v/v) to give the product as a brown oil in a yield of 8.8 g (80%).

Figure 14M:
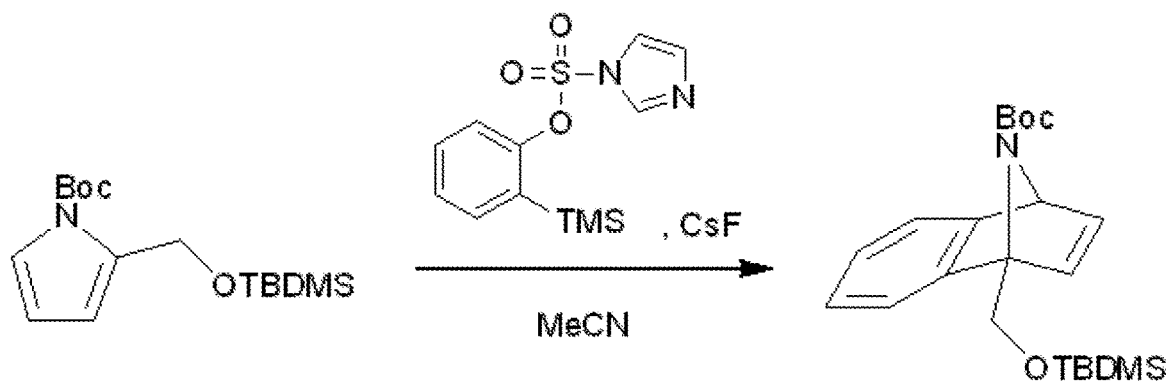

$^1$H NMR (400 MHz, CDCl$_3$) δ 7.19 (t, J=2.4 Hz, 1H), 6.23 (brs, 1H), 6.13 (t, J=3.2 Hz, 1H), 4.89 (s, 2H), 1.59 (s, 9H), 0.93 (s, 9H), 0.09 (s, 6H). $^{13}$C NMR (100 MHz, CDCl$_3$) δ 149.2, 135.4, 120.9, 111.0, 110.3, 83.5, 60.2, 27.9, 25.9, 18.4, −5.4. HRMS (ESI): calcd. for C$_{16}$H$_{29}$NO$_3$Si [M+Na]$^+$ 334.1814, found 334.1815.

tert-butyl-1-(((tert-butyldimethylsilyl)oxy)methyl)-1,4-dihydro-1,4-epiminonaphthalene-9-carboxylate (3c)

tert-butyl-1-(((tert-butyldimethylsilyl)oxy)methyl)-1,4-dihydro-1,4-epiminonaphthalene-9-carboxylate was prepared according to the reaction scheme illustrated in FIG. 14M. In further detail, to a solution of 2-(trimethylsilyl)phenyl imidazolsulfonate (4.5 g, 15 mmol) and 3b, (7.2 g, 22.8 mmol) in anhydrous MeCN (60 mL) was added CsF (4.7 g, 30 mmol). The reaction was maintained at 60° C. for 12 h. The mixture was diluted with EtOAc (150 mL) and washed with water (100 mL). The separated organic layer was washed with brine (2×100 mL), dried with Na$_2$SO$_4$ and concentrated by reduced pressure. The crude was purified by column chromatography (hexane:EtOAc=100:1 to 50:1, v/v) to give the product as a brown oil in a yield of 1.2 g (20%).

Figure 14N:
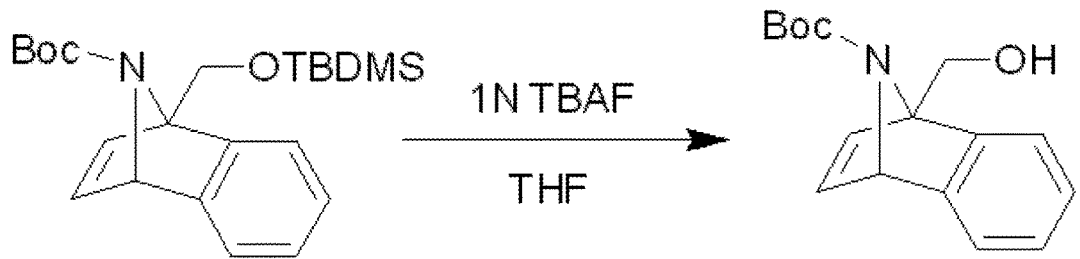

$^1$H NMR (400 MHz, CDCl$_3$) δ 7.42 (d, J=6.0 Hz, 1H), 7.22 (d, J=6.0 Hz, 1H), 7.06 (d, J=5.2 Hz, 1H), 6.95 (t, J=6.0 Hz, 3H), 5.44 (s, 1H), 4.78 (brs, 1H), 4.55 (d, J=9.6 Hz, 1H), 1.32 (s, 9H), 0.96 (s, 9H), 0.20 (s, 3H), 0.19 (s, 3H). $^{13}$C NMR (100 MHz, CDCl$_3$) δ 154.8, 150.5, 149.5, 144.4, 141.6, 141.5, 124.9, 124.6, 120.9, 120.8, 120.5, 80.5, 67.4, 61.4, 29.7, 28.1, 25.9, 18.3, −5.3, −5.4. HRMS (ESI): calcd. for C$_{22}$H$_{33}$NO$_3$Si [M+Na]$^+$ 410.2127, found 410.2138. tert-butyl 1-(hydroxymethyl)-1,4-dihydro-1,4-epiminonaphthalene-9-carboxylate (3d) tert-butyl-1-(hydroxymethyl)-1,4-dihydro-1,4-epiminonaphthalene-9-carboxylate was prepared according to the reaction scheme illustrated in FIG. 14N. In further detail, to a solution of 3c (1.1 g, 3.0 mmol) in anhydrous THF (7 mL) was added 1 M tetra n-butyl ammonium fluoride (4.8 mL, 4.8 mmol) at room temperature and the mixture was stirred for 8 h. The mixture was extracted with Et$_2$O/EtOAc mixture (50+50 mL) and washed with water (2×50 mL). The separated organic layer was again washed with brine (2×50 mL), dried with Na$_2$SO$_4$ and concentrated under reduced pressure. The crude compound was purified by column chromatography (hexane:EtOAc=10:1, v/v) to afford the product as a brown oil in a yield of 0.7 g (85%).

Figure 14O:
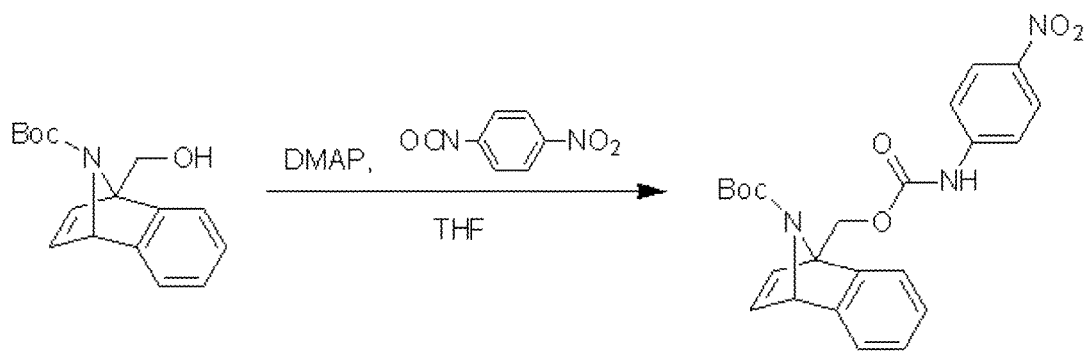

$^1$H NMR (400 MHz, CDCl$_3$) δ 7.24 (t, J=5.2 Hz, 2H), 7.04-6.98 (m, 3H), 6.88 (d, J=5.2 Hz, 1H), 5.51 (brs, 1H), 4.58 (d, J=6.8 Hz, 2H), 1.42 (s, 9H). $^{13}$C NMR (100 MHz, CDCl$_3$) δ 148.8, 148.1, 144.4, 144.0, 125.1, 125.0, 120.5, 120.1, 81.6, 78.6, 66.9, 58.9, 28.2, 25.6. HRMS (ESI): calcd. for C$_{16}$H$_{19}$NO$_3$ [M+Na]$^+$ 296.1263, found 296.1267.

tert-butyl 1-((((4-nitrophenyl)carbamoyl)oxy)methyl)-1,4-dihydro-1,4-epiminonaphthalene-9-carboxylate (3)

tert-butyl-1-((((4-nitrophenyl)carbamoyl)oxy)methyl)-1,4-dihydro-1,4-epiminonaphthalene-9-carboxylate was prepared according to the reaction scheme illustrated in FIG. 14O. In further detail, to a solution of 3d (408 mg, 1.5 mmol) and DMAP (244 mg, 2 mmol) in THF (25 mL) was added 4-nitrophenyl isocyanate (450 mg, 3 mmol). The reaction was stirred at 50° C. for 10 h. The mixture was diluted with EtOAc (150 mL) and washed with water (200 mL) and brine (2×150 mL). The separated organic layer was dried with Na$_2$SO$_4$, concentrated under reduced pressure and purified by column chromatography (hexane:EtOAc=5:1, v/v) to afford the desired compound as a yellow solid in a yield of 405 mg (62%).

$^1$H NMR (400 MHz, CDCl$_3$) δ 8.21 (d, J=9.2 Hz, 2H), 7.57 (d, J=9.2 Hz, 2H), 7.31-7.29 (m, 1H), 7.24-7.22 (m, 2H), 7.08-7.06 (m, 1H), 7.03-6.98 (m, 2H), 6.84 (d, J=5.6 Hz, 1H), 5.55 (d, J=2.0 Hz, 1H), 5.40 (brs, 2H), 1.36 (s, 9H). $^{13}$C NMR (100 MHz, CDCl$_3$) δ 154.8, 152.6, 148.6, 147.9, 143.9, 142.9, 126.3, 125.4, 125.2, 125.1, 121.1, 119.8, 117.7, 81.4, 75.6, 67.4, 62.2, 28.1. HRMS (ESI): calcd. for C$_{23}$H$_{23}$N$_3$O$_6$ [M+Na]$^+$ 460.1485, found 460.1495.

Doxorubicin-containing Prodrug (5)

Figure 14P:
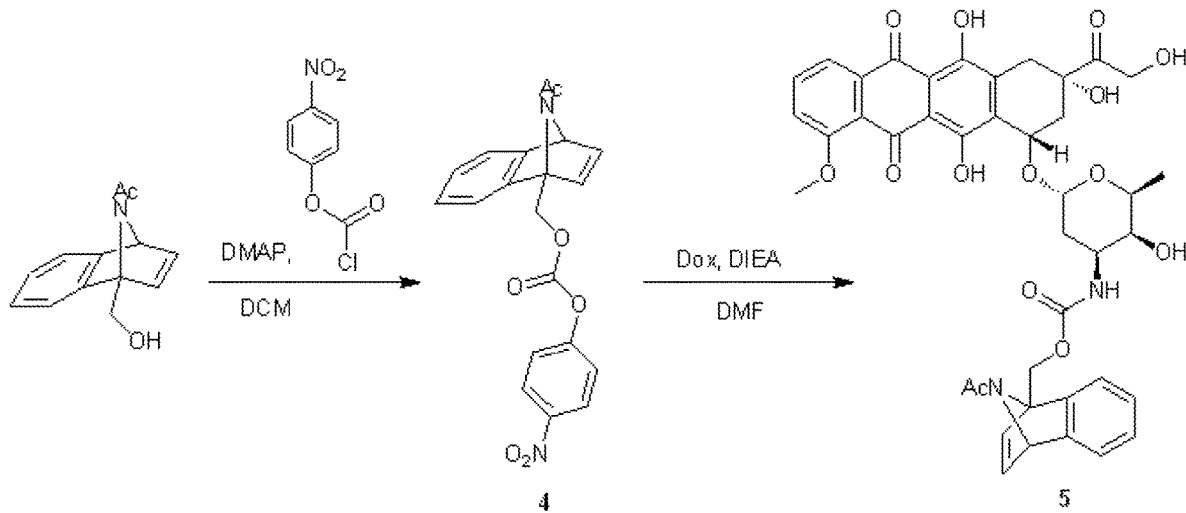

The doxorubicin-containing prodrug was prepared according to the reaction scheme illustrated in FIG. 14P. In further detail, to a solution of 2d (53 mg, 0.24 mmol) in dry DCM (6 mL) was added DMAP (0.5 mmol, 70 mg) and nitrophenyl chloroformate (71 mg, 0.35 mmol) at 0° C. The reaction was kept in the dark at 25° C. overnight. The reaction mixture was quenched with ice and extracted with DCM (2×20 mL). The combined organic layer was washed with water (3×50 mL) and brine (3×50 mL) until no more yellow color was observed in the organic phase, dried over Na$_2$SO$_4$ and concentrated to afford the carbonate intermediate (4) as light yellow solid in a yield of 65 mg (64%). 4 decomposed upon storage and was immediately used in the next step.

$^1$H NMR (400 MHz, CDCl$_3$) δ 7.29 (dd, J$_1$=2.0 Hz, J$_2$=6.8 Hz, 2H), 7.44 (dd, J$_1$=2.0 Hz, J$_2$=6.8 Hz, 2H), 7.31-7.26 (m, 2H), 7.10-7.08 (m, 1H), 7.04-6.99 (m, 3H), 5.65-5.62 (m, 1H), 5.67 (s, 1H), 5.53 (d, J=7.6 Hz, 1H), 1.99 (s, 3H).

To a solution of 4 (64 mg, 0.17 mmol) in dry DMF (0.5 mL) was added DIEA (272 mg, 2.1 mmol), after 15 min, doxorubicin hydrochloride (120 mg, 0.2 mmol) was added and the reaction mixture was stirred in the dark and at 25° C. for 24 h. The mixture was diluted with DCM (100 mL) and washed with H$_2$O (50 mL) and brine (2×50 mL). The organic phase was concentrated and purified by preparatory-TLC (DCM:MeOH=15:1, v/v) to afford the desired compound as red solid in a yield of 40 mg (30%).

$^1$H NMR (400 MHz, CDCl$_3$:MeOD-d$_4$=9:1) δ 7.97 (dd, J$_1$=1.2 Hz, J$_2$=8.0 Hz, 1H), 7.73 (t, J=8.0 Hz, 1H), 7.34 (d, J=8.4 Hz, 1H), 7.17 (brs, 2H), 6.95-6.90 (m, 2H), 6.81 (brs, 1H), 6.74 (brs, 1H), 5.42 (brs, 2H), 5.23 (d, J=15.2 Hz, 2H), 5.11 (d, J=11.6 Hz, 1H), 4.71 (s, 2H), 4.08 (d, J=6.4 Hz, 1H), 4.01 (s, 3H), 3.79 (d, J=12.0 Hz, 1H), 3.62 (s, 1H), 3.20 (d, J=18.8 Hz, 1H), 2.98 (d, J=18.8 Hz, 1H), 2.30 (d, J=15.2 Hz, 1H), 2.09 (d, J=15.2 Hz, 1H), 1.89 (d, J=4.0 Hz, 3H), 1.80-1.74 (m, 2H), 1.23 (d, J=6.4 Hz, 3H). $^{13}$C NMR (126 MHz, DMSO-d$_6$) 214.3, 186.9, 186.8, 169.3, 161.2, 156.6, 155.7, 154.9, 150.3, 144.7, 143.5, 136.6, 135.9, 135.1, 134.5, 125.3, 125.1, 120.9, 120.6, 120.4, 120.2, 119.4, 111.2, 111.0, 100.8, 75.4, 70.3, 68.4, 67.1, 67.0, 64.2, 61.3, 57.0, 55.4, 47.7, 37.0, 32.5, 30.3, 23.2, 17.5. HRMS (ESI): calcd. for C$_{41}$H$_{40}$N$_2$O$_{14}$ [M+Na]$^+$ 807.2377, found 807.2383.

3,6-di(pyridin-2-yl)pyridazine (DPPz)

Figure 14Q:
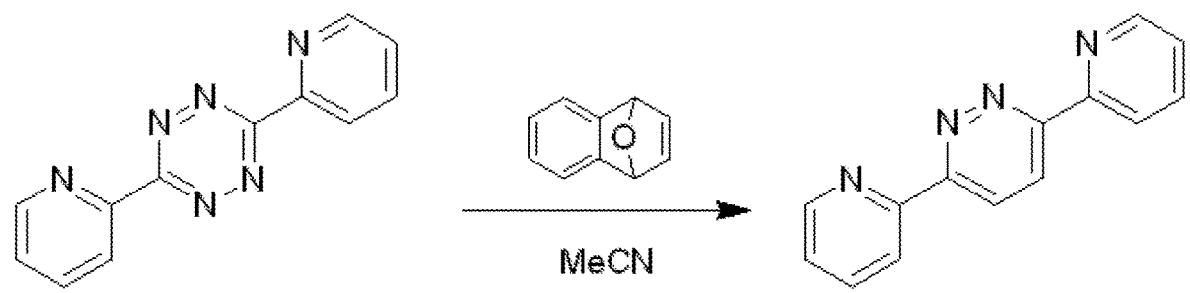

DPPz was prepared according to the reaction scheme illustrated in FIG. 14Q. In further detail, to a solution of 1,4-epoxynaphthalene (72 mg, 0.5 mmol) in MeCN (12 mL) was added a solution of 3,6-di(pyridin-2-yl)-1,2,4,5-tetrazine (118 mg, 0.5 mmol) in MeCN (12 mL). The reaction was stirred at 40° C. for 4 h. The mixture was concentrated and purified by column chromatography (hexane:EtOAc=1:1, v/v) to afford the desired compound as a pale solid in a yield of 60 mg (49%).

$^1$H NMR (400 MHz, DMSO-d$_6$) δ 8.80 (d, J=3.6 Hz, 2H), 8.69 (s, 2H), 8.65 (d, J=6.4 Hz, 2H), 8.08 (t, J=6.4 Hz, 2H), 7.61-7.59 (m, 2H). The $^1$H NMR agreed with reported spectra of this compound.

Figure 14R:
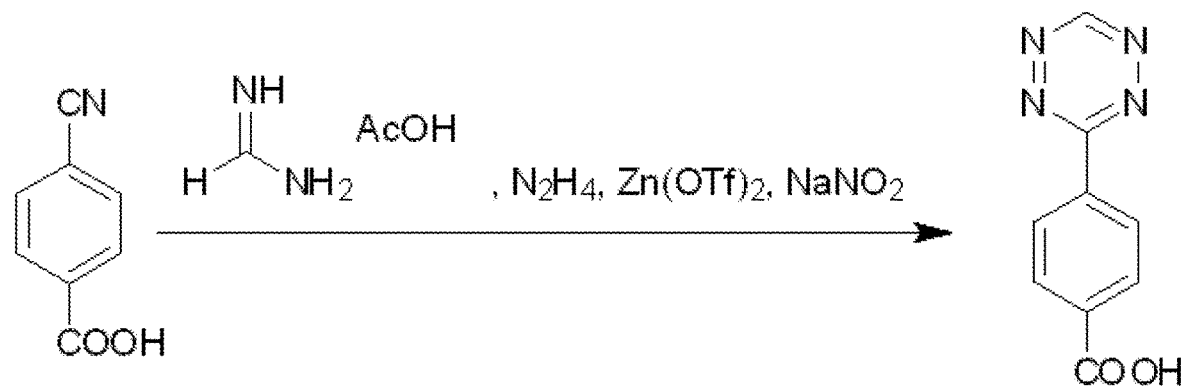

4-(1,2,4,5-tetrazin-3-yl)benzoic acid 4-(1,2,4,5-tetrazin-3-yl)benzoic acid was synthesized as illustrated in the scheme depicted in FIG. 14R.

$^1$H NMR (400 MHz, DMSO-d$_6$) δ 10.65 (s, 1H), 8.64-8.57 (m, 2H), 8.24-8.17 (m, 2H). The $^1$H NMR data agreed with reported spectra of this compound.

N-(2-(2-(2-methoxyethoxy)ethoxy)ethyl)-4-(1,2,4,5-tetrazin-3-yl) benzamide (PEG-Tz)

Figure 14S:
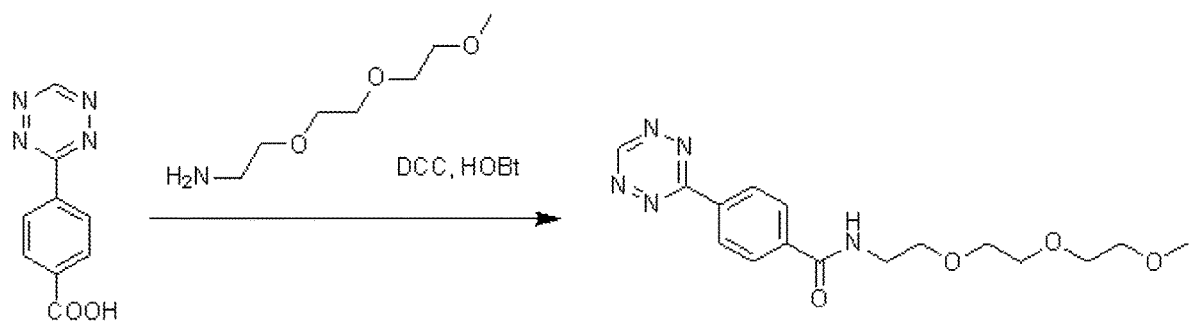

PEG-Tz was prepared according to the reaction scheme illustrated in FIG. 14S. In further detail, to a dry round-bottom flask was added 2-(2-(2-methoxyethoxy)ethoxy)ethan-1-amine (190 mg, 1.19 mmol) in THF (0.5 mL), dicyclohexylmethanediimine (230 mg, 1.09 mmol) in THF (1.0 mL), and hydroxybenzotriazole (170 mg, 1.09 mmol) in THF (1 mL). The solution was cooled to 0° C. in an ice bath and stirred. 4-(1,2,4,5-tetrazin-3-yl)benzoic acid (200 mg, 0.99 mmol) in THF (2.5 mL) was added to the flask while allowing the reaction mixture to return to room temperature and the resultant red reaction mixture was stirred for 20 h. After the allotted time, the reaction was diluted with 10 mL of diethyl ether to precipitate out the dicyclohexylurea byproduct, which was removed by filtration; the solution was subsequently washed with diethyl ether (2×5 mL), filtered again, and concentrated. The mixture was directly concentrated and purified by column chromatography (DCM:Acetone=10:1, v/v) to afford the desired compound as a pink solid in a yield of 80 mg (20%)

$^1$H NMR (400 MHz, CDCl$_3$) δ 10.27 (s, 1H), 8.75-8.67 (m, 2H), 8.09-8.01 (m, 2H), 7.00 (s, 1H), 3.77-3.62 (m, 9H), 3.58-3.51 (m, 2H), 3.33 (s, 3H). $^{13}$C NMR (100 MHz, CDCl$_3$) δ 166.4, 165.9, 157.9, 138.7, 134.0, 128.4, 128.1, 71.9, 70.6, 70.5, 70.2, 69.7, 39.9. HRMS (ESI): calcd. for $C_{16}H_{21}N_5O_4$ [M+Na]$^+$ 370.1491, found 370.1496.

Results

Benzonorbornadiene (BNBD) derivatives are described in this example as stable carrier molecules that rapidly react with Tz to quantitatively release a cargo molecule (e.g. cytotoxic agent, optical reporter). This molecular design is based on the intrinsic lability of isobenzofurans, isoindoles, and the like, which can be harnessed to near-instantaneously liberate a cargo molecule. Further, such self-immolative heterocycles are readily accessible from the reaction of BNBDs and Tz. In particular, the proposed release molecules can include 7-aza/oxa-BNBDs with carbamate leaving groups, or other suitable leaving group as described above, attached via a methylene linker, or other suitable linker as described above, to the bridgehead carbon (See FIG. 15 for Scheme 1). For example, the reaction of 7-aza/oxa-BNBDs with Tz generates an intermediate (I1), which rapidly eliminates $N_2$, followed by a retro Diels-Alder cycloreversion, generating isoindoles/isobenzofurans (13). These heterocycles in turn eliminate a carbamate to liberate the free amine (Scheme 1a). In contrast to the carbamate intermediate 13, the BNBD precursors are expected to be highly stable. Several BNBD-release molecules were successfully synthesized and demonstrated to undergo a rapid and traceless cargo-release reaction with Tz. Payload liberation was near-quantitative, and isoindole intermediates decomposed so rapidly that they were undetectable. Cytotoxicity assays demonstrated the efficient restoration of doxorubicin from a BNBD-prodrug, whereas the prodrug itself showed little toxicity. Importantly, BNBD molecules were highly stable and no unspecific payload release was observed after a week of incubation in human serum.

Figure 15:
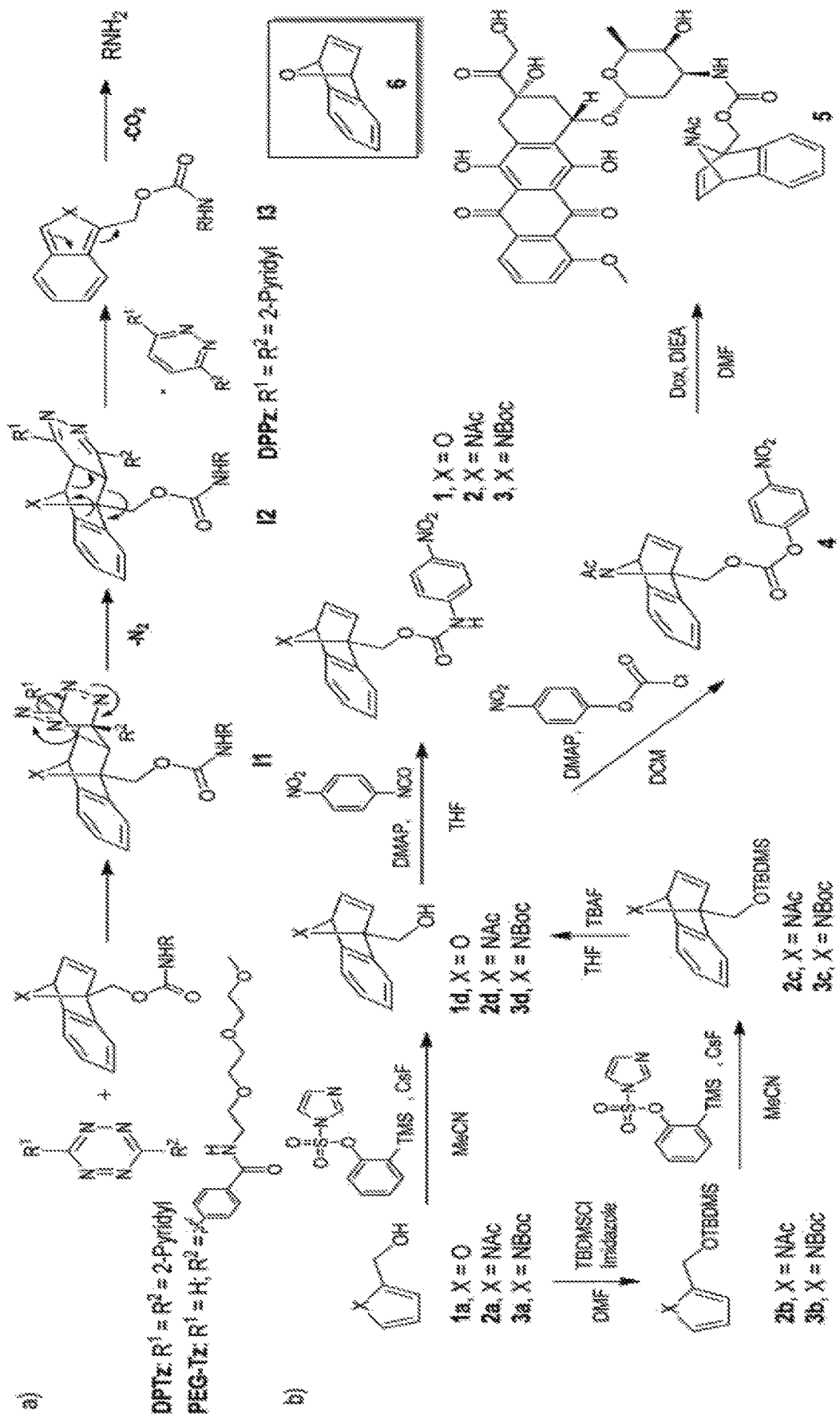
FIG. 15 illustrates a reaction scheme for various bioorthogonal compounds, in accordance with examples of the present disclosure.

With this overview in mind, benzonorbornadiene (BNBD) derivatives were designed to release a drug or reporter molecule upon reaction with tetrazine (Tz), as illustrated in FIG. 15 (Scheme 1).

In further detail, to test the proposed molecular design, three BNBD derivatives were synthesized with oxygen (1), acetamide (2), and Boc-protected nitrogen (3) at position 7 of the BNBD bicycle and a (p-nitrophenylcarbamoyl)methyl substituent at the bridgehead carbon (Scheme 1b). The different substituents in 1-3 were selected to test the influence of the heterocycle on reaction rate and cargo release. p-Nitroaniline (pNA) was selected as the reporter for bond-cleavage because a bathochromic shift of the absorbance maximum from X=317 nm to $\lambda_{max}$=378 nm accompanies conversion from a carbamate to an amine. The synthesis of 1-3 (Scheme 1b) started from furfuryl alcohol (1a) and N-acetyl- or N-Boc-(2-hydroxymethyl)pyrroles (2a,3a). A [4+2] cycloaddition reaction of these heterocylces with benzyne afforded the bicyclic structures 1d-3d. The pyrroles required TBDMS-protection of the hydroxymethyl group (2b,3b) for the benzyne reaction.

Reaction of hydroxymethyl bicycles 1d-3d with (4-nitrophenyl)isocyanate provided the desired release structures 1-3.

Figure 16A:
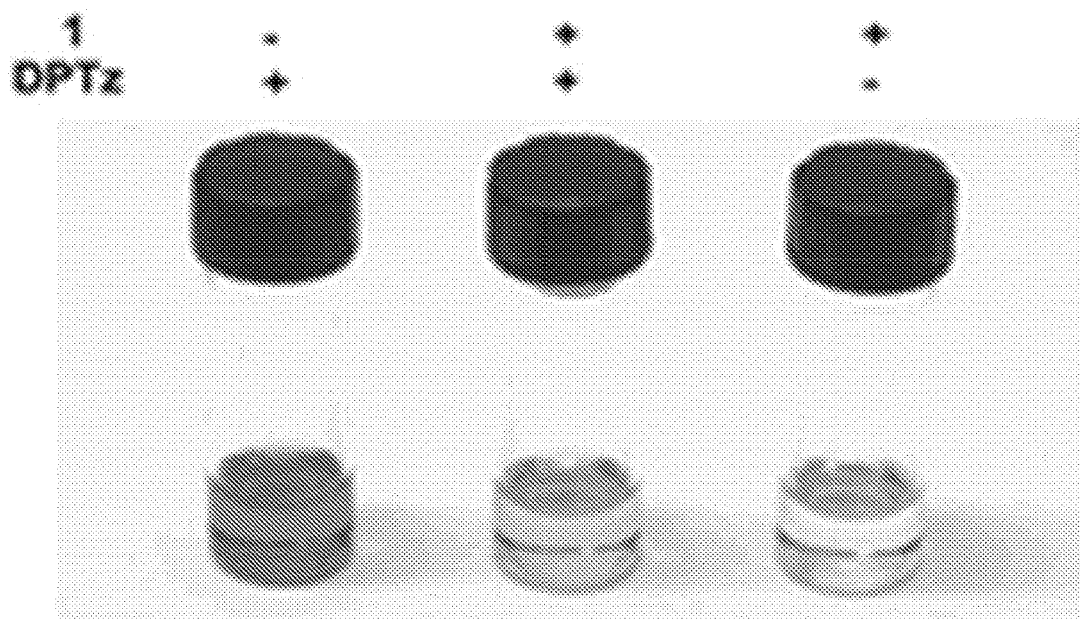
FIG. 16A illustrates a color change resulting from the reaction of 1 and DPTz (c(1)=c(DPTz)=6 mM, 24 h, RT).
Figure 16B:
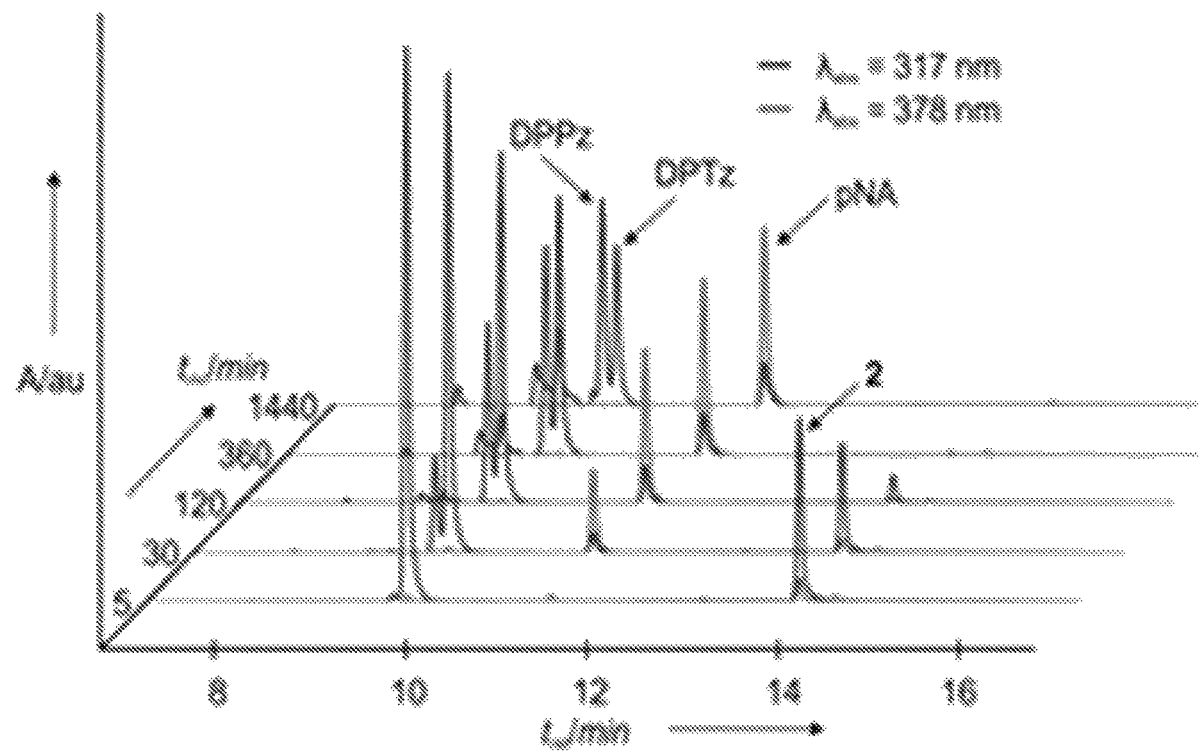
FIG. 16B illustrates an HPLC analysis of a reaction of 2 with DPTz (c(2)=6 mM; c(DPTz)=18 mM; T=37° C.).
Figure 16C:
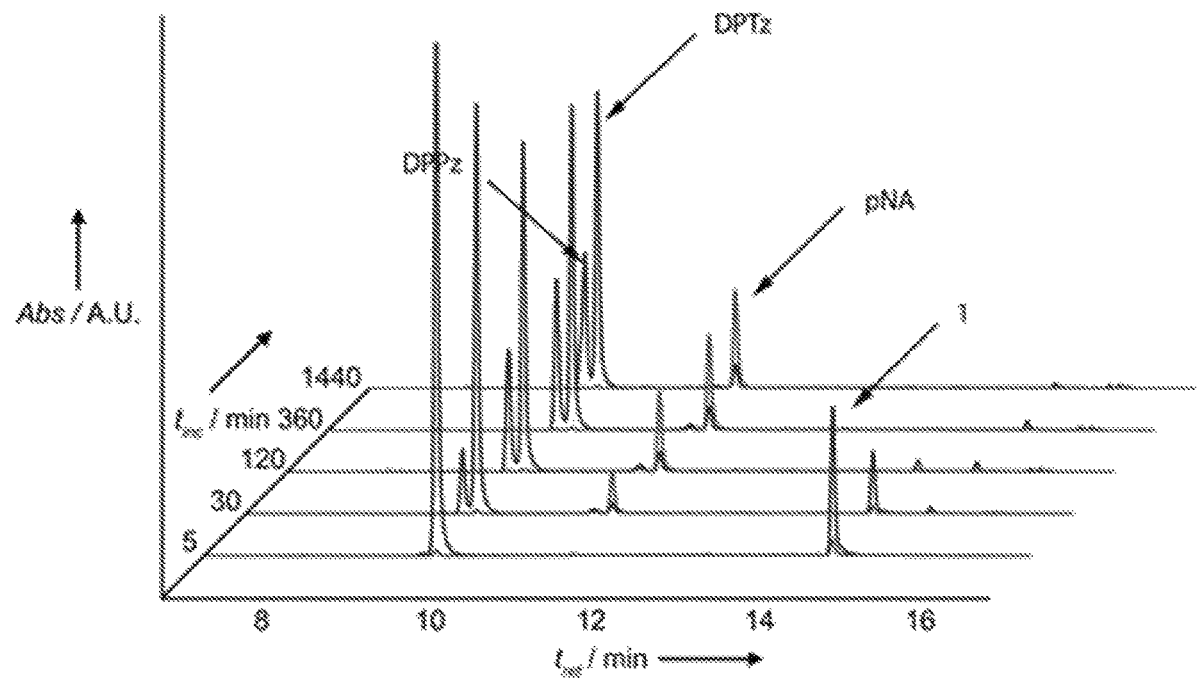
FIG. 16C illustrates an analysis of reaction between 1 and DPTz at different time points. From left to right: DPPz, DPTz, pNA and 1 (Indicated with arrows). The mobile phase A was 0.1% TFA in water and mobile phase B was acetonitrile. A gradient of 0-100% B ranging from 1-15 min and 100% B ranging from 15-18 min was run at a flow rate of 4.0 mL/min. Retention time for DPPz: 9.87-9.96 min; DPTz: 9.98-10.05 min; pNA: 11.71-11.81 min; 1: 14.78-14.80 min.
Figure 16D:
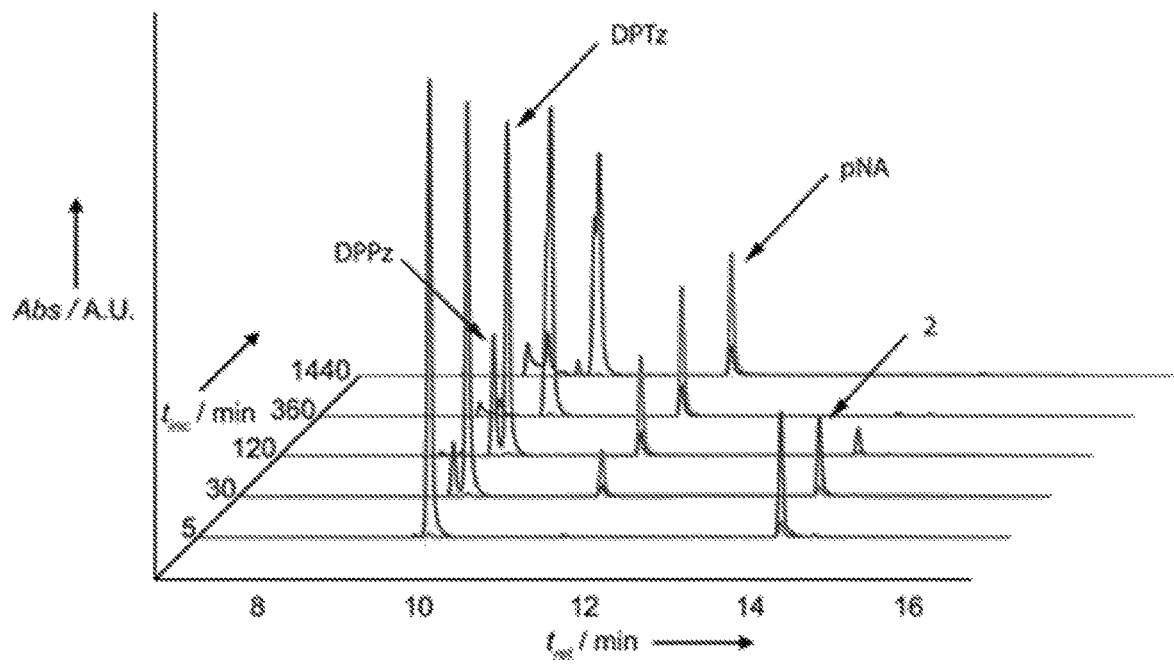
FIG. 16D illustrates an analysis of reaction of 2 and DPTz at different time points. From left to right: DPPz, DPTz, pNA and 2 (Indicated with arrows). The mobile phase A was 0.1% TFA in water and mobile phase B was acetonitrile. A gradient of 0-100% B ranging from 1-15 min and 100% B ranging from 15-18 min was run at a flow rate of 4.0 mL/min. Retention time for DPPz: 9.85-10.08 min; DPTz: 10.06-10.14 min; pNA: 11.68-11.76 min; 2: 14.32-14.37 min.
Figure 16E:
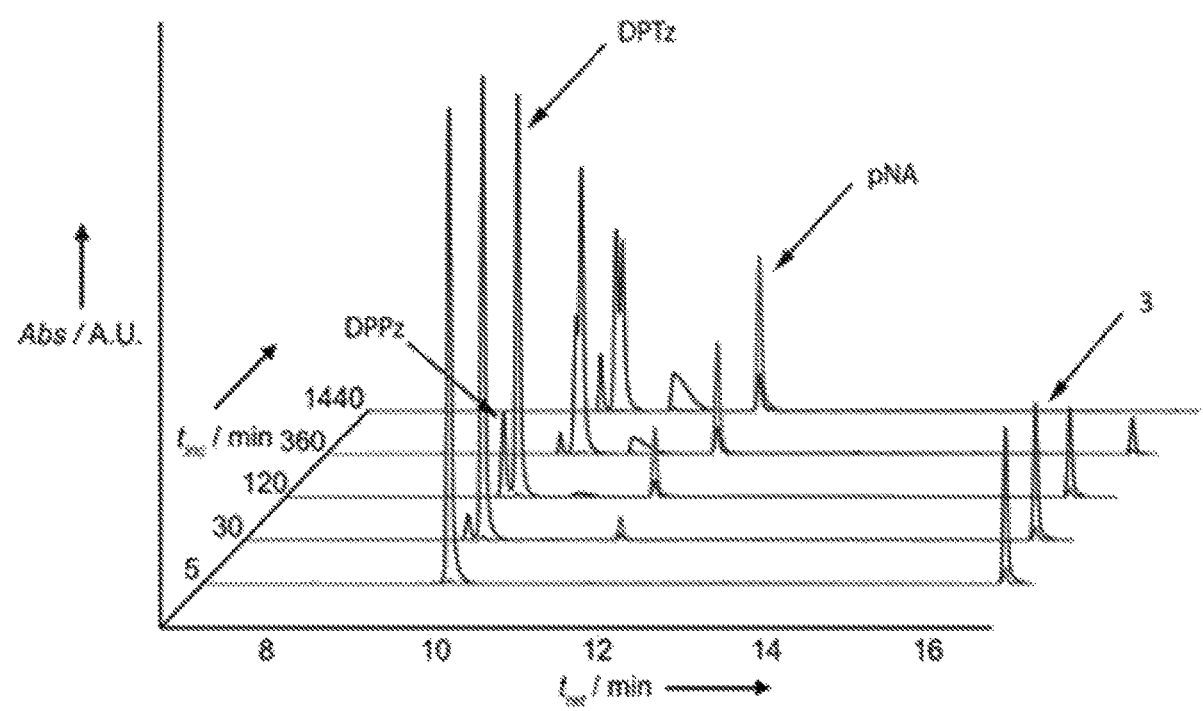
FIG. 16E illustrates a release analysis of 3 with DPTz at different time points. From left to right: DPPz, DPTz, pNA and 3 (Indicated with arrows). The mobile phase A was 0.1% TFA in water and mobile phase B was acetonitrile. A gradient of 0-100% B ranging from 1-15 min and 100% B ranging from 15-18 min was run at a flow rate of 4.0 mL/min. Retention time for DPPz: 9.83-10.18 min; DPTz: 10.00-10.23 min; pNA: 11.64-11.87 min; 3: 16.64-16.89 min.

It was first investigated whether the reaction of BNBD-derivatives with Tz released pNA (FIGS. 16A-16B). Specifically, stock solutions of 1 (12 mM) and DPTz (12 mM) in DMSO were prepared. Aliquots of the DPTz stock solution (500 µL) was added with DMSO (500 µL); Solution of 1 (500 µL) was added with DPTz stock solution (500 µL); Solution of 1 (500 µL) was added with DMSO (500 µL). The samples were incubated at 37° C. and the image was recorded at the time point of 24 h, shown as FIG. 16A.

Incubation of 1-3 with 3,6-di-(2-pyridyl)-1,2,4,5-tetrazine (DPTz) resulted in a distinct color change from pink to yellow (vials from left to right in FIG. 16A), which indicated complete DPTz consumption and efficient pNA release. Control samples with 1-3 or DPTz alone exhibited no color change over >24 h, and $^1$H NMR and HPLC analysis confirmed the stability of all individual reagents (data not shown). HPLC monitoring of the reaction (c(1-3)=6 mM, c(DPTz)=18 mM, T=37° C., DMSO/$H_2O$ (9:1)) confirmed complete consumption of 1-3, disappearance of DPTz, and formation of two new elution peaks that were assigned as pNA and 3,6-di-(2-pyridyl)-1,2-pyridazine (DPPz) based on retention time, extinction maxima of absorbance spectra, and molecular mass (FIGS. 16B-16E). Importantly, the starting BNBD was the only detectable peak with an absorbance maximum at $\lambda_{max}$=317 nm (FIG. 16B) and intermediates 11-13 or side-products with trapped pNA were not observed. Products of isoindole/isobenzofuran decomposition were visible in the HPLC traces at later measurement times (FIG. 16B). This outcome demonstrated that the release of the amine from the isoindole intermediate 13 is rapid and high-yielding.

Having established the Tz-induced release of pNA, the kinetics of the reaction of 1-3 and Tz were measured (See FIGS. 22A-22K). Photospectrometric analysis of DPTz disappearance ($\lambda_{abs}$=525 nm) in the presence of excess BNBDs revealed pseudo-first order kinetics, and the concentration dependence of the rate constants agreed with a second-order rate law. In DMSO, the second order rate constants ($k_2$) were 0.015 $M^{-1}$ $s^{-1}$ for 1, 0.010 $M^{-1}$ $s^{-1}$ for 2, and 0.0044 $M^{-1}$ $s^{-1}$ for 3 (Table 1). The differences in the rate constants reflect the increase in steric repulsion from 1 to 3 although electronic effects may also influence the reaction rate. Comparison of the kinetics of the reaction of DPTZ with 1 to that with 7-oxo-BNBD (6, Scheme 1b; $k_2$=0.176 $M^{-1}$ $s^{-1}$) revealed that the (p-nitrophenylcarbamoyl)methyl substituent decreased the reaction rate ~12-fold. Presence of 10% water accelerated the reaction 1.7 to 1.9-fold (Table 1; 1: $k_2$=0.028 $M^{-1}$ $s^{-1}$; 2: $k_2$=0.017 $M^{-1}$ $s^{-1}$; 3: $k_2$=0.0084 $M^{-1}$ $s^{-1}$). This result is in agreement with reported rate-enhancing effects of water on IEDDA reactions. A water-soluble Tz (PEG-Tz; Scheme 1a) was also prepared and tested to evaluate the solvent effect on the reaction kinetics (Table 1). Increasing the water content further (DMSO/PBS, 3:2) substantially accelerated the reaction rate of 2 ($k_2$=0.135 $M^{-1}$ $s^{-1}$) and 1 ($k_2$=0.190 $M^{-1}$ $s^{-1}$) with PEG-Tz. These reaction rates were comparable to those of TCO-based release molecules with 4,6-dimethyltetrazine ($k_2$=0.54 $M^{-1}$ $s^{-1}$). More electron-deficient Tz molecules reacted faster with TCO-prodrugs but at the expense of incomplete drug release. The reaction of 1 and 2 with Tz was significantly faster than the release reaction of TCO with aromatic azides ($k_2$=0.027 $M^{-1}$ $s^{-1}$), Tz-induced uncaging of vinyl ethers ($k_2$=0.00021 $M^{-1}$ $s^{-1}$), and the Staudinger reaction with release functionality ($k_2$=~0.001 $M^{-1}$ $s^{-1}$). In conclusion, the reaction of BNBD with Tz proceeds at a comparable or higher rate than previous bioorthogonal release reactions.

TABLE 1

Second-order rate constants ($k_2$) for reactions of 1-3 and tetrazines ($M^{-1}s^{-1}$)$^a$

| Pb | Tz | DMSO | 90% DMSO/$H_2O$ | 60% DMSO/PBS |
|----|------|------------------|------------------|--------------|
| 1  | DPTz | 0.015 ± 0.008    | 0.028 ± 0.0003   | n/a          |
| 2  | DPTz | 0.010 ± 0.0004   | 0.017 ± 0.002    | n/a          |

TABLE 1-continued

Second-order rate constants ($k_2$) for reactions of 1-3 and tetrazines ($M^{-1}s^{-1}$)[a]

| Pb | Tz | DMSO | 90% DMSO/H$_2$O | 60% DMSO/PBS |
|---|---|---|---|---|
| 3 | DPTz | 0.0044 ± 0.00009 | 0.0084 ± 0.0016 | n/a |
| 6 | DPTz | 0.176 ± 0.004 | n/a | n/a |
| 1 | PEG-Tz | n/a | 0.058 ± 0.0003 | 0.190 ± 0.029 |
| 2 | PEG-Tz | n/a | 0.020 ± 0.0007 | 0.135 ± 0.010 |

[a]The reactions were monitored by time-dependent absorbance measurements at $\lambda_{abs}$ = 525 nm and T = 37° C.

Figure 17A:
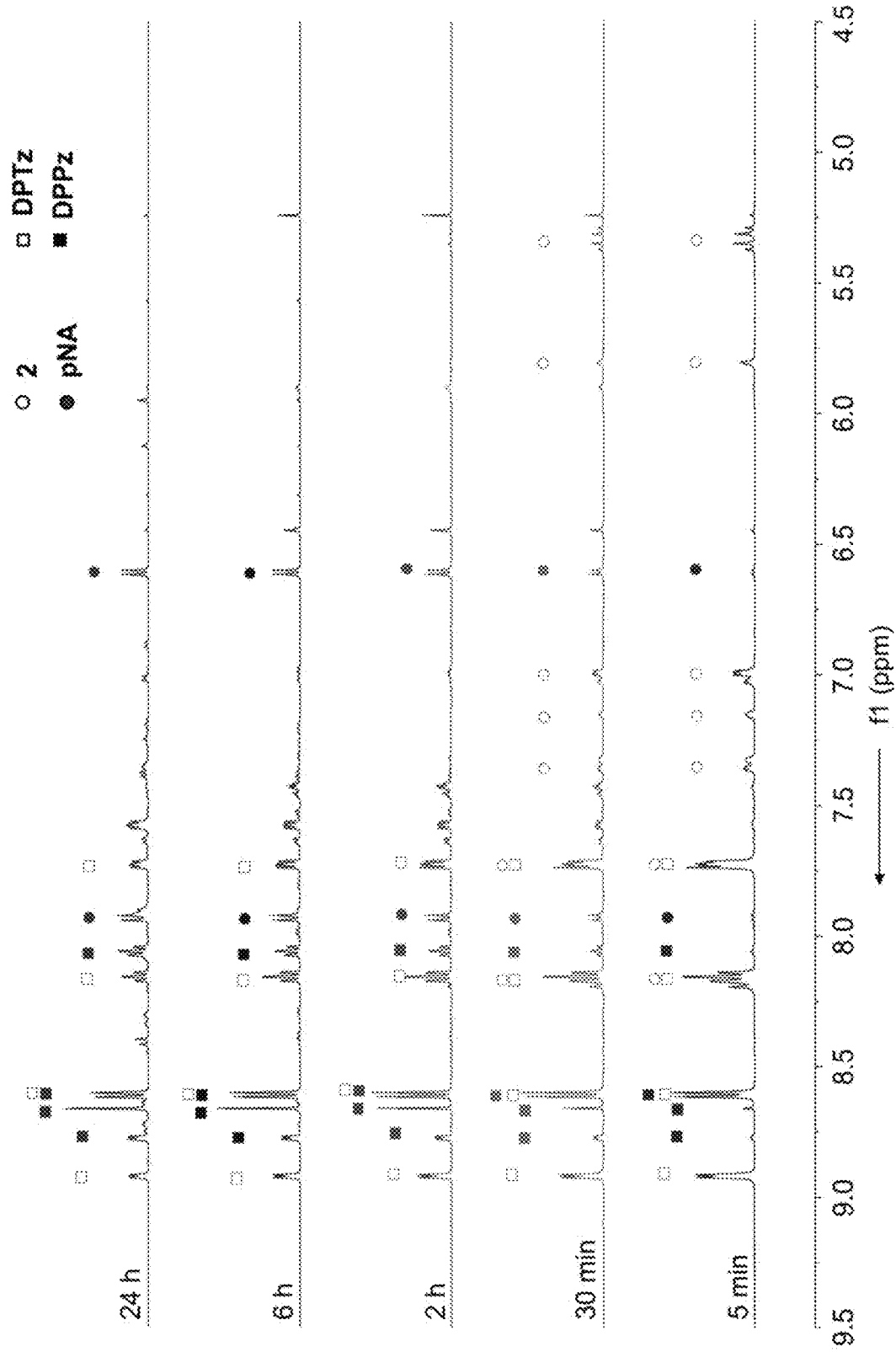
FIG. 17A illustrates an $^1$H NMR analysis of the time-dependent pNA release from 2.
Figure 17B:
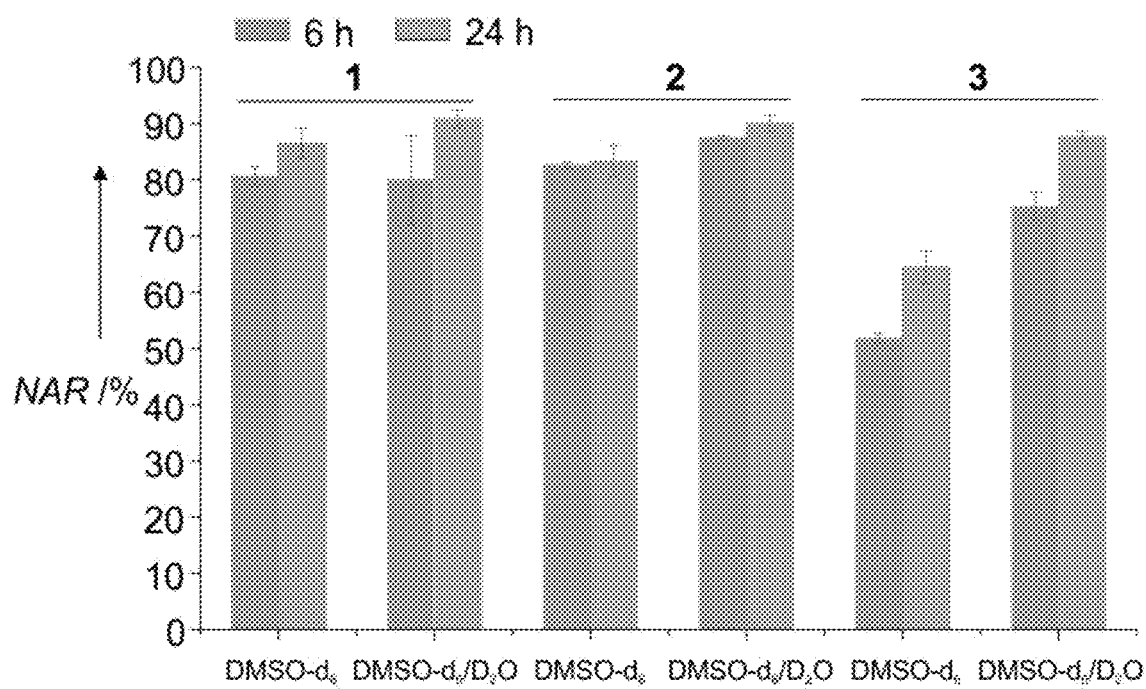
FIG. 17B depicts a quantification of the release of p-nitroaniline (pNA) from 7-aza/oxa-BNBD 1-3.

To quantify pNA release and to analyze the mechanism of the reaction of 1-3 and DPTz, the transformation was monitored in a series of $^1$H NMR experiments (FIGS. 17A-17G). Solutions of 1-3 and DPTz in DMSO-d$_6$ or DMSO-d$_6$/D$_2$O (9:1) were incubated at 37° C. and $^1$H NMR spectra were recorded periodically over 24 h. At these conditions, DPTz near-completely consumed BNBD derivatives within 2 h in agreement with results from HPLC analysis (FIG. 16B) and kinetics measurements (Table 1). NMR peaks corresponding to pNA emerged concomitant with disappearance of 1-3, indicating rapid and efficient cargo liberation (FIGS. 17A-17G). The measured pNA release from 1 and 2 in DMSO-d$_6$/D$_2$O at 6 h and 24 h was in the range of 80-90%. Release of pNA from 3 was less efficient especially in water-free DMSO-d$_6$ (FIG. 17B).

Figure 17C:
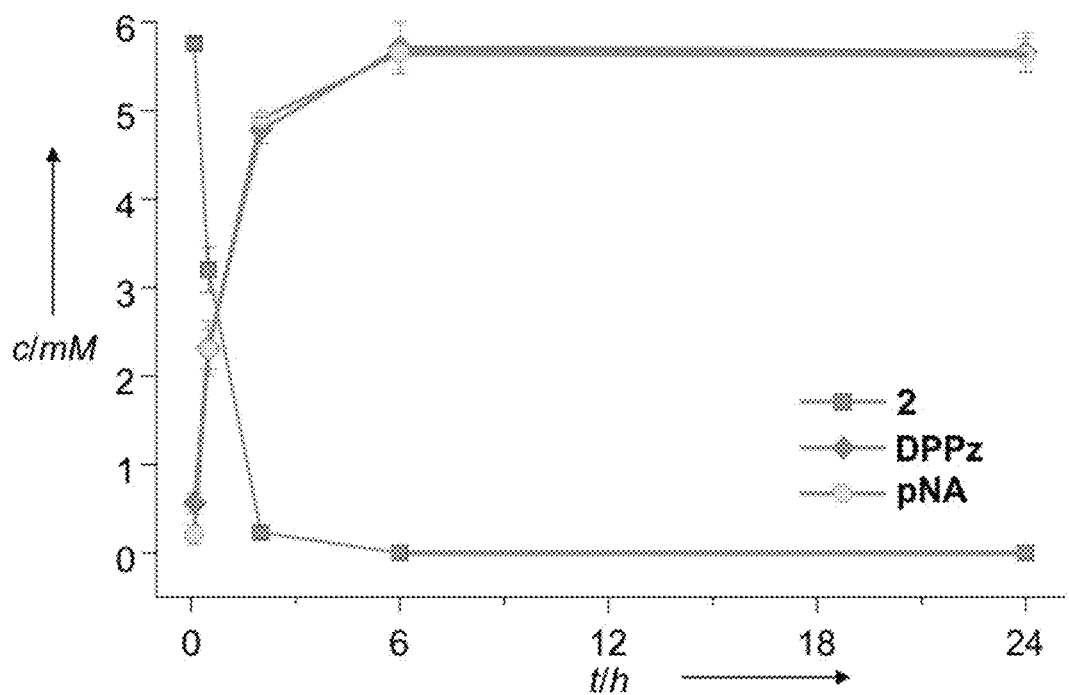
FIG. 17C depicts concentrations of starting material (2) and reaction products (DPPz, pNA) as a function of time.
Figure 17D:
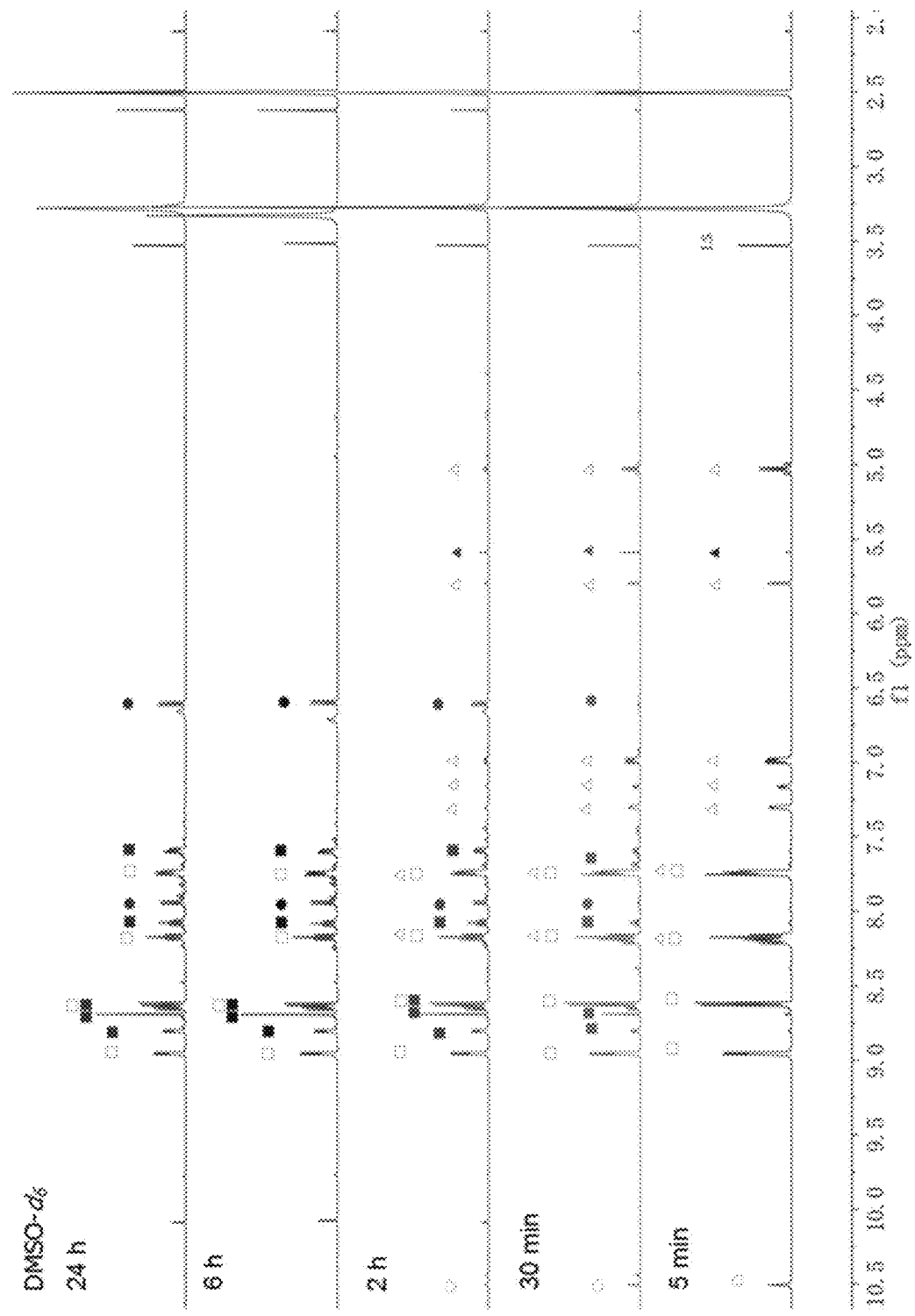
FIG. 17D illustrates full spectrum monitoring the bioorthogonal release reaction of 1 with DPTz in DMSO-$d_6$. Legend: 1:△; DPTz:□; pNA:●; DPPz:■; I3:▲. I.S: Internal standard.
Figure 17E:
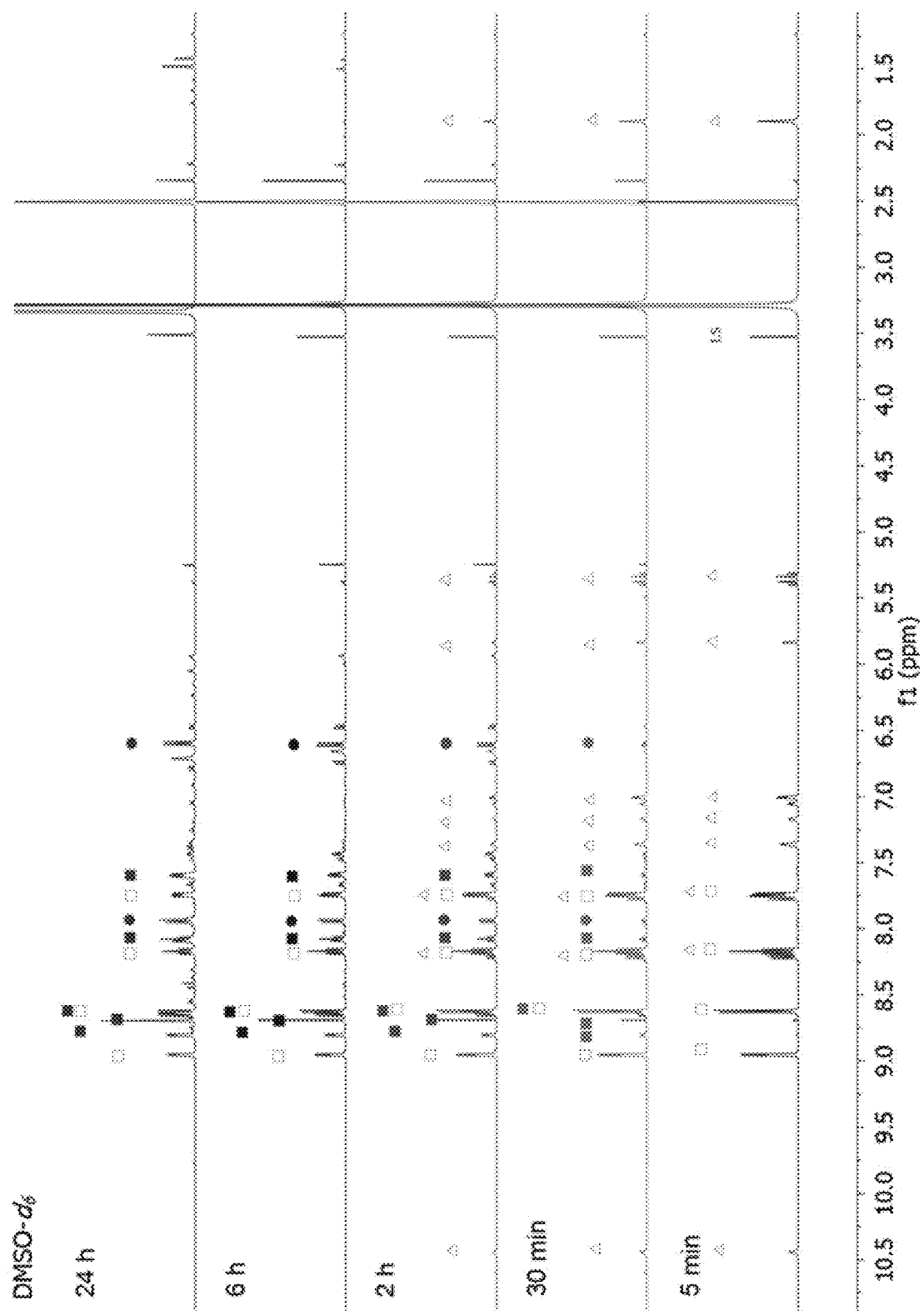
FIG. 17E illustrates full spectrum monitoring the bioorthogonal release reaction of 2 with DPTz in DMSO-$d_6$. Legend: 2:△; DPTz:□; pNA:●; DPPz:■. I.S: Internal standard.
Figure 17F:
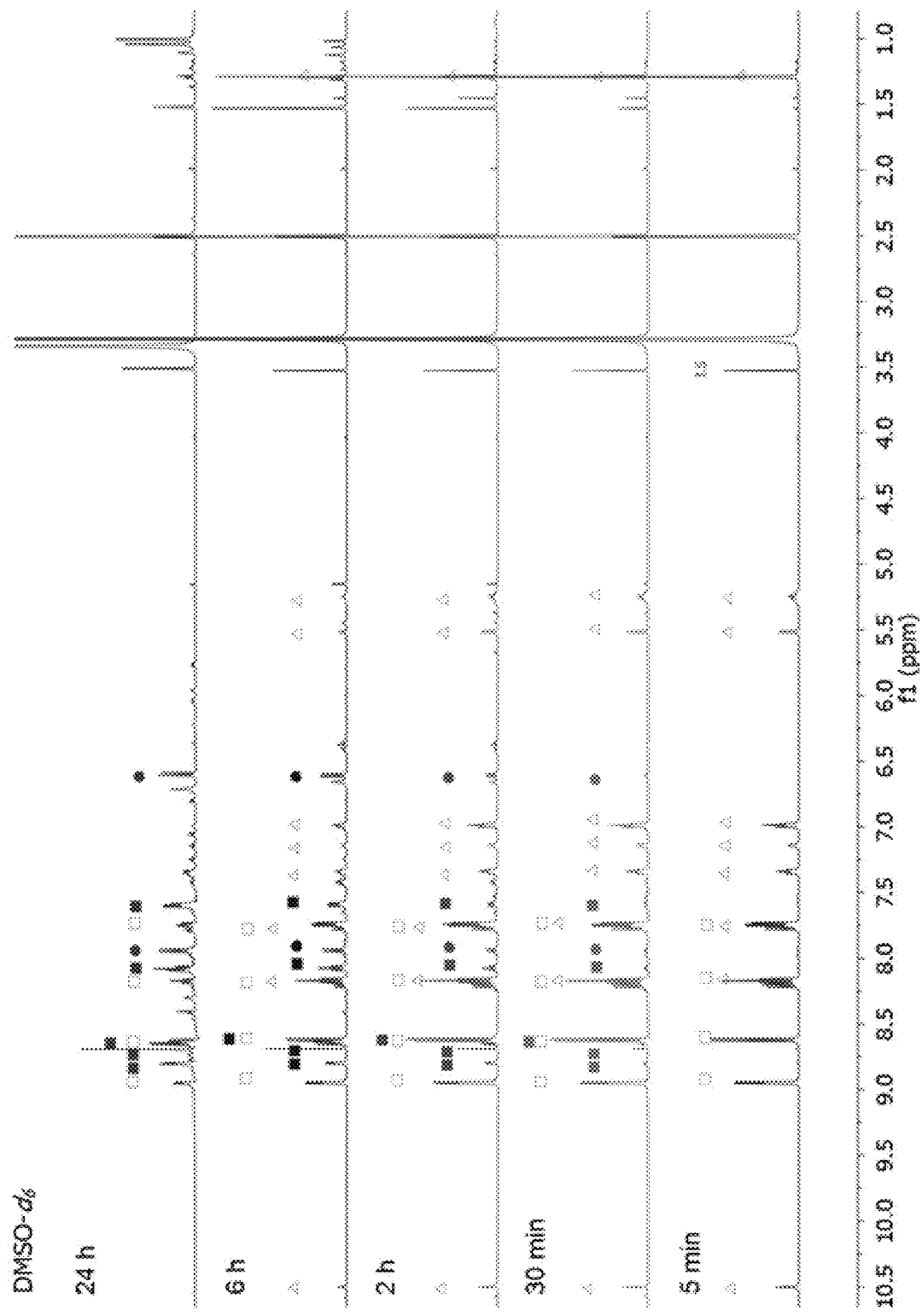
FIG. 17F illustrates full spectrum monitoring the bioorthogonal release reaction of 3 with DPTz in DMSO-$d_6$. Legend: 3:△; DPTz:□; pNA:●; DPPz:■. I.S: Internal standard.
Figure 17G:
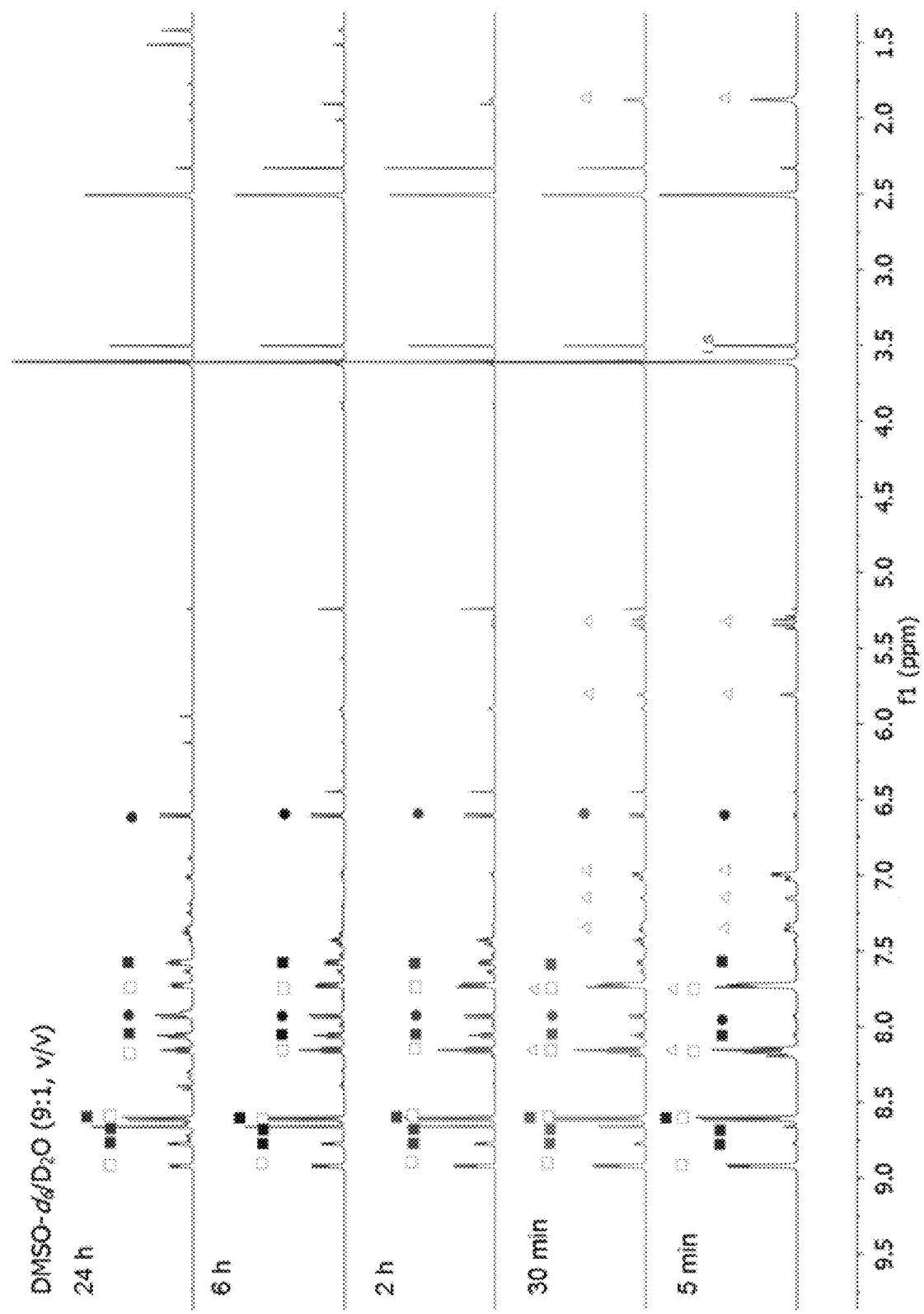
FIG. 17G illustrates full spectrum monitoring the bioorthogonal release reaction of 2 with DPTz in DMSO-$d_6$/$D_2O$ (9:1, v/v). Legend: 2:△; DPTz:□; pNA:●; DPPz:■. I.S: Internal standard.

Analysis of $^1$H NMR integrations revealed that in the case of 1 the formation of pNA was delayed relative to BNBD consumption (FIG. 17D). A singlet peak at 5.59 ppm was present in early $^1$H NMR spectra but disappeared with longer incubation times.

Figure 24:
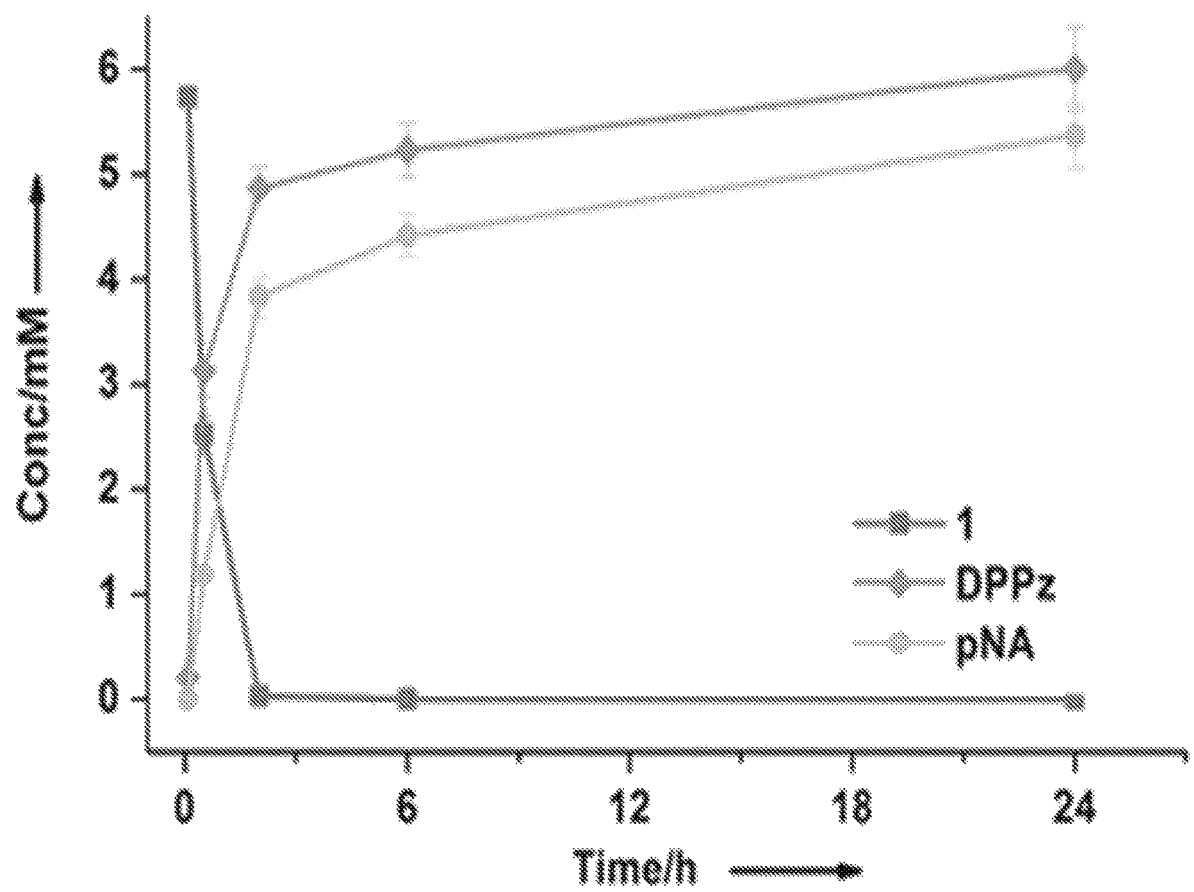
FIG. 24 illustrates product distributions as a function of time for the reaction of 1 and DPTz in DMSO-$d_6$/$D_2O$ (9:1, v/v) at 37° C. Conditions were the same as for $^1H$ NMR mechanism studies. The results are expressed as the mean±standard deviation (n=3).

Integration of this peak accounted for the difference between consumed 1 and released pNA, and it is postulated that it may correspond to the heterocyclic intermediate 13 (Scheme 1a) (See FIG. 24). In contrast, consumption of 2 and DPPz formation occurred in parallel with pNA generation (FIG. 17C). $^1$H NMR peaks consistent with the structure of I3 were absent (FIG. 17A). These results demonstrate that isoindole intermediates 13 release amines rapidly and near-quantitatively.

Figure 18:
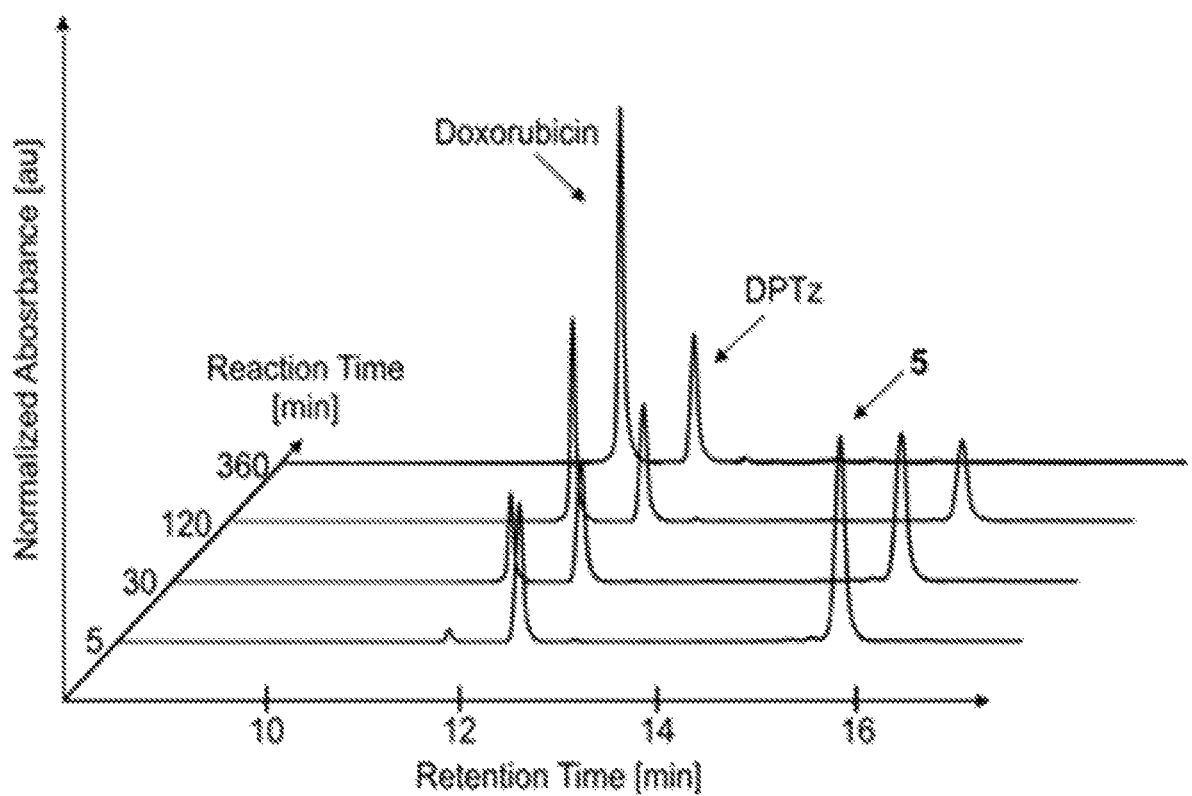
FIG. 18 illustrates an HPLC analysis of the reaction of 5 with PEG-Tz in DMSO/PBS solution (1:1, v.v) at different time points. From left to right: Released Dox, PEG-Tz and Prodrug 5 (Indicated with arrows). The mobile phase A was 0.1% TFA in water and mobile phase B was acetonitrile. A gradient of 0-75% B ranging from 1-15 min and 75%-100% B from 15-18 min and 100% B ranging from 15-18 min was run at a flow rate of 4.0 mL/min. Retention time for Free Dox: 11.80-11.87 min; PEG-Tz: 12.50-12.60; 5: 15.68-15.74 min.

Given the demonstrated Tz-induced liberation of a reporter molecule (pNA), the potential of BNBDs in a prodrug activation strategy was evaluated. A 7-acetamide-BNBD doxorubicin prodrug (5) was synthesized from 2d (Scheme 1b). HPLC analysis of the reaction between 5 and PEG-Tz (DMSO, T=37° C., c(5)=0.2 mM, c(PEG-Tz)=1.6 mM) showed rapid and complete doxorubicin release (FIG. 18).

Figure 19A:
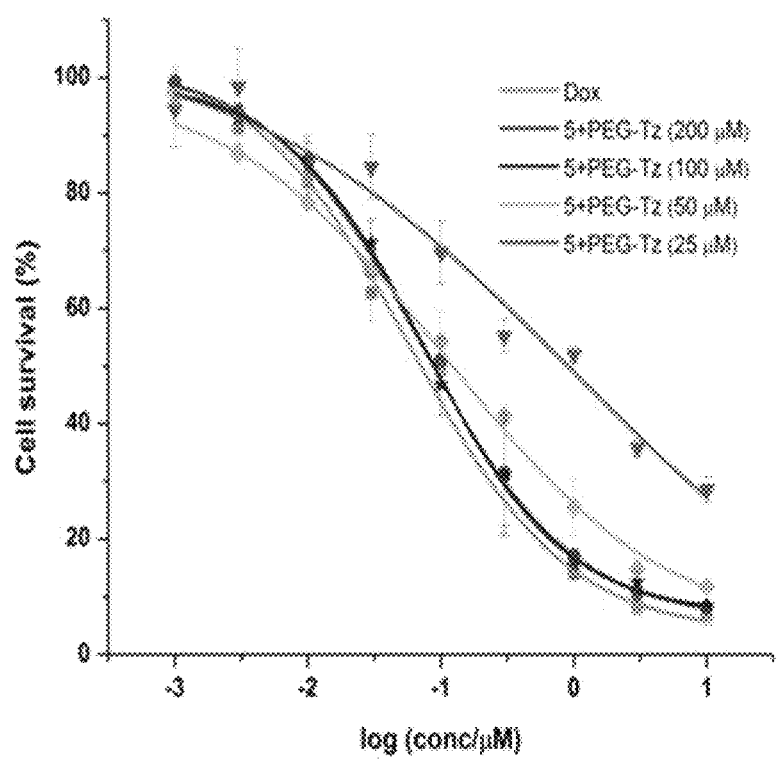
FIG. 19A illustrates a cytotoxicity assay against lung cancer A549 cells. The results are expressed as the mean±standard deviation (n=3).
Figure 19B:
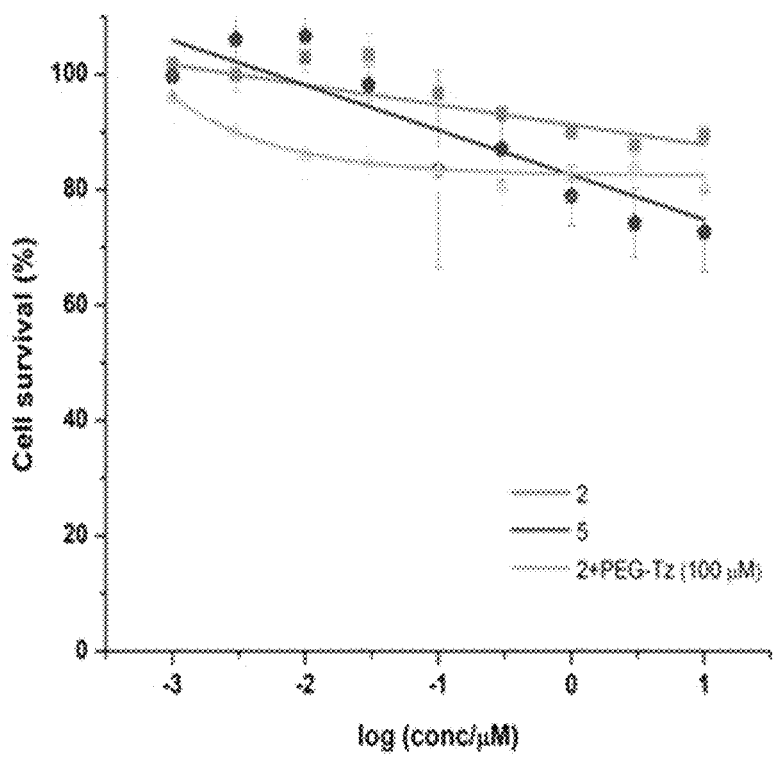
FIG. 19B illustrates a cytotoxicity assay against lung cancer A549 cells. The results are expressed as the mean±standard deviation (n=3).
Figure 20A:
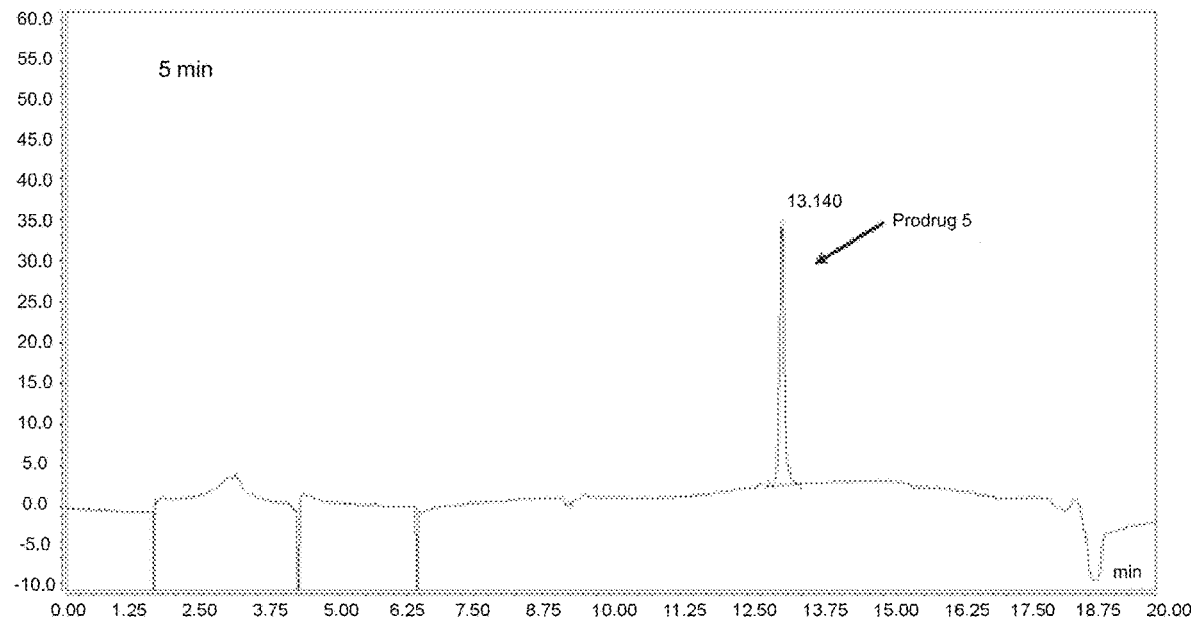
FIG. 20A illustrates a representative spectrum of an HPLC analysis of the stability of 5 in human serum at 5 minutes. Prodrug 5 is indicated with arrow. The mobile phase A was 0.1% TFA in water and mobile phase B was acetonitrile. A gradient of 0-100% B ranging from 1-15 min and 100% B ranging from 15-18 min was run at a flow rate of 4.0 mL/min. Retention time for 5: 13.18-13.33 min.
Figure 20B:
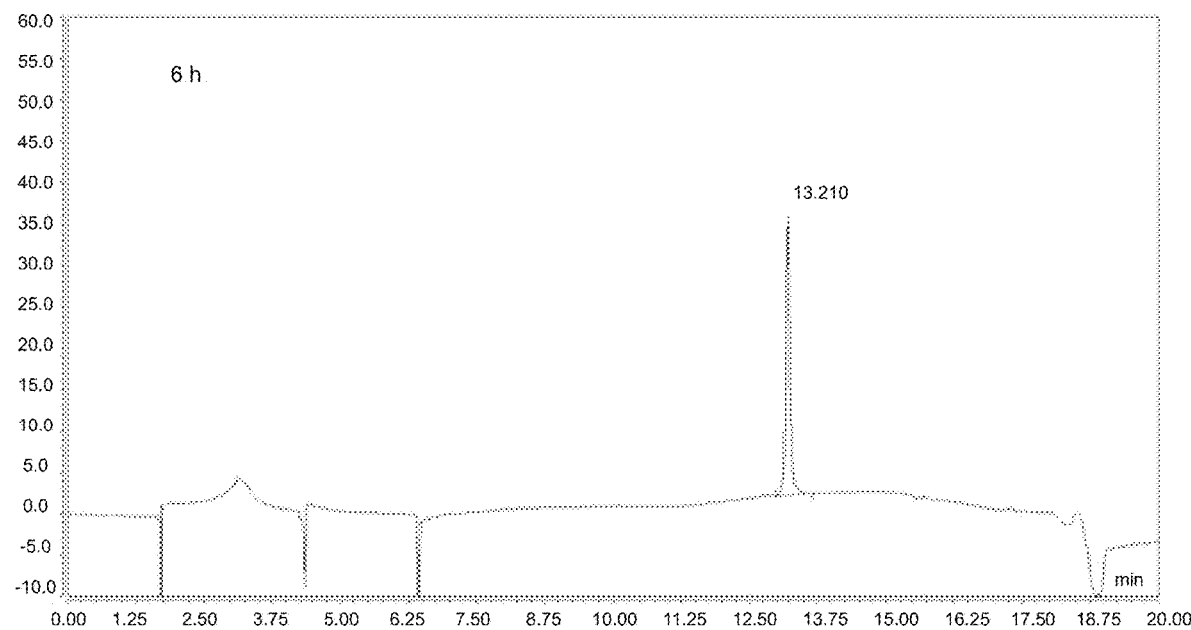
FIG. 20B illustrates a representative spectrum of an HPLC analysis of the stability of 5 in human serum at 6 hours. The mobile phase A was 0.1% TFA in water and mobile phase B was acetonitrile. A gradient of 0-100% B ranging from 1-15 min and 100% B ranging from 15-18 min was run at a flow rate of 4.0 mL/min. Retention time for 5: 13.18-13.33 min.
Figure 20C:
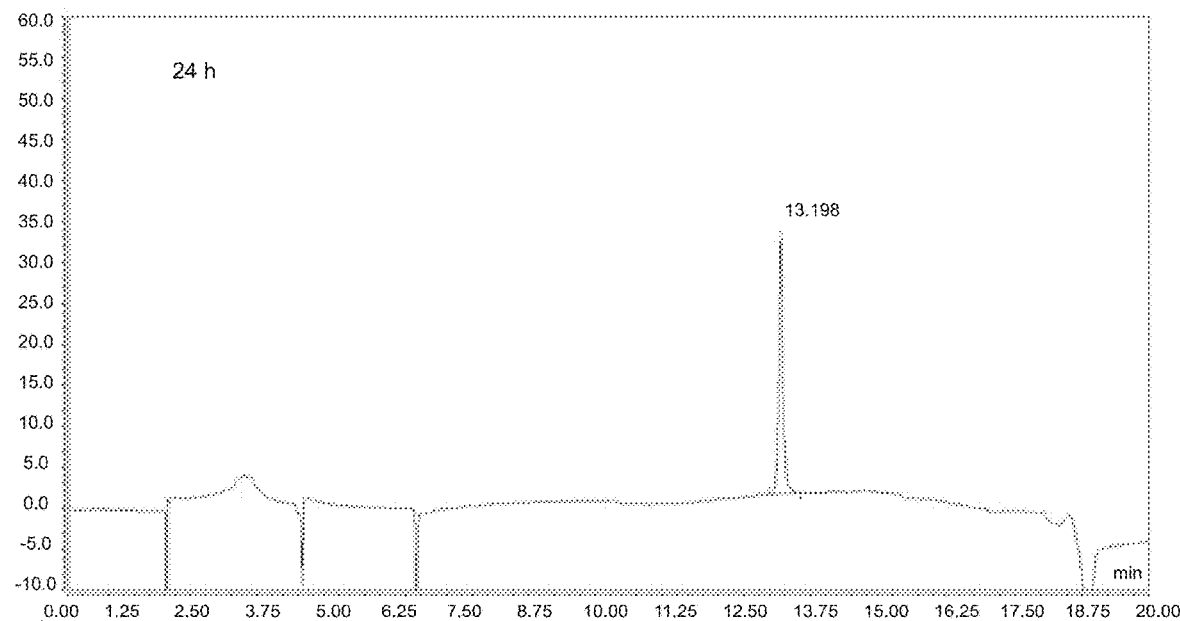
FIG. 20C illustrates a representative spectrum of an HPLC analysis of the stability of 5 in human serum at 24 hours. The mobile phase A was 0.1% TFA in water and mobile phase B was acetonitrile. A gradient of 0-100% B ranging from 1-15 min and 100% B ranging from 15-18 min was run at a flow rate of 4.0 mL/min. Retention time for 5: 13.18-13.33 min.
Figure 20D:
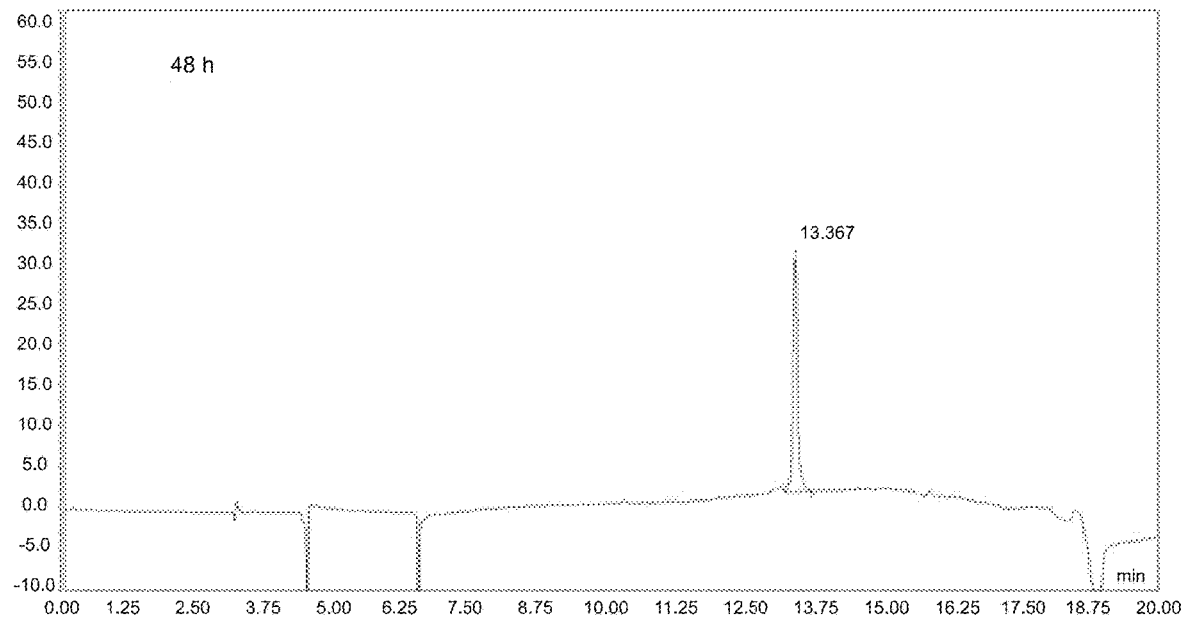
FIG. 20D illustrates a representative spectrum of an HPLC analysis of the stability of 5 in human serum at 48 hours. The mobile phase A was 0.1% TFA in water and mobile phase B was acetonitrile. A gradient of 0-100% B ranging from 1-15 min and 100% B ranging from 15-18 min was run at a flow rate of 4.0 mL/min. Retention time for 5: 13.18-13.33 min.

Tz-triggered drug release was further tested in cell viability assays. Combinations of doxorubicin-prodrug 5 and PEG-Tz caused dose-dependent cytotoxicity in A549 pulmonary adenocarcinoma cells ($EC_{50}$(5+200 μM PEG-Tz)= 96 nM), rivaling that of parent doxorubicin ($EC_{50}$(Dox)=88 nM, Table 2). Conversely, the prodrug 5 alone was essentially non-toxic in the tested concentration range ($EC_{50}$ (5)>10 μM; Table 2). This outcome demonstrated that reaction with PEG-Tz efficiently uncaged doxorubicin from 2 and restored its cytotoxicity whereas non-specific drug release at physiological conditions was minimal. The cytotoxic effect of 5 was preserved when decreasing the concentration of PEG-Tz to 50 μM ($EC_{50}$(5+50 μM PEG-Tz)= 128 nM). Even at the lowest tested concentration c(PEG-Tz)=25 μM, which is physiologically attainable, the combination with 5 was >20-fold more toxic than the prodrug alone (Table 2). Tetrazines are rather non-toxic, and in a previous mouse study, animals showed no adverse reactions to repeated intravenous injection of doses as high as 1250 μmol/kg. Indeed, control samples with PEG-Tz showed no cytotoxicity even at the highest concentration tested (200 M). Also, combination of PEG-Tz and 2 resulted in minimal toxicity in the tested concentration range (FIGS. 19A-19B) demonstrating that cells tolerate isoindole decomposition products well.

TABLE 2

Cytotoxicity of activated prodrug 5, 72 hour incubation at 37° C.[b]

| Compounds | $EC_{50}$ (μM) in A549 Cells |
|---|---|
| Doxorubicin | 0.088 ± 0.031 |
| 5 + PEG-Tz (200 μM) | 0.096 ± 0.022 |
| 5 + PEG-Tz (100 μM) | 0.099 ± 0.029 |
| 5 + PEG-Tz (50 μM) | 0.128 ± 0.017 |
| 5 + PEG-Tz (25 μM) | 0.521 ± 0.192 |
| 5 | >10 |
| 2 + PEG-Tz (100 μM) | >10 |
| PEG-Tz | >200 |

[b]The proliferation assay was performed in at least triplicate and $EC_{50}$ values were derived from the normalized cell growth.

Figure 23A:
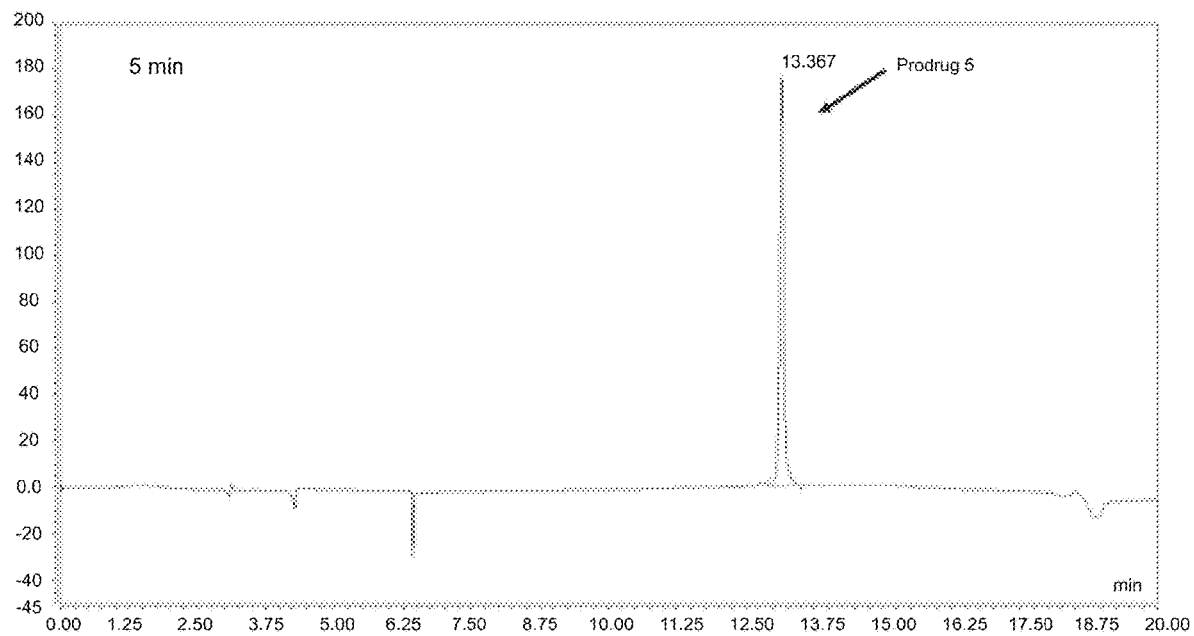
FIG. 23 depicts representative spectra of HPLC analysis of the stability of 5 in DMSO/PBS solution at different time points. Prodrug 5 is indicated with arrow. The mobile phase A was 0.1% TFA in water and mobile phase B was acetonitrile. A gradient of 0-100% B ranging from 1-15 min and 100% B ranging from 15-18 min was run at a flow rate of 4.0 mL/min. Retention time for 5: 13.16-13.20 min.
Figure 23B:
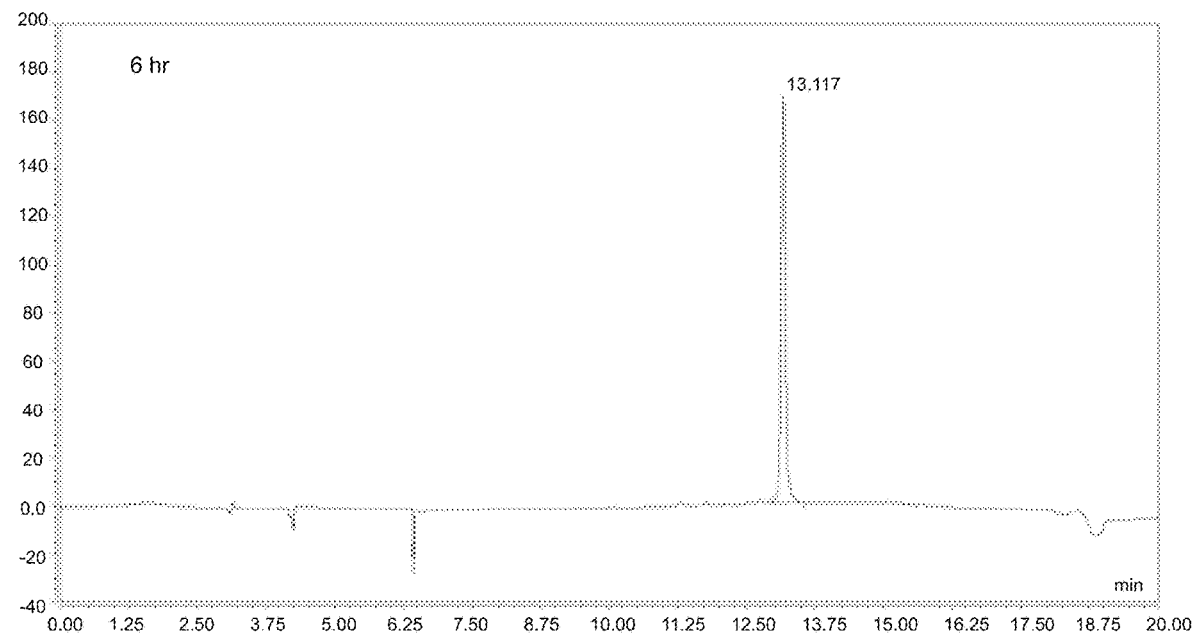
Figure 23C:
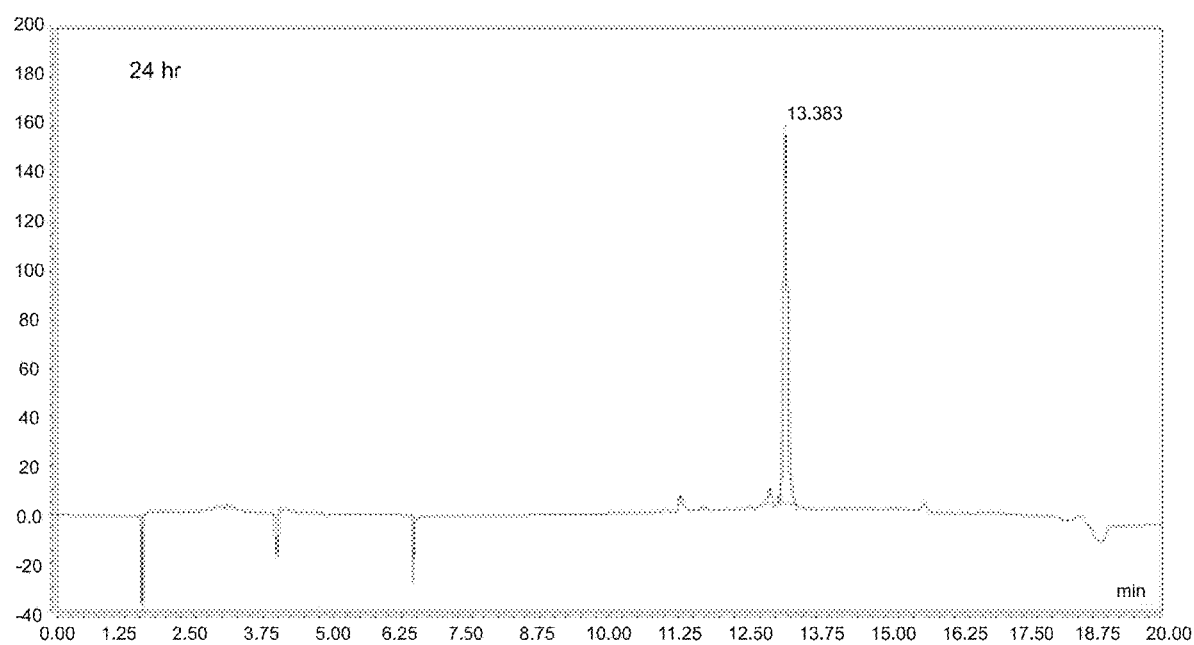

The stability of 5 in DMSO-PBS (1:1, v/v) was performed as illustrated in FIG. 23. Further, the stability of 5 in human serum was directly tested. 5 was inert for 48 h, and no free doxorubicin or doxorubicin-containing side products were observed by HPLC (FIGS. 20A-20D). The quantity of 5 decreased with longer incubation times but no free doxorubicin was detectable (FIGS. 20A-20D). In light of the known instability of the doxorubicin moiety in serum, it was reasoned that decomposition of doxorubicin rather than the BNBD linker was responsible for the observed effect. To test this hypothesis, the serum-stability of 2 was measured. It was determined that 2 was completely stable until the end of the analysis at one week and no traces of pNA were formed. These experiments demonstrated the potential of BNBDs as prospective chemically-triggered drug release molecules.

The present data demonstrates that BNBDs react rapidly with Tz and generate hydrolysis-susceptible heterocycles for the traceless release of a drug or reporter molecule. This novel probe design relies on unprecedented self-immolative isoindole/isobenzofuran intermediates for cargo liberation (See FIG. 15 for Scheme 1). The reaction exhibits favorable characteristics, including rapid bimolecular reaction, quantitative as well as near-instantaneous payload release, low reagent toxicity, and exceptional probe stability at physiological conditions.

Figure 21:
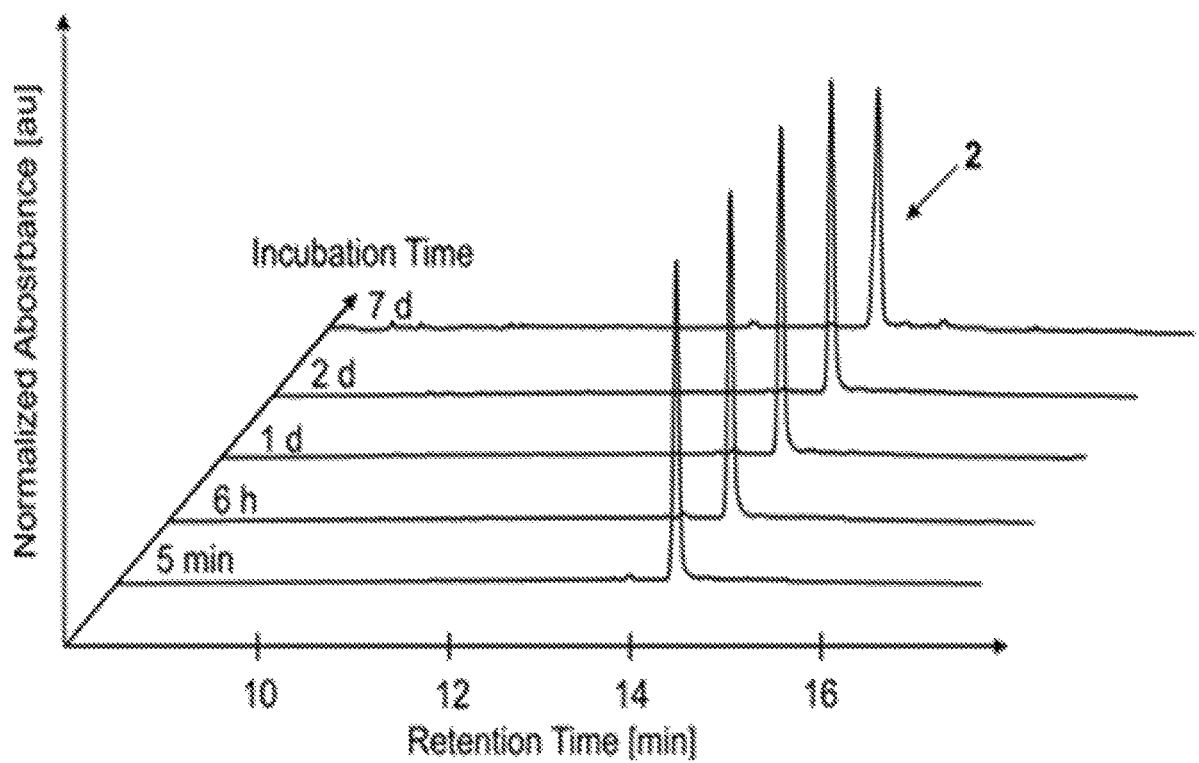
FIG. 21 depicts the stability of 2 in human serum as measured by HPLC at $\lambda_{Abs}$=317 nm.
Figure 22A:
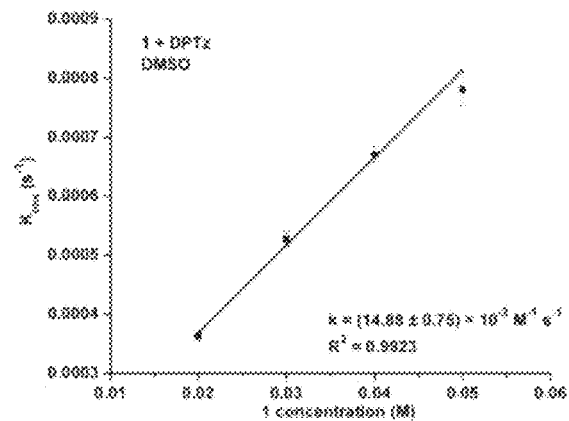
FIG. 22A depicts the second-order rate constant $k_2$ of the reaction with the benzonorbornadiene derivative 1 and the tetrazine DPTz in DMSO determined from a plot of pseudo-first order $k_{obs}$ versus concentration of 1. The results are expressed as the mean±standard deviation (n=3).
Figure 22B:
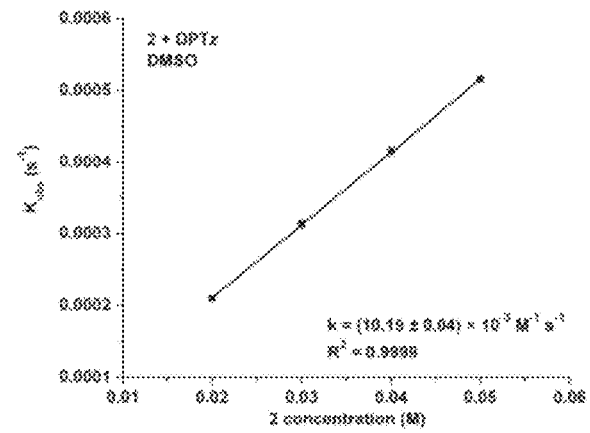
FIG. 22B depicts the second-order rate constant $k_2$ of the reaction with the benzonorbornadiene derivative 2 and the tetrazine DPTz in DMSO determined from a plot of pseudo-first order $k_{obs}$ versus concentration of 2. The results are expressed as the mean±standard deviation (n=3).
Figure 22C:
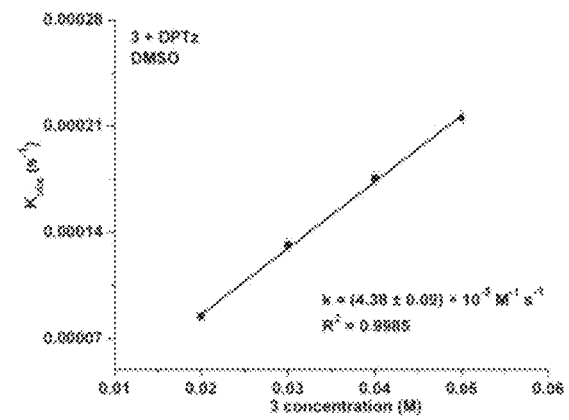
FIG. 22C depicts the second-order rate constant $k_2$ of the reaction with the benzonorbornadiene derivative 3 and the tetrazine DPTz in DMSO determined from a plot of pseudo-first order $k_{obs}$ versus concentration of 3. The results are expressed as the mean±standard deviation (n=3).
Figure 22D:
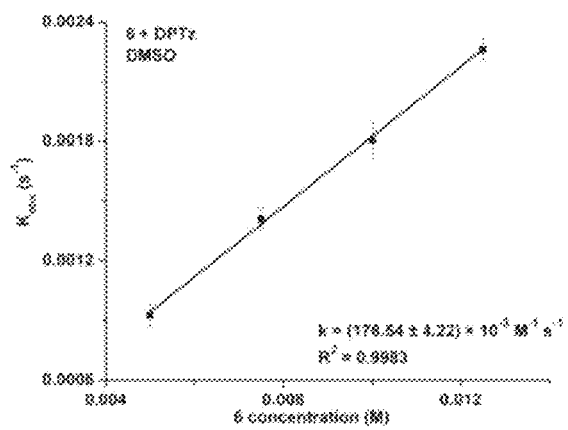
FIG. 22D depicts the second-order rate constant $k_2$ of the reaction with the benzonorbornadiene derivative 4 and the tetrazine DPTz in DMSO determined from a plot of pseudo-first order $k_{obs}$ versus concentration of 4. The results are expressed as the mean±standard deviation (n=3).
Figure 22E:
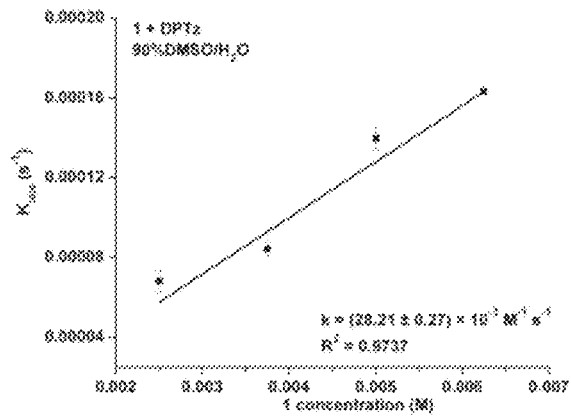
FIG. 22E depicts the second-order rate constant $k_2$ of the reaction with the benzonorbornadiene derivative 1 and the tetrazine DPTz in 90% DMSO/$H_2O$ determined from a plot of pseudo-first order $k_{obs}$ versus concentration of 1. The results are expressed as the mean±standard deviation (n=3).
Figure 22F:
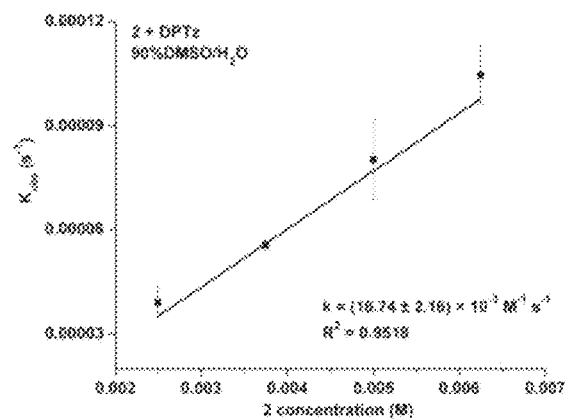
FIG. 22F depicts the second-order rate constant $k_2$ of the reaction with the benzonorbornadiene derivative 2 and the tetrazine DPTz in 90% DMSO/$H_2O$ determined from a plot of pseudo-first order $k_{obs}$ versus concentration of 2. The results are expressed as the mean±standard deviation (n=3).
Figure 22G:
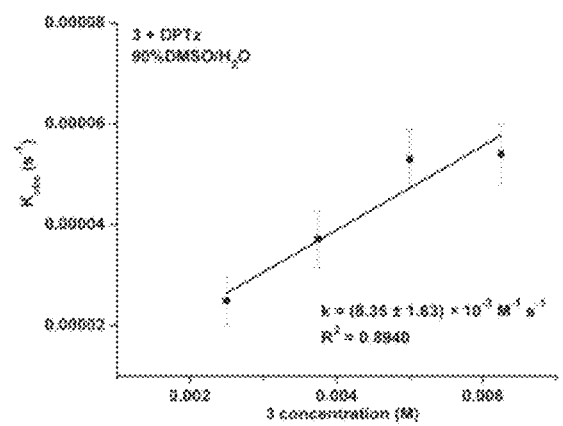
FIG. 22G depicts the second-order rate constant $k_2$ of the reaction with the benzonorbornadiene derivative 3 and the tetrazine DPTz in 90% DMSO/$H_2O$ determined from a plot of pseudo-first order $k_{obs}$ versus concentration of 3. The results are expressed as the mean±standard deviation (n=3).
Figure 22H:
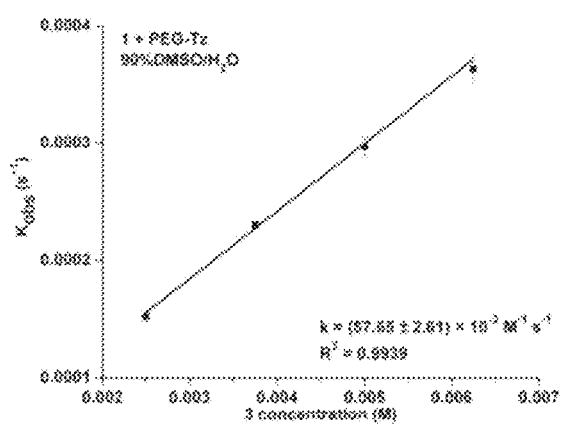
FIG. 22H depicts the second-order rate constant $k_2$ of the reaction with the benzonorbornadiene derivative 1 and the tetrazine PEG-Tz in 90% DMSO/$H_2O$ determined from a plot of pseudo-first order $k_{obs}$ versus concentration of 1. The results are expressed as the mean±standard deviation (n=3).
Figure 22I:
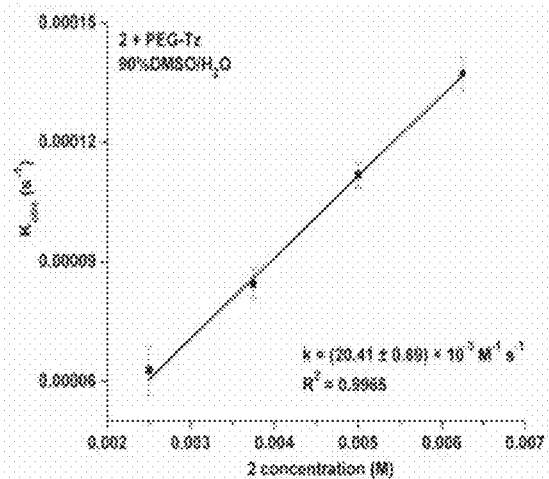
FIG. 22I depicts the second-order rate constant $k_2$ of the reaction with the benzonorbornadiene derivative 2 and the tetrazine PEG-Tz in 90% DMSO/$H_2O$ determined from a plot of pseudo-first order $k_{obs}$ versus concentration of 2. The results are expressed as the mean±standard deviation (n=3).
Figure 22J:
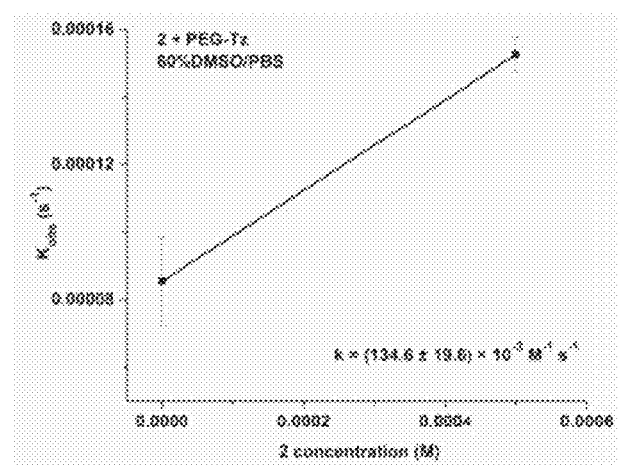
FIG. 22J depicts the second-order rate constant $k_2$ of the reaction with the benzonorbornadiene derivative 2 and the tetrazine PEG-Tz in 60% DMSO/PBS determined from a plot of pseudo-first order $k_{obs}$ versus concentration of 2. The results are expressed as the mean±standard deviation (n=3).
Figure 22K:
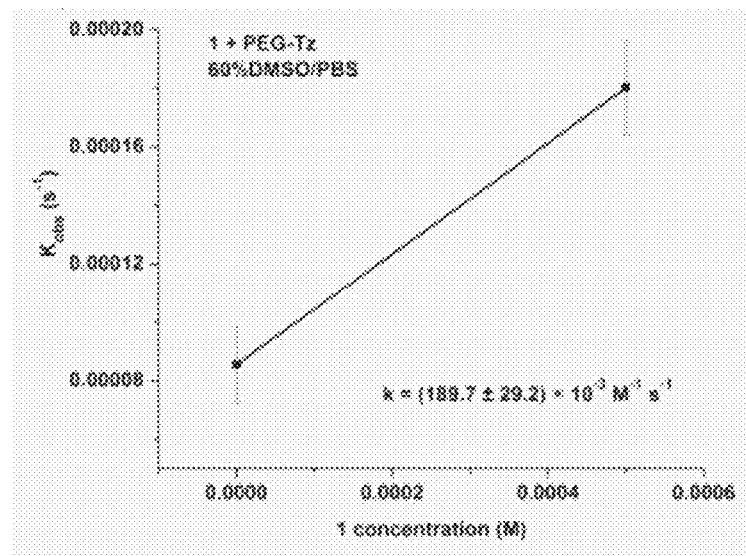
FIG. 22K depicts the second-order rate constant $k_2$ of the reaction with the benzonorbornadiene derivative 1 and the tetrazine PEG-Tz in 60% DMSO/PBS determined from a plot of pseudo-first order $k_{obs}$ versus concentration of 1. The results are expressed as the mean±standard deviation (n=3).

High stability is a major benefit of BNBDs as drug release molecules. No background liberation of reporter molecules was observed even after incubating 2 with human serum for a week (FIG. 21). Additionally, BNBD derivatives are expected to retain their reactivity whereas TCO-derived molecules gradually deactivate by spontaneous trans/cis isomerization. In contrast to the exceptional stability of the BNBD precursors, payload release upon reaction with Tz is rapid and near-quantitative. The combination of high BNBD stability and facile drug release will be essential for achieving a high therapeutic index in targeted drug delivery approaches. This effect was confirmed in cytotoxicity assays with cultured A549 cells. Although the prodrug 5 alone showed no toxicity in the tested concentration range, it was highly cytotoxic when combined with Tz at concentrations that were far below doses tolerated in vivo. Also the rate of the reaction of BNBD and Tz compares favorably with known release designs. The reaction of BNBDs and Tz is significantly faster than many reported bioorthogonal release reactions, and is of similar magnitude to the reaction of TCO-prodrugs with dimethyltetrazine. Considering the strong observed solvent effect (Table 1), it is plausible that the measured rates considerably underestimate the reaction speed in physiological samples.

Further, the straightforward synthesis of BNBD-release molecules is a distinct advantage of these molecules. In particular, the precursor 2d is accessible in a single step. In contrast, the preparation of TCO-prodrugs requires multi-step synthesis, including the separation of the axial from the equatorial stereoisomer.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A bioorthogonal molecule having a structure according to:

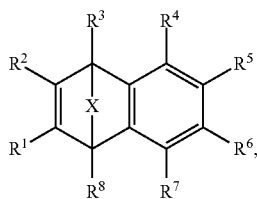

wherein $R^1$, and $R^2$ are independently selected from H, a substituted or unsubstituted $C_1$-$C_3$ alkyl group, or a tether group, and wherein $R^3$—$R^8$ are independently selected from H, a substituted or unsubstituted $C_1$-$C_3$ alkyl group, a tether group, or a leaving group, with the proviso that one of $R^3$—$R^8$ is the leaving group, and wherein X is O, N—Ac, N—Boc, or N-(tether group), and wherein the leaving group is a payload selected from the group consisting of a therapeutic agent, a prodrug, a vitamin, a cytotoxic agent, a protein, a nucleic acid, a lipid, a polymer, a homing molecule, a biomolecule, a macromolecule, and combinations thereof.

2. The bioorthogonal molecule of claim 1, wherein $R^5$ or $R^8$ is the leaving group.

3. The bioorthogonal molecule of claim 2, wherein the leaving group is coupled to $R^5$ or $R^8$ via a linker group.

4. The bioorthogonal molecule of claim 3, wherein the linker group is a substituted or unsubstituted $C_1$-$C_3$ alkyl group.

5. The bioorthogonal molecule of claim 1, wherein $R^8$ is the leaving group.

6. The bioorthogonal molecule of claim 1, wherein the molecule has a structure according to:

where Z is the leaving group,

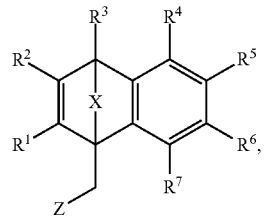

7. The bioorthogonal molecule of claim 1, wherein $R^1$, $R^2$, or both include an electron withdrawing group.

8. The bioorthogonal molecule of claim 7, wherein the electron withdrawing group is a member of the group consisting of COOH, COOR$^9$, COR$^9$, CONR$^9$R$^{10}$, CN, CF$_3$, SO$_2$R$^9$, and NO$_2$, where R$^9$ and R$^{10}$ are independently selected from H and a substituted or unsubstituted $C_1$-$C_3$ alkyl group.

9. The bioorthogonal molecule of claim 1, further where the tether group is configured to tether the molecule to a substrate.

10. The bioorthogonal molecule of claim 9, wherein the tether group is attached to the molecule at one of $R^3$—$R^8$ or at X, where X is N.

11. The bioorthogonal molecule of claim 9, wherein the tether group is attached to the molecule at X, where X is N.

12. The bioorthogonal molecule of claim 9, wherein the substrate is a protein, a nucleic acid, a lipid, a polymer, a biomolecule, a homing molecule, a macromolecule, or a combination thereof.

13. The bioorthogonal molecule of claim 1, further comprising an SR$^{14}$ group coupled to the molecule at $R^2$, wherein R$^{14}$ is selected from H or a substituted or unsubstituted $C_1$-$C_3$ alkyl group.

14. The bioorthogonal molecule of claim 13, further comprising an electron withdrawing group coupled to the molecule at $R^1$, $R^2$, or both.

15. The bioorthogonal molecule of claim 14, wherein the electron withdrawing group is selected from the group consisting of COOH, COOR$^S$, COR$^S$, CONR$^9$R$^1$, CN, CF$_3$, and SO$_2$R$^9$, where R$^9$ and R$^{10}$ are independently selected from H and a substituted or unsubstituted $C_1$-$C_3$ alkyl group.

16. The bioorthogonal molecule of claim 14, wherein both $R^1$ and $R^2$ comprise individual electron withdrawing groups.

17. A therapeutic system, comprising:
    a therapeutic composition, comprising:
        a bioorthogonal molecule according to claim 1, and
        a pharmaceutically acceptable carrier; and
    a releasing composition, comprising:
        a releasing molecule, and
        a second pharmaceutically acceptable carrier.

18. The therapeutic system of claim 17, wherein the therapeutic composition is disposed in a first container and the releasing composition is disposed in a second container.

19. The therapeutic system of claim 17, wherein the bioorthogonal molecule has a structure according to:

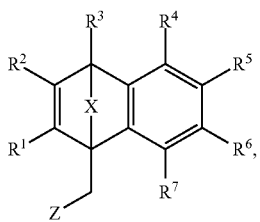

where Z is the leaving group.

20. The therapeutic system of claim 17, wherein the releasing molecule has a structure according to Formula (III):

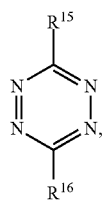

(III)

where $R^{15}$ and $R^{16}$ are independently selected from H, 2-pyridine, and Ph-CONH((CH$_2$)$_2$O)$_3$Me.

21. The therapeutic system of claim 17, wherein the releasing molecule has a structure according to Formula (IV):

where $R^{15}$ and $R^{16}$ are independently selected from H, 2-pyridine, and Ph-CONH((CH$_2$)$_2$O)$_3$Me.

* * * * *